United States Patent [19]
Anthony et al.

[11] Patent Number: 6,080,870
[45] Date of Patent: Jun. 27, 2000

[54] BIARYL SUBSTITUTED IMIDAZOLE COMPOUNDS USEFUL AS FARNESYL-PROTEIN TRANSFERASE INHIBITORS

[75] Inventors: Neville J. Anthony, Hatfield; Robert P. Gomez, Perkasie; Gerald E. Stokker, Gwynedd Valley; John S. Wai; Theresa M. Williams, both of Harleysville; Wasyl Halczenko, Lansdale; John H. Hutchinson, Philadelphia; Steven D. Young, Lansdale, all of Pa.; Kelly M. Solinsky, Cincinnati, Ohio

[73] Assignee: Merck & Co., Inc., Rahway, N.J.

[21] Appl. No.: 09/155,663

[22] PCT Filed: Apr. 1, 1997

[86] PCT No.: PCT/US97/05383

§ 371 Date: Oct. 1, 1998

§ 102(e) Date: Oct. 1, 1998

[87] PCT Pub. No.: WO97/36875

PCT Pub. Date: Oct. 9, 1997

Related U.S. Application Data

[60] Provisional application No. 60/014,592, Apr. 3, 1996, and provisional application No. 60/022,582, Jul. 24, 1996.

[51] Int. Cl.[7] .................. C07D 233/30; C07D 233/32; C07D 233/64; C07D 233/66; A61K 31/4164; A61K 31/4174
[52] U.S. Cl. .................. 548/324.1; 514/398; 514/399; 514/400; 548/336.1; 548/343.1
[58] Field of Search .................. 548/324.1, 336.1, 548/343.1; 514/398, 399, 400, 401

[56] References Cited

U.S. PATENT DOCUMENTS

| | | | |
|---|---|---|---|
| 4,207,324 | 6/1980 | Matsumura et al. | 434/273 R |
| 4,749,713 | 6/1988 | Bowman et al. | 514/341 |
| 4,837,333 | 6/1989 | Manley et al. | 548/341 |
| 4,916,144 | 4/1990 | Strehlke et al. | 514/326 |
| 5,126,342 | 6/1992 | Chakravarty et al. | 514/235.8 |
| 5,219,856 | 6/1993 | Olson | 514/252 |
| 5,296,609 | 3/1994 | McCort et al. | 548/325.1 |
| 5,326,776 | 7/1994 | Winn et al. | 514/382 |
| 5,538,987 | 7/1996 | Salimbeni et al. | 514/341 |
| 5,559,141 | 9/1996 | Karjalainen et al. | 514/400 |
| 5,576,313 | 11/1996 | Fisher et al. | 514/211 |

FOREIGN PATENT DOCUMENTS

| | | |
|---|---|---|
| 0 648 763 A1 | 4/1995 | European Pat. Off. . |
| 31 45 928 | 6/1983 | Germany . |
| 2273704 | 6/1994 | United Kingdom . |
| WO 93/13075 | 7/1993 | WIPO . |
| WO 94/08973 | 4/1994 | WIPO . |
| WO 95/00493 | 1/1995 | WIPO . |
| WO 96/30343 | 10/1996 | WIPO . |
| WO 96/34851 | 11/1996 | WIPO . |
| WO 96/37204 | 11/1996 | WIPO . |

OTHER PUBLICATIONS

Exp. Opin. Ther. Patents, vol. 5(12), pp. 1269–1271 (1995), by S. L. Graham.
Exp. Opin. Ther. Patents, vol.6(12) (1996), pp. 1295–1304, by S. L. Graham, et al.
J. of Biol. Chem., vol. 268, No. 11, pp. 7617–7620 (1993), by J. B. Gibbs, et al.
J. of Biol. Chem., vol. 269, No. 44, pp. 27706–27714 (1994), by G. L. James, et al.
J. of Biol. Chem., vol. 270, No. 11, pp. 6221–6226 (1995), by G. L. James, et al.
Science, vol. 260, pp. 1934–1937 (1993), by N. E. Kohl, et al.
Proc. Natl. Acad. Sci. USA, vol. 91, pp. 9141–9145 (1994), by N. E. Kohl, et al.
Nature Medicine, vol. 1, No. 8, pp. 792–797 (1995), by N. E. Kohl, et al.
Cancer Research, vol. 55, pp. 5302–5309 (1995), by L. Sepp–Lorenzino, et al.

*Primary Examiner*—Floyd D. Higel
*Attorney, Agent, or Firm*—J. Antonio Garcia-Rivas; Mark R. Daniel; David A. Muthard

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

36 Claims, No Drawings

BIARYL SUBSTITUTED IMIDAZOLE COMPOUNDS USEFUL AS FARNESYL-PROTEIN TRANSFERASE INHIBITORS

RELATED APPLICATIONS

This application is a § 371 of PCT/US97/05383 filed Apr. 1, 1997. This application claims the benefit of U.S. provisional application No. 60/014,592, filed Apr. 3, 1996, and U.S. provisional application No. 60/022,582, filed Jul. 24, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochen.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in four general classes (S. Graham, *Expert Opinion Ther. Patents*, (1995) 5:1269–1285). The first are analogs of farnesyl diphosphate (FPP), while a second class of inhibitors is related to the protein substrates (e.g., Ras) for the enzyme. Bisubstrate inhibitors and inhibitors of farnesyl-protein transferase that are non-competitive with the substrates have also been described. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It is, therefore, an object of this invention to develop low molecular weight compounds that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises novel biaryl-containing compounds which inhibit the farnesyl-protein transferase.

Further contained in this invention are chemotherapeutic compositions containing these farnesyl transferase inhibitors and methods for their production.

The compounds of this invention are illustrated by the formula A:

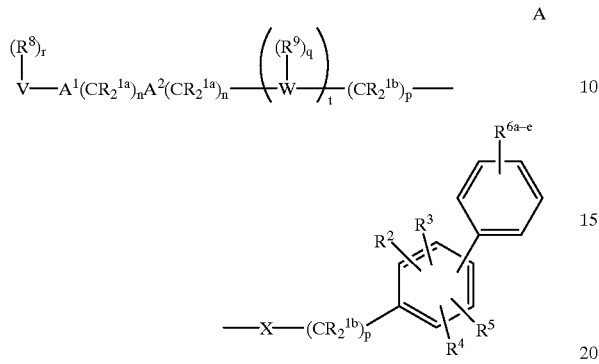

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

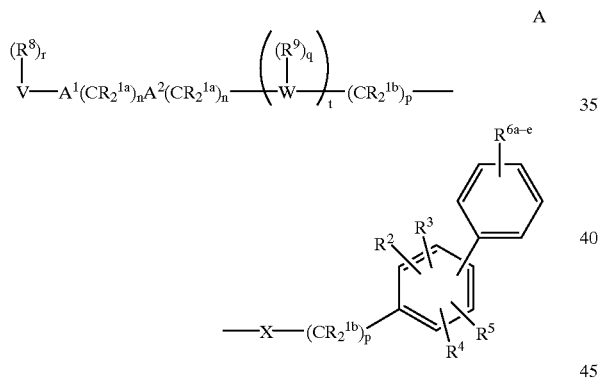

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^2$, $R^3$, $R^4$ and $R^5$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{11}S(O)_mNR^{10}$—, $(R^{10})_2NS(O)_m$—, $R^{13}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^2$, $R^3$, $R^4$, $R^5$, $R^{6a}$, $R^{6b}$, $R^{6c}$, $R^{6d}$ or $R^{6e}$ is unsubstituted or substituted heterocycle, attachment of $R^2$, $R^3$, $R^4$, $R^5$, $R^{6a}$, $R^{6b}$, $R^{6c}$, $R^{6d}$ or $R^{6e}$ to the phenyl ring is through a substitutable heterocycle ring carbon;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO, e)

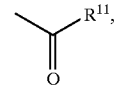

f) —$SO_2R^{11}$
g) $N(R^{10})_2$ or
h) $C_{1-4}$ perfluoroalkyl;

$R^8$ is independently selected from:
a) hydrogen,
b) aryl, substituted aryl, heterocycle, substituted heterocycle $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}C(O)NR^{10}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $N_3$, —$N(R^{10})_2$, or $R^{10}OC(O)NH$—;

provided that when $R^8$ is heterocycle, attachment of $R^8$ to V is through a substitutable ring carbon;

$R^9$ is independently selected from:
  a) hydrogen,
  b) $C_2$–$C_6$ alkenyl, $C_2$–$C_6$ alkynyl, $C_1$–$C_6$ perfluoroalkyl, halogen $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{13}$ is independently selected from hydrogen, $C_1$–$C_6$ alkyl, 2,2,2-trifluoroethyl, —$CH_2N(R^{10})_2$, benzyl and aryl;

$A^1$ and $A^2$ are independently selected from: a bond, —CH=CH—, —C≡C—, —C(O)—, —C(O)$NR^{10}$—, —$NR^{10}C(O)$—, O, —$N(R^{10})$—, —$S(O)_2N(R^{10})$—, —$N(R^{10})S(O)_2$— or $S(O)_m$;

V is selected from:
  a) hydrogen,
  b) heterocycle,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a substitutable ring carbon;

W is a heterocycle;

X is a bond, —CH=CH—, O, —C(=O)—, —C(O)$NR^7$—, —$NR^7C(O)$—, —C(O)O—, —OC(O)—, —C(O)$NR^7C(O)$—, —$S(O)_2N(R^{10})$—, —$N(R^{10})S(O)_2$— or —$S(=O)_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;

or the pharmaceutically acceptable salts thereof.

A preferred embodiment of the compounds of this invention is illustrated by the following formula:

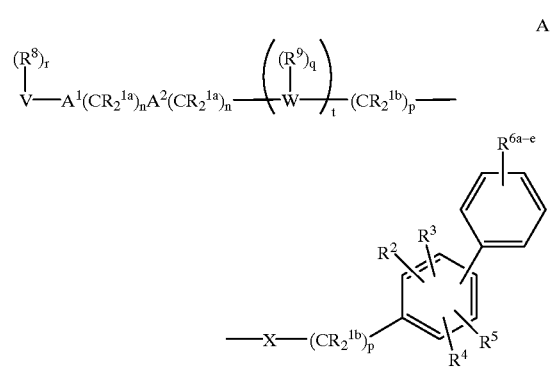

wherein:

$R^{1a}$ is independently selected from: hydrogen $C_3$–$C_{10}$ cycloalkyl, $R^{10}O$—, —$N(R^{10})_2$, F or $C_1$–$C_6$ alkyl;

$R^{1b}$ is independently selected from:
  a) hydrogen,
  b) aryl, heterocycle, $C_3$–$C_{10}$ cycloalkyl, $R^{10}O$—, —$N(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^2$, $R^3$, $R^4$ and $R^5$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl;
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl;
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{11}S(O)_mNR^{10}$—, $(R^{10})_2NS(O)_m$—, $R^{13}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}C(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^3$, $R^4$, $R^5$, $R^{6a}$, $R^{6b}$, $R^{6c}$, $R^{6d}$ or $R^{6e}$ is unsubstituted or substituted heterocycle, attachment of $R^2$, $R^3$, $R^4$, $R^5$, $R^{6a}$, $R^{6b}$, $R^{6c}$, $R^{6d}$ or $R^{6e}$ to the phenyl ring is through a substitutable heterocycle ring carbon;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO, e)
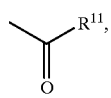

f) —SO$_2$R$^{11}$
g) N(R$^{10}$)$_2$ or
h) $C_{1-4}$ perfluoroalkyl;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

provided that when $R^8$ is heterocycle, attachment of $R^8$ to V is through a substitutable ring carbon;

$R^9$ is independently selected from:
a) hydrogen,
b) $C_2$–$C_6$ alkenyl, $C_2$–$C_6$ alkynyl, $C_1$–$C_6$ perfluoroalkyl, F, Cl, R$^{11}$O—, R$^{11}$S(O)$_m$—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl unsubstituted or substituted by $C_1$–$C_6$ perfluoroalkyl, F, Cl, R$^{10}$O—, R$^{11}$S(O)$_m$—, R$^{10}$C(O)NR$^{10}$—, (R$^{10}$)$_2$NC(O)—, CN, (R$^{10}$)$_2$N—C(NR$^{10}$)—, R$^{10}$C(O)—, —N(R$^{10}$)$_2$, or R$^{11}$OC(O)NR$^{10}$—;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$R^{13}$ is independently selected from hydrogen, $C_1$–$C_6$ alkyl, 2,2,2-trifluoroethyl, —CH$_2$N(R$^{10}$)$_2$, benzyl and aryl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, imidazolinyl, pyridinyl, thiazolyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

provided that when V is heterocycle, attachment of V to $R^8$ and to $A^1$ is through a substitutable ring carbon;

W is a heterocycle selected from pyrrolidinyl, imidazolyl, imidazolinyl, pyridinyl, thiazolyl, oxazolyl, indolyl, quinolinyl, triazolyl or isoquinolinyl;

X is a bond, O, —C(=O)—, —CH=CH—, —C(O)NR$^7$—, —NR$^7$C(O)—, —S(O)$_2$N(R$^{10}$)—, —N(R$^{10}$)S(O)$_2$— or —S(=O)$_m$—;

m is 0, 1 or 2;
n is independently 0, 1, 2, 3 or 4;
q is 0, 1, 2 or 3;
p is independently 0, 1, 2, 3 or 4;
r is 0 to 5, provided that r is 0 when V is hydrogen; and
t is 0 or 1;

or the pharmaceutically acceptable salts thereof.

A preferred embodiment of the compounds of this invention are illustrated by the formula B:

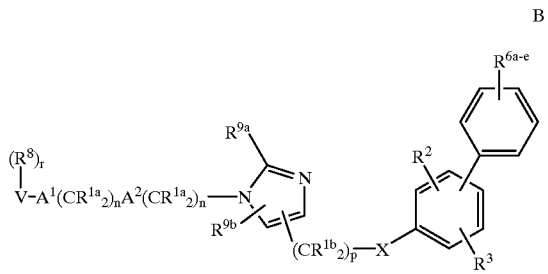

B wherein:

$R^{1a}$ is independently selected from: hydrogen, $C_3$–$C_{10}$ cycloalkyl, R$^{10}$O—, —N(R$^{10}$)$_2$, F or $C_1$–$C_6$ alkyl;

$R^{1b}$ is independently selected from:
a) hydrogen,
b) aryl, heterocycle, $C_3$–$C_{10}$ cycloalkyl, R$^{10}$O—, —N(R$^{10}$)$_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, R$^{10}$O— and —N(R$^{10}$)$_2$;

$R^2$ and $R^3$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{11}S(O)_mNR^{10}$—, $(R^{10})_2NS(O)_m$—, $R^{13}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^3$, $R^{6a}$, $R^{6b}$, $R^{6c}$, $R^{6d}$ or $R^{6e}$ is unsubstituted or substituted heterocycle, attachment of $R^2$, $R^3$, $R^{6a}$, $R^{6b}$, $R^{6c}$, $R^{6d}$ or $R^{6e}$ to the phenyl ring is through a substitutable heterocycle ring carbon;

$R^8$ is independently selected from:
  a) hydrogen,
  b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a substitutable ring carbon;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{13}$ is independently selected from hydrogen, $C_1$–$C_6$ alkyl, 2,2,2-trifluoroethyl, —CH$_2$N(R$^{10}$)$_2$, benzyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, or S(O)$_m$;

V is selected from:
  a) hydrogen,
  b) heterocycle selected from pyrrolidinyl, imidazolyl, imidazolinyl, pyridinyl, thiazolyl, oxazolyl, indolyl, quinolinyl, isoquinolinyl, triazolyl and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a substitutable ring carbon;

X is a bond, —CH=CH—, —C(O)NR$^{10}$—, —NR$^{10}$C(O)—, O or —C(=O)—;

m is 0, 1 or 2;

n is independently 0, 1, 2, 3 or 4;

p is 0, 1, 2, 3 or 4; and r is 0 to 5, provided that r is 0 when V is hydrogen;

or the pharmaceutically acceptable salts thereof.

Another preferred embodiment of the compounds of this invention are illustrated by the formula C:

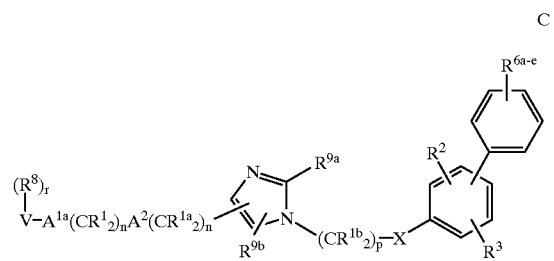

wherein:

$R^{1a}$ is independently selected from: hydrogen, $C_3$–$C_{10}$ cycloalkyl, $R^{10}O$—, —$N(R^{10})_2$, F or $C_1$–$C_6$ alkyl;

$R^{1b}$ is independently selected from:
  a) hydrogen,
  b) aryl, heterocycle, $C_3$–$C_{10}$ cycloalkyl, $R^{10}O$—, —$N(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^2$ and $R^3$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $CN(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $CN(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$, c) unsubstituted $C_1-C_6$ alkyl, d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{11}S(O)_mNR^{10}-$, $(R^{10})_2NS(O)_m-$, $R^{13}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$;

any two of $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$;

provided that when $R^2$, $R^3$, $R^{6a}$, $R^{6b}$, $R^{6c}$, $R^{6d}$ or $R^{6e}$ is unsubstituted or substituted heterocycle, attachment of $R^2$, $R^3$, $R^{6a}$, $R^{6b}$, $R^{6c}$, $R^{6d}$ or $R^{6e}$ to the phenyl ring is through a substitutable heterocycle ring carbon;

$R^8$ is independently selected from:
a) hydrogen,
b) aryl, substituted aryl, heterocycle, $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

provided that when $R^8$ is heterocycle, attachment of $R^8$ to V is through a substitutable ring carbon;

$R^{9a}$ and $R^{9b}$ are independently hydrogen, $C_1-C_6$ alkyl, trifluoromethyl and halogen;

$R^{10}$ is independently selected from hydrogen, $C_1-C_6$ alkyl, 2,2,2-trifluoroethyl, benzyl and aryl;

$R^{11}$ is independently selected from $C_1-C_6$ alkyl and aryl;

$R^{12}$ is independently selected from hydrogen, $C_1-C_6$ alkyl, $C_1-C_6$ aralkyl, $C_1-C_6$ substituted aralkyl, $C_1-C_6$ heteroaralkyl, $C_1-C_6$ substituted heteroaralkyl, aryl, substituted aryl, heteroaryl, substituted heteraryl, $C_1-C_6$ perfluoroalkyl, 2-aminoethyl and 2,2,2-trifluoroethyl;

$R^{13}$ is independently selected from hydrogen, $C_1-C_6$ alkyl, 2,2,2-trifluoroethyl, $-CH_2N(R^{10})_2$, benzyl and aryl;

$A^1$ and $A^2$ are independently selected from: a bond, $-CH=CH-$, $-C\equiv C-$, $-C(O)-$, $-C(O)NR^{10}-$, O, $-N(R^{10})-$, or $S(O)_m$;

V is selected from:
a) hydrogen,
b) heterocycle selected from pyrrolidinyl, imidazolyl, imidazolinyl, pyridinyl, thiazolyl, oxazolyl, indolyl, quinolinyl, isoquinolinyl, triazolyl and thienyl,
c) aryl,
d) $C_1-C_{20}$ alkyl wherein from 0 to 4 carbon atoms are replaced with a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a substitutable ring carbon;

X is a bond, $-CH=CH-$, $-C(O)NR^{10}-$, $-NR^{10}C(O)-$, O or $-C(=O)-$;

m is 0, 1 or 2;

n is independently 0, 1, 2, 3 or 4;

p is 0, 1, 2, 3 or 4, provided that p is not 0 if X is a bond, $-NR^{10}C(O)-$, $-NR^{10}-$ or O; and r is 0 to 5, provided that r is 0 when V is hydrogen;

or the pharmaceutically acceptable salts thereof.

In a more preferred embodiment of this invention, the inhibitors of farnesyl-protein transferase are illustrated by the formula D:

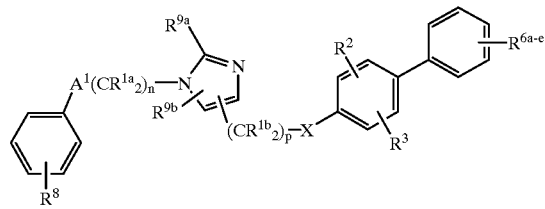

wherein:
$R^{1a}$ is independently selected from: hydrogen, $C_3-C_{10}$ cycloalkyl or $C_1-C_6$ alkyl;

$R^{1b}$ is independently selected from:
a) hydrogen,
b) aryl, heterocycle, $C_3-C_{10}$ cycloalkyl, $R^{10}O-$, $-N(R^{10})_2$, F or $C_2-C_6$ alkenyl,
c) $C_1-C_6$ alkyl unsubstituted or substituted by aryl, heterocycle, $C_3-C_{10}$ cycloalkyl, $C_2-C_6$ alkenyl, $R^{10}O-$, or $-N(R^{10})_2$;

$R^2$ is selected from:
a) hydrogen,
b) unsubstituted or substituted aryl, unsubstituted or substituted heterocycle, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$;

$R^3$ is selected from H, halogen, $C_1-C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3-C_{10}$ cycloalkyl, $C_2-C_6$ alkenyl, $C_2-C_6$ alkynyl, halogen, $C_1-C_6$ perfluoroalkyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^{6a}$, $R^{6b}$, $R^{6c}$, $R^{6d}$ or $R^{6e}$ is unsubstituted or substituted heterocycle, attachment of $R^2$, $R^{6a}$, $R^{6b}$, $R^{6c}$, $R^{6d}$ or $R^{6e}$ to the phenyl ring is through a substitutable heterocycle ring carbon;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, NO$_2$, $(R^{10})_2N$—$C(NR^{10})$, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—; or provided that when $R^8$ is heterocycle, attachment of $R^8$ to V is through a substitutable ring carbon;

$R^{9a}$ and $R^{9b}$ are independently hydrogen, halogen, CF$_3$ or methyl;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ is selected from: a bond, —C(O)—, O, —N(R$^{10}$)—, or S(O)$_m$;

X is a bond, —CH=CH—, —C(O)NR$^{10}$—, —NR$^{10}$C(O)—, O or —C(=O)—;

n is 0 or 1; provided that n is not 0 if $A^1$ is a bond, O, —N(R$^{10}$)—, or S(O)$_m$;

m is 0, 1 or 2; and p is 0, 1, 2, 3 or 4;

or the pharmaceutically acceptable salts thereof.

In another more preferred embodiment of this invention, the inhibitors of farnesyl-protein transferase are illustrated by the formula E:

wherein:

$R^{1a}$ is independently selected from: hydrogen, $R^{10}O$—, —$N(R^{10})_2$, F, $C_3$–$C_{10}$ cycloalkyl or $C_1$–$C_6$ alkyl;

$R^{1b}$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})$—;

$R^2$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)_2$, $R^{10}{}_2N$—$C(NR^{10})$—, CN, NO$_2$, $R^{10}C(O)$—, $N_3$, —$N(R^{10})_2$, or $R^{11}C(O)NR^{10}$—,
c) unsubstituted $C_1$–$C_6$ alkyl,
d) substituted $C_1$–$C_6$ alkyl wherein the substituent on the substitstitued $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^3$ is selected from H, halogen, $C_1$–$C_6$ alkyl and CF$_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, NO$_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from

E

—CH=CH—CH=CH—, —CH=CH—CH$_2$—, —(CH$_2$)$_4$— and —(CH$_2$)$_3$—;

provided that when R$^2$, R$^{6a}$, R$^{6b}$, R$^{6c}$, R$^{6d}$ or R$^{6e}$ is unsubstituted or substituted heterocycle, attachment of R$^2$, R$^{6a}$, R$^{6b}$, R$^{6c}$, R$^{6d}$ or R$^{6e}$ to the phenyl ring is through a substitutable heterocycle ring carbon;

R$^8$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

provided that when R$^8$ is heterocycle, attachment of R$^8$ to V is through a substitutable ring carbon;

R$^{9a}$ and R$^{9b}$ are independently hydrogen, halogen, CF$_3$ or methyl;

R$^{10}$ is independently selected from hydrogen, C$_1$–C$_6$ alkyl, 2,2,2-trifluoroethyl, benzyl and aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

X is a bond, —CH=CH—, —C(O)NR$^{10}$—, —NR$^{10}$C(O)—, O or —C(=O)—;

n is 0 or 1;

m is 0, 1 or 2; and p is 0, 1, 2, 3 or 4, provided that p is not 0 if X is a bond or O;

or the pharmaceutically acceptable salts thereof.

In a further embodiment of this invention, the inhibitors of farnesyl-protein transferase are illustrated by the formula F:

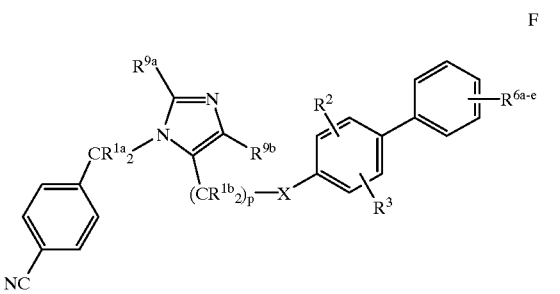

F wherein:
R$^{1a}$ is independently selected from: hydrogen, C$_3$–C$_{10}$ cycloalkyl or C$_1$–C$_6$ alkyl;
R$^{1b}$ is independently selected from:
a) hydrogen,
b) aryl, heterocycle, C$_3$–C$_{10}$ cycloalkyl, R$^{10}$O—, —N(R$^{10}$)$_2$ or F,
c) C$_1$–C$_6$ alkyl unsubstituted or substituted by aryl, heterocycle, C$_3$–C$_{10}$ cycloalkyl, R$^{10}$O—, or —N(R$^{10}$)$_2$;
R$^2$ is selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^3$ is selected from H, halogen, CH$_3$ and CF$_3$;

R$^{6a}$, R$^{6b}$, R$^{6c}$, R$^{6d}$ and R$^{6e}$ are independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—; or any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when R$^2$, R$^{6a}$, R$^{6b}$, R$^{6c}$, R$^{6d}$ or R$^{6e}$ is unsubstituted or substituted heterocycle, attachment of R$^2$, R$^{6a}$, R$^{6b}$, R$^{6c}$, R$^{6d}$ or R$^{6e}$ to the phenyl ring is through a substitutable heterocycle ring carbon;

R$^{9a}$ and R$^{9b}$ are independently hydrogen, halogen, CF$_3$ or methyl;

R$^{10}$ is independently selected from hydrogen, C$_1$–C$_6$ alkyl, benzyl and aryl;

R$^{11}$ is independently selected from C$_1$–C$_6$ alkyl and aryl;

R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

X is a bond, —CH=CH—, —C(O)NR$^{10}$—, —NR$^{10}$C(O)—, O or —C(=O)—;

m is 0, 1 or 2; and p is 0, 1, 2, 3 or 4;

or the pharmaceutically acceptable salts thereof.

In a further embodiment of this invention, the inhibitors of farnesyl-protein transferase are illustrated by the formula G:

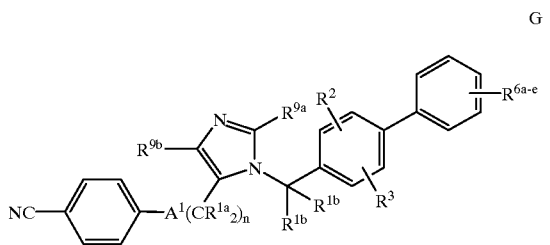

wherein:
R$^{1a}$ is independently selected from: hydrogen, R$^{10}$O—, —N(R$^{10}$)$_2$, F, C$_3$–C$_{10}$ cycloalkyl or C$_1$–C$_6$ alkyl;
R$^{1b}$ is independently selected from:
  a) hydrogen,
  b) aryl, heterocycle or C$_3$–C$_{10}$ cycloalkyl,
  c) C$_1$–C$_6$ alkyl unsubstituted or substituted by aryl, heterocycle, C$_3$–C$_{10}$ cycloalkyl, C$_2$–C$_6$ alkenyl, R$^{10}$O—, or —N(R$^{10}$)$_2$;
R$^2$ is selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, R$^{10}$C(O)—, N$_3$, —N(R$^{10}$)$_2$, and R$^{11}$OC(O)—NR$^{10}$—;
R$^3$ is selected from H, halogen, CH$_3$ and CF$_3$;
R$^{6a}$, R$^{6b}$, R$^{6c}$, R$^{6d}$ and R$^{6e}$ are independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, R$^{10}$C(O)—, N$_3$, —N(R$^{10}$)$_2$, and R$^{11}$OC(O)—NR$^{10}$—; or
any two of R$^{6a}$, R$^{6b}$, R$^{6c}$, R$^{6d}$ and R$^{6e}$ on adjacent carbon atoms are combined to form a diradical selected from —CH=CH—CH=CH—, —CH=CH—CH$_2$—, —(CH$_2$)$_4$— and —(CH$_2$)$_3$—;
provided that when R$^2$, R$^{6a}$, R$^{6b}$, R$^{6c}$, R$^{6d}$ or R$^{6e}$ is unsubstituted or substituted heterocycle, attachment of R$^2$, R$^{6a}$, R$^{6b}$, R$^{6c}$, R$^{6d}$ or R$^{6e}$ to the phenyl ring is through a substitutable heterocycle ring carbon;

R$^{9a}$ and R$^{9b}$ are independently hydrogen, halogen, CF$_3$ or methyl;
R$^{10}$ is independently selected from hydrogen, C$_1$–C$_6$ alkyl, 2,2,2-trifluoroethyl, benzyl and aryl;
R$^{11}$ is independently selected from C$_1$–C$_6$ alkyl and aryl;
R$^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted hetaryl, C$_1$–C$_6$ perfluoroalkyl, 2-aminoethyl and 2,2,2-trifluoroethyl;
A$^1$ is selected from: a bond, —C(O)—, O, —N(R$^{10}$)—, or S(O)$_m$;
m is 0, 1 or 2; and
n is 0 or 1;
or the pharmaceutically acceptable salts thereof.

The preferred compounds of this invention are as follows:
1-(4-Biphenylmethyl)-5-(4-cyanobenzyl)imidazole
1-(4-Cyanobenzyl)-5-(4'-phenylbenzamido)ethyl-imidazole
1-(2'-Trifluoromethyl-4-biphenylmethyl)-5-(4-cyanobenzyl)imidazole
1-(4-Biphenylethyl)-5-(4-cyanobenzyl)imidazole
1-(2'-Bromo-4-biphenylmethyl)-5-(4-cyanobenzyl)imidazole
1-(2'-Methyl-4-biphenylmethyl)-5-(4-cyanobenzyl)imidazole
1-(2'-Trifluoromethoxy-4-biphenylmethyl)-5-(4-cyanobenzyl) imidazole
1-(4-(3',5'-dichloro)-biphenylmethyl)-5-(4-cyanobenzyl) imidazole
1-(2'-Methoxy-4-biphenylmethyl)-5-(4-cyanobenzyl) imidazole
1-(2'-Chloro-4-biphenylmethyl)-5-(4-cyanobenzyl)imidazol
1-(2-Chloro-4-biphenylmethyl)-5-(4-cyanobenzyl) imidazole
1-(3-Chloro-4-biphenylmethyl)-5-(4-cyanobenzyl) imidazole
1-(4-(3',5'-Bis-trifluoromethyl)-biphenylmethyl)-5-(4-cyanobenzyl) imidazole
1-(2'-Trifluoromethyl-4-biphenylmethyl)-5-(4-cyanobenzyl)-4-methylimidazole
1-(4-Biphenylmethyl)-5-(4-cyanophenyloxy)-imidazole
5-(4-Cyanophenyloxy)-1-(2'-methyl-4-biphenylmethyl)-imidazole
5-(4-Biphenyloxy)-1-(4-eyanobenzyl)-imidazole
5-(2'-Methyl-4-biphenoxy)-1-(4-cyanobenzyl)-imidazole
5-(4-(3',5'-dichloro)biphenylmethyl)-1-(4-cyanobenzyl) imidazole
1-(4-biphenylmethyl)-5-(1-(R,S)-acetoxy-1-(4-cyanophenyl)methylimidazole
1-(4-Biphenylmethyl)-5-(1-(R,S)-hydroxy-1-(4-cyanophenyl) methylimidazole
1-(4-Biphenylmethyl)-5-(1-(R,S)-amino-1-(4-cyanophenyl) methylimidazole
1-(4-biphenylmethyl)-5-(1-(R,S)-methoxy-1-(4-cyanophenyl)-methylimidazole
1-(4-Cyanobenzyl)-5-(1-hydroxy-1-(4-biphenyl)-methyl) imidazole
1-(4-Cyanobenzyl)-5-(1-oxo-1-(4-biphenyl)-methyl) imidazole
1-(4-Cyanobenzyl)-5-(1-hydroxy-1-(3-fluoro-4-biphenyl)-methyl)-imidazole
1-(4-Cyanobenzyl)-5-(1-hydroxy-1-(3-biphenyl)methyl-imidazole
5-(2-[1,1'-Biphenyl]vinylene)-1-(4-cyanobenzyl)imidazole
1-(4-Biphenylmethyl)-5-(4-bromophenyloxy)-imidazole 1-(3'-Methyl-4-biphenylmethyl)-5-(4-cyanobenzyl) imidazole
1-(4'-Methyl-4-biphenylmethyl)-5-(4-cyanobenzyl) imidazole
1-(3'-Trifluoromethyl-4-biphenylmethyl)-5-(4-cyanobenzyl) imidazole
1-(4'-Trifluoromethyl-4-biphenylmethyl)-5-(4-cyanobenzyl) imidazole
1-(3'-Chloro-4-biphenylmethyl)-5-(4-cyanobenzyl) imidazole
1-(4'-Chloro-4-biphenylmethyl)-5-(4-cyanobenzyl) imidazole
1-(2'3'-Dichloro-4-biphenylmethyl)-5-(4-cyanobenzyl) imidazole
1-(2'4'-Dichloro-4-biphenylmethyl)-5-(4-cyanobenzyl) imidazole
1-(2'5'-Dichloro-4-biphenylmethyl)-5-(4-cyanobenzyl) imidazole
1-(3'-Trifluoromethoxy-4-biphenylmethyl)-5-(4-cyanobenzyl) inidazole
1-(2'-Fluoro-4-biphenylmethyl)-5-(4-cyanobenzyl) imidazole
1-(4-(2'-Trifluoromethylphenyl)-2-Chlorophenylmethyl)-5-(4-cyanobenzyl)imidazole
1-{1-(4-(2'-trifluoromethylphenyl)phenyl)ethyl}-5-(4-cyanobenzyl) imidazole
1-(2'-Trifluoromethyl-4-biphenylpropyl)-5-(4-cyanobenzyl) imidazole
1-(2'-N-t-Butoxycarbonylamino-4-biphenylmethyl)-5-(4-cyanobenzyl)imidazole
1-(2'-Aminomethyl-4-biphenylmethyl)-5-(4-cyanobenzyl) imidazole
1-(2'-Acetylaminomethyl-4-biphenylmethyl)-5-(4-cyanobenzyl) imidazole
1-(2'-Methylsulfonylaminomethyl-4-biphenylmethyl)-5-(4-cyanobenzyl)imidazole
1-(2'-Ethylaminomethyl-4-biphenylmethyl)-5-(4-cyanobenzyl) imidazole
1-(2'-Phenylaminomethyl-4-biphenylmethyl)-5-(4-cyanobenzyl) imidazole
1-(2'-Glycinylaminomethyl-4-biphenylmethyl)-5-(4-cyanobenzyl) imidazole
1-(2'-Methyl-4-biphenylmethyl)-2-chloro-5-(4-cyanobenzyl) imidazole
1-(2'-Methyl-4-biphenylmethyl)-4-chloro 5-(4-cyanobenzyl) imidazole
1-(3'-Chloro-2-methyl-4-biphenylmethyl)-4-(4-cyanobenzyl)imidazole
1-(3'-Chloro-2-methyl-4-biphenylmethyl)-5-(4-cyanobenzyi)imidazole
1-(3'-Trifluoromethyl-2-methyl-4-biphenylmethyl)-4-(4-cyanobenzyl)imidazole
1-(3'-Trifluoromethyl-2-methyl-4-biphenylmethyl)-5-(4-cyanobenzyl)imidazole
1-(3'-Methoxy-2-methyl-4-biphenylmethyl)-5-(4-cyanobenzyl)imidazole
1-(2'-Chloro-4'-fluoro-4-biphenylmethyl)-5-(4-cyanobenzyl)imidazole 1-(2'-Ethyl-4-biphenylmethyl)-5-(4-cyanobenzyl)imidazole
1-(2'-(2-Propyl)-4-biphenylmethyl)-5-(4-cyanobenzyl) imidazole
1-(2'-(2-Methyl-2-propyl)-4-biphenylmethyl)-5-(4-cyanobenzyl)imidazole
1-(2'-Ethyl-4-biphenylmethyl)-5-(4-(1H-tetrazol-5-yl))benzyl)imidazole
1-[1-(4-Cyanobenzyl)imidazol-5-ylmethoxy]-4-(2'-methylphenyl)-2-(3-N-phthalimido-1-propyl)benzene
1-(3',5'-Ditrifluoromethyl-2-methyl-4-biphenylmethyl)-5-(4-cyanobenzyl)imidazole
1-(3',5'-Chloro-2-methyl-4-biphenylmethyl)-5-(4-cyanobenzyl)imidazole
1-(3',5'-Dimethyl-2-methyl-4-biphenylmethyl)-5-(4-cyanobenzyl)imidazole
1-(3-(N-Boc-aminomethyl)-4-biphenylmethyl)-5-(4-cyanobenzyl)-imidazole
1-(3-Aminomethyl-4-biphenylmethyl)-5-(4-cyanobenzyl) imidazole
1-(4-Cyanobenzyl)-2-methyl-5-(2'-methylbiphenyl-4-yloxy)imidazole
5-(4-Cyanobenzyl)-1-(3-cyano-2'-trifluoromethylbiphenyl-4-ylmethyl)-imidazole
2-Amino-5-(biphenyl-4-ylmethyl)-1-(4-cyanobenzyl) imidazole 2-Amino-1-(biphenyl-4-ylmethyl)-5-(4-cyanobenzyl)imidazole 1-(3-Butylbiphenyl-4-ylmethyl)-5-(4-cyanobenzyl)-imidazole 1-(3-Propylbiphenyl-4-ylmethyl)-5-(4-cyanobenzyl)-imidazole
1-(4-Biphenylmethyl)-4-(4-cyanobenzyl-2-methylimidazole 1-(4-Cyanobenzyl)-5-[(3-fluoro-4-biphenyl)methyl]imidazole
1-(4-Cyanobenzyl)-5-[1-(4-biphenyl)-1-hydroxy]ethyl-2-methylimidazole
1-(4-Cyanobenzyl)-5-(4-biphenylmethyl)-2-methylimidazole
1-(4-Cyanobenzyl)-5-[1-(4-biphenyl)]ethyl-2-methyl imidazole
1-(4-Cyanobenzyl-5-[1-(4-biphenyl)]vinylidene-2-methylimidazole and
1-(4-Cyanobenzyl)-5-[2-(4-biphenyl)]vinylene-2-methylimidazole
or the pharmaceutically acceptable salts or optical isomers thereof.

Specific examples of the compounds of the invention are;
1-(4-Biphenylmethyl)-5-(4-cyanobenzyl)imidazole

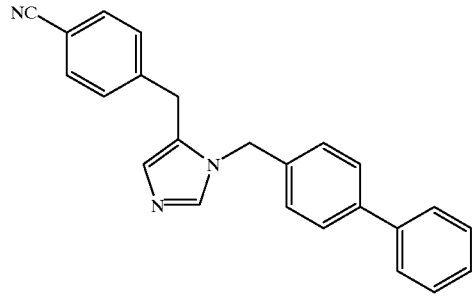

1-(2'-Methyl-4-biphenylmethyl)-5-(4-cyanobenzyl) imidazole

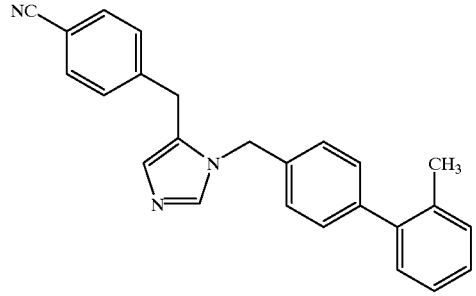

1-(2'-Methoxy-4-biphenylmethyl)-5-(4-cyanobenzyl) imidazole

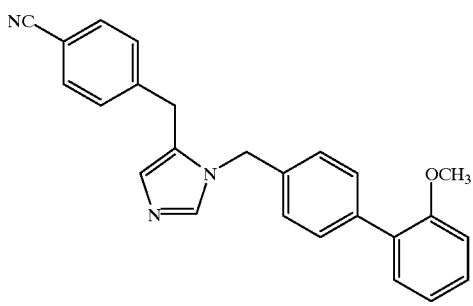

1-(4'-Chloro-4-biphenylmethyl)-5-(4-cyanobenzyl) imidazole

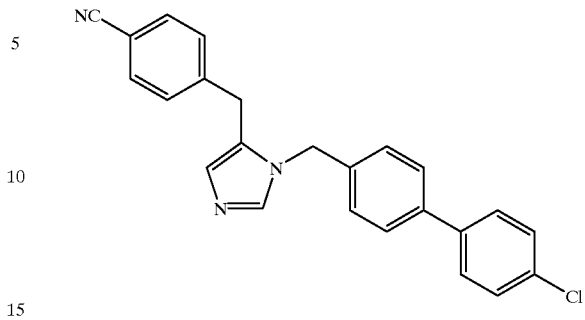

1-(4-(3',5'-dichloro)-biphenylmethyl)-5-(4-cyanobenzyl) imidazole

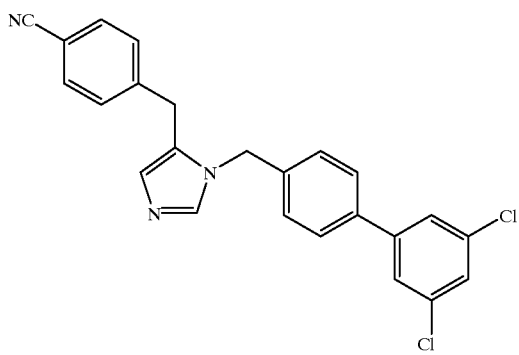

1-(2',5'-Dichloro-4-biphenylmethyl)-5-(4-cyanobenzyl) imidazole

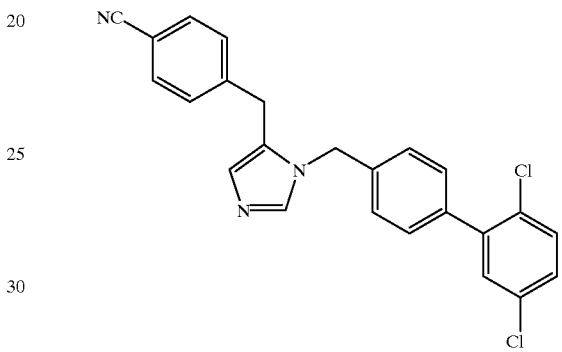

5-(2'-Methyl-4-biphenoxy)-1-(4-cyanobenzyl)-imidazole

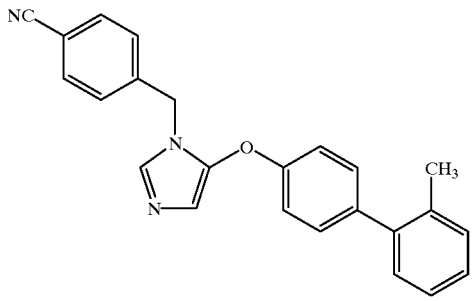

1-(3'-Methoxy-2-methyl-4-biphenylmethyl)-5-(4-cyanobenzyl)imidazole

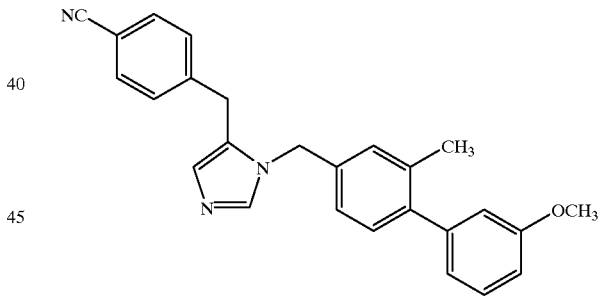

1-(4-Cyanobenzyl)-5-(1-hydroxy-1-(3-fluoro-4-biphenyl)-methyl)-imidazole

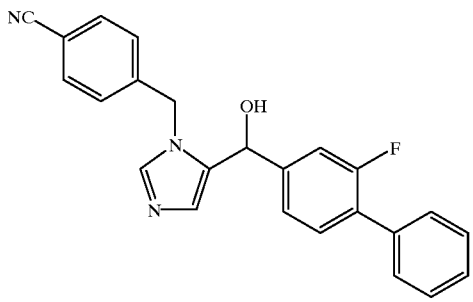

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^{1b}$ etc.) occurs more than one time in any constituent, its definition on each occurence is independent at every other occurence. Also, combinations of substituents/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aralkyl and aroyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, phthalimid-1-yl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^7$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substituents in addition to the point of attachment to the rest of the compound.

As used herein, when no specific substituents are set forth, the terms "substituted aryl", "substituted heterocycle" and "substituted cycloalkyl" are intended to include the cyclic group which is substituted on a substitutable ring carbon atom with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl$)O$—, —OH, $(C_1-C_6$ alkyl$)S(O)_m$—, $(C_1-C_6$ alkyl$)C(O)NH$—, $H_2N$—$C(NH)$—, $(C_1-C_6$ alkyl$)C(O)$—, $(C_1-C_6$ alkyl$)OC(O)$—, $N_3,(C_1-C_6$ alkyl$)OC(O)NH$—, phenyl, pyridyl, imidazolyl, oxazolyl, isoxazolyl, thiazolyl, thienyl, furyl, isothiazolyl and $C_1-C_{20}$ alkyl.

Lines drawn into the ring systems from substituents (such as from $R^2$, $R^3$, $R^4$ etc.) indicate that the indicated bond may be attached to any of the substitutable ring carbon atoms.

The substituent illustrated by the structure

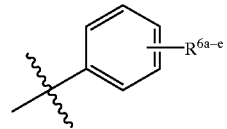

is a simplified representation of a phenyl ring having five (5) substituents (hydrogens and/or non-hydrogens) and may also be represented by the structure

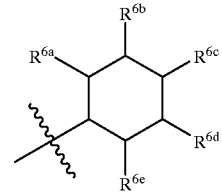

The moiety described as

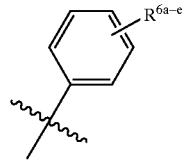

where any two of $R^{6a}$, $R^{6b}$, $R^{6c}$, $R^{6d}$ and $R^{6e}$ on adjacent carbon atoms are combined to form a diradical selected from —CH=CH—CH=CH, —CH=CH—CH—, —(CH$_2$)$_4$— and —(CH$_2$)$_4$— includes the following structures:

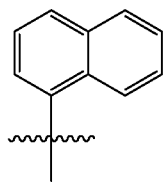 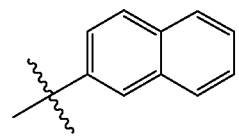

-continued

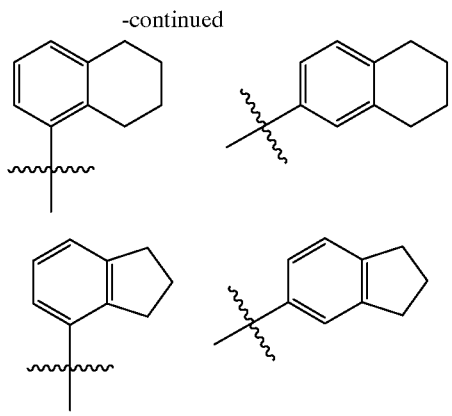

It is understood that such fused ring moieties may be further substituted by the remaining $R^{6a}$, $R^{6b}$, $R^{6c}$, $R^{6d}$ and/or $R^{6e}$ as defined hereinabove.

Preferably, $R^{1a}$ and $R^{1b}$ are independently selected from: hydrogen, $R^{11}C(O)O-$, $-N(R^{10})_2$, $R^{10}C(O)NR^{10}-$, $R^{10}O-$ or unsubstituted or substituted $C_1-C_6$ alkyl wherein the substituent on the substituted $C_1-C_6$ alkyl is selected from unsubstituted or substituted phenyl, $-N(R^{10})_2$, $R^{10}O-$ and $R^{10}C(O)NR^{10}-$.

Preferably, $R^2$ is selected from:
a) hydrogen,
b) $C_3-C_{10}$ cycloalkyl, halogen, $C_1-C_6$ perfluoroalkyl, $R^{12}O-$, CN, $NO_2$, $R^{10}C(O)-$ or $-N(R^{10})_2$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^{12}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, and $R^{11}OC(O)-NR^{10}-$.

Preferably, $R^3$ is selected from: hydrogen, halogen, trifluoromethyl, trifluoromethoxy and $C_1-C_6$ alkyl.

Preferably, $R^4$ and $R^5$ are hydrogen.

Preferably, $R^{6a}$, $R^{6b}$, $R^{6c}$, $R^{6d}$ and $R^{6e}$ are independently selected from:
a) hydrogen,
b) $C_3-C_{10}$ cycloalkyl, halogen, $C_1-C_6$ perfluoroalkyl, $R^{12}O-$, $R^{11}S(O)_m-$, CN, $NO_2$, $R^{10}C(O)-$ or $-N(R^{10})_2$,
c) unsubstituted $C_1-C_6$ alkyl;
d) substituted $C_1-C_6$ alkyl wherein the substituent on the substituted $C_1-C_6$ alkyl is selected from unsubstituted or substituted aryl, $C_3-C_{10}$ cycloalkyl, $R^{12}O-$, $R^{11}S(O)_m-$, $R^{10}C(O)-$ or $-N(R^{10})_2$; or any two of $R^{6a}$, $R^{6b}$, $R^{6c}$, $R^{6d}$ and $R^{6e}$ on adjacent carbon atoms are combined to form a diradical selected from $-CH=CH-CH=CH-$, $-CH=CH-CH_2-$, $-(CH_2)_4-$ and $-(CH_2)_3-$.

Preferably, $R^8$ is independently selected from:
a) hydrogen, and
b) aryl, substituted aryl, heterocycle, substituted heterocycle, $C_1-C_6$ perfluoroalkyl or CN.

Preferably, $R^9$ is hydrogen, halogen, $CF_3$ or methyl.

Preferably, $R^{10}$ is selected from H, $C_1-C_6$ alkyl and benzyl.

Preferably, $A^1$ and $A^2$ are independently selected from: a bond, $-C(O)NR^{10}-$, $-NR^{10}C(O)-$, O, $-N(R^{10})-$, $-S(O)_2N(R^{10})-$ and $-N(R^{10})S(O)_2-$.

Preferably, V is selected from hydrogen, heterocycle and aryl. More preferably, V is phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, X is a bond, $-NR^{10}C(O)-$, O or $-C(=O)-$. Most preferably, X is a bond.

Preferably, n and r are independently 0, 1, or 2.

Preferably s is 0.

Preferably t is 1.

Preferably, the moiety

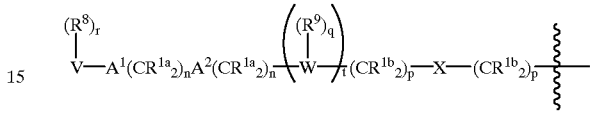

is selected from:

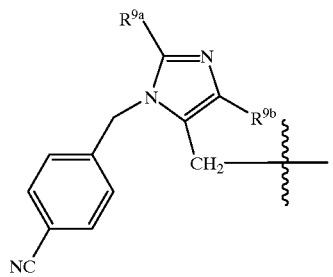

and

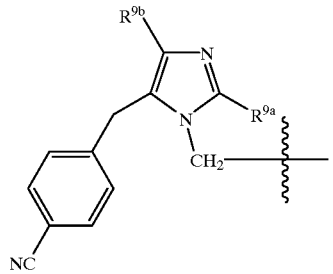

It is intended that the definition of any substituent or variable (e.g., $R^{1a}$, $R^9$, n, etc.) at a particular location in a molecule be independent of its definitions elsewhere in that molecule. Thus, $-N(R^{10})_2$ represents $-NHH$, $-NHCH_3$, $-NHC_2H_5$, etc. It is understood that substituents and substitution patterns on the compounds of the instant invention can be selected by one of ordinary skill in the art to provide compounds that are chemically stable and that can be synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–22, in addition to other standard manipulations such as ester hydrolysis, cleavage of protecting groups, etc., as may be known in the literature or exemplified in the experimental procedures. Substituents $R^2$, $R^6$ and $R^8$, as shown in the Schemes, represent the substituents $R^2$, $R^3$, $R^4$, $R^5$, $R^{6a}$, $R^{6b}$, $R^{6c}$, $R^{6d}$ and $R^8$; although only one such $R^2$, $R^6$ or $R^8$ is present in the intermediates and products of the schemes, it is understood that the reactions shown are also applicable when such aryl or heteroaryl moieties contain multiple substituents.

These reactions may be employed in a linear sequence to provide the compounds of the invention or they may be used to synthesize fragments which are subsequently joined by the alkylation reactions described in the Schemes. Aryl-aryl coupling is generally described in "Comprehensive Organic Functional Group Transformations," Katritsky et al. eds., pp 472–473, Pergamon Press (1995).

Synopsis of Schemes 1–22:

The requisite intermediates are in some cases commercially available, or can be prepared according to literature procedures, for the most part. Schemes 1–13 illustrate synthesis of the instant biaryl compound which incorporate a preferred benzylimidazolyl sidechain. Thus, in Scheme 1, for example, a biaryl intermediate that is not commercially available may be synthesized by methods known in the art. Thus, a suitably substituted phenyl boronic acid I may be reacted under Suzuki coupling conditions (*Pure Appl. Chem.*, 63:419 (1991)) with a suitably substituted halogenated benzoic acid, such as 4-bromobenzoic acid, to provide the biaryl carboxylic acid II. The acid may be reduced and the triflate of the intermediate alcohol III may be formed in situ and coupled to a suitably substituted benzylimidazolyl IV to provide, after deprotection, the instant compound V.

Schemes 2–5 illustrate other methods of synthesizing the key alcohol intermediates, which can then be processed as described in Scheme 1. Thus, Scheme 2 illustrates the analogous series of biaryl alcohol forming reactions starting with the halogenated biarylaldehyde.

Scheme 3 illustrates the reaction wherein the "terminal" phenyl moiety is employed in the Suzuki coupling as the halogenated reactant. Such a coupling reaction is also compatible when one of the reactants incorporates a suitably protected hydroxyl functionality as illustrated in Scheme 4.

Negishi chemistry (i Org. Synth., 66:67 (1988)) may also be employed to form the biaryl component of the instant compounds, as shown in Scheme 5. Thus, a suitably substituted zinc bromide adduct may be coupled to a suitably substituted aryl halide in the presence of nickel (II) to provide the biheteroaryl VII. The aryl halide and the zinc bromide adduct may be selected based on the availability of the starting reagents.

Scheme 6 illustrates the preparation of a suitably substituted biphenylmethyl bromide which could also be utilized in the reaction with the protected imidazole as described in Scheme 1.

Preparation of biaryl intermediates having a suitably substituted alkyl moiety on the carbon adjacent to the eventual point of attachment to the rest of the instant compounds is illustrated in Scheme 6a. Thus a suitably substituted biaryl carboxylic acid is first converted to the amide and then the phenyl lithium is prepared and reacted in situ with a suitably substituted alkanal to provide the hydroxyalkane side-chain. The amide is then converted sequentially to the hydroxymethylbiaryl IIIa or bromomethylbiaryl intermediates which may then be utilized in reactions that have been previously described or will be described below.

As illustrated in Scheme 7, the sequence of coupling reactions may be modified such that the biphenyl bond is formed last. Thus, a suitably substituted imidazole may first be alkylated with a suitably substituted benzyl halide to provide intermediate VIII. Intermediate VIII can then undergo Suzuki type coupling to a suitably substituted phenyl boronic acid.

Scheme 8 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 9 illustrates synthesis of instant compounds that incorporate a preferred imidazolyl moiety connected to the biaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated biaryl moieties to provide the instant compounds shown.

Compounds of the instant invention wherein the $A^1(CR^{1a}2)_nA^2(CR^{1a}2)_n$ linker is oxygen may be synthesized by methods known in the art, for example as shown in Scheme 10. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 11 illustrates an analogous series of reactions wherein the $(CR^{1b}2)_pX(CR^{1b}2)p$ linker of the instant compounds is oxygen. Thus, a suitably substituted haloaryl alcohol, such as, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a second aryl moiety by Suzuki chemistry to provide the instant compound.

Compounds of the instant invention wherein the $A^1(CR^{1a}2)_nA^2(CR^{1a}2)_n$ linker is a substituted methylene may be synthesized by the methods shown in Scheme 12. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 1) provides the instant compound XX. If other $R^1$ substituents are desired, the acetyl moiety can be manipulated as illustrated in the Scheme.

Grignard chemistry may also be employed to form a substituted alkyl linker between the biaryl and the preferred W (imidazolyl) as shown in Scheme 13. Similar substituent manipulation as shown in Scheme 12 may be performed on the fully functionalized compound which incorporates an $R^{1b}$ hydroxyl moiety.
SCHEME 1
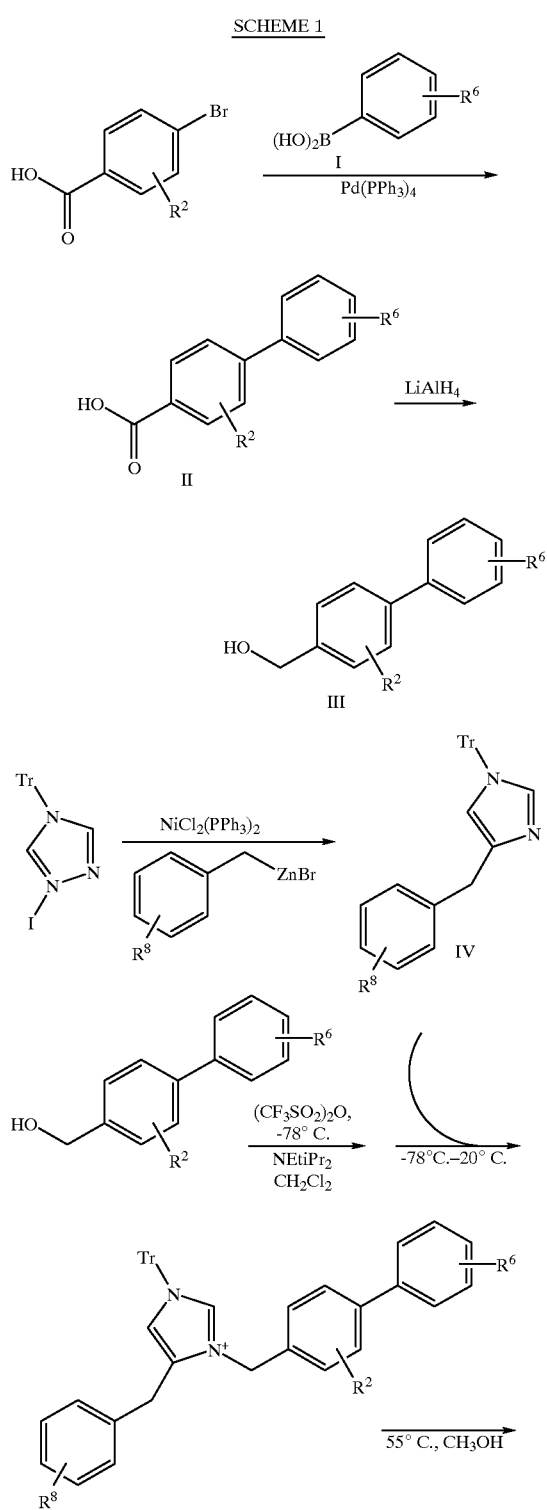
SCHEME 2
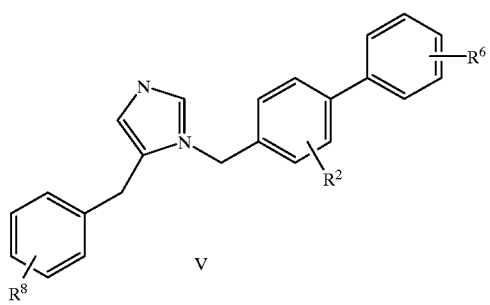
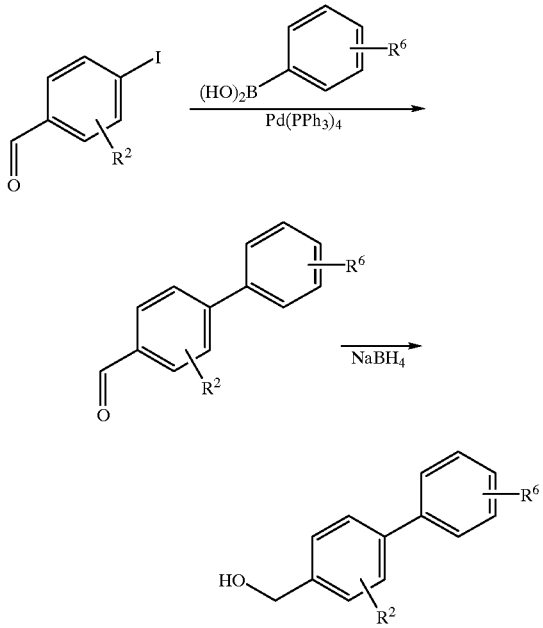
SCHEME 3
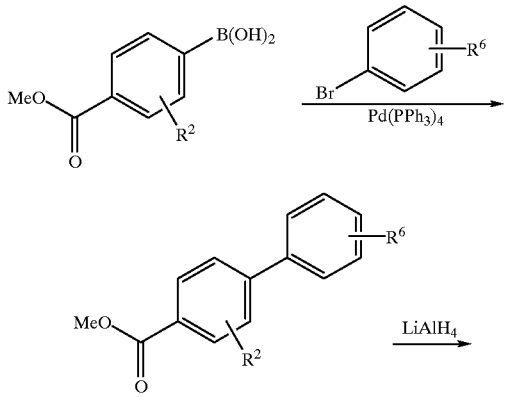

31
-continued
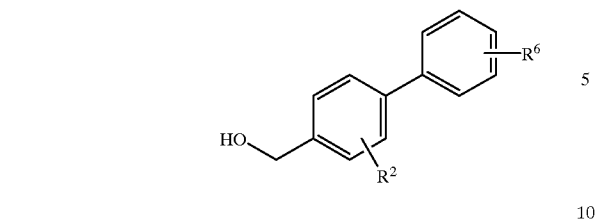
SCHEME 4
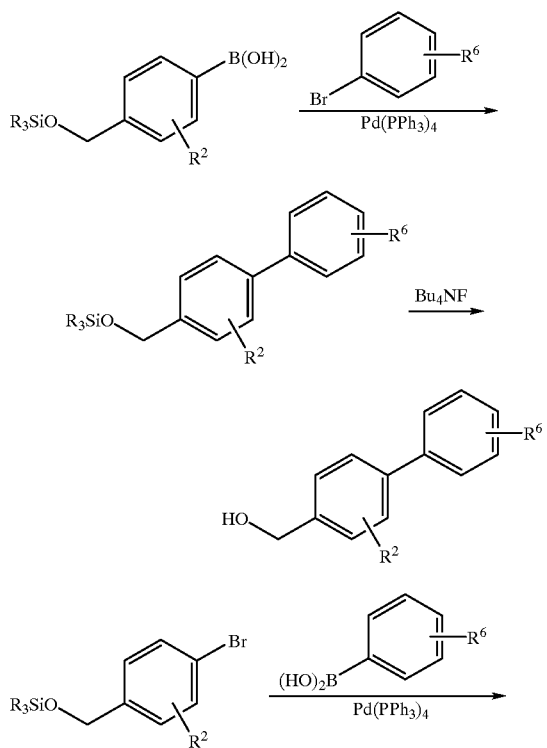
SCHEME 5
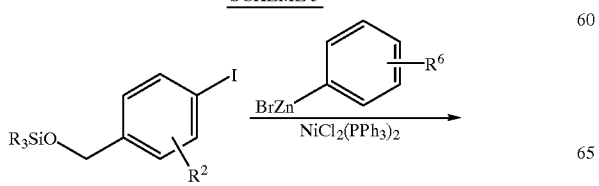
32
-continued
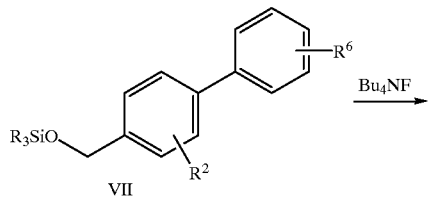
VII
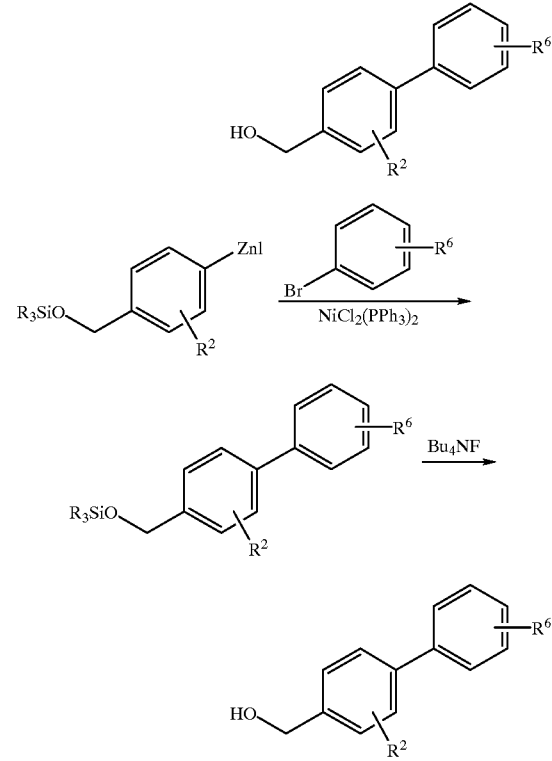
SCHEME 6
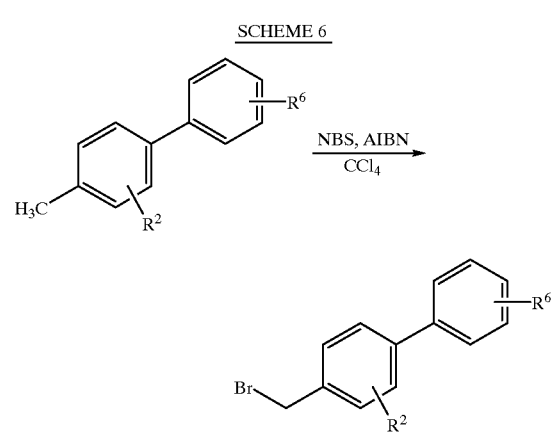

33
SCHEME 6a
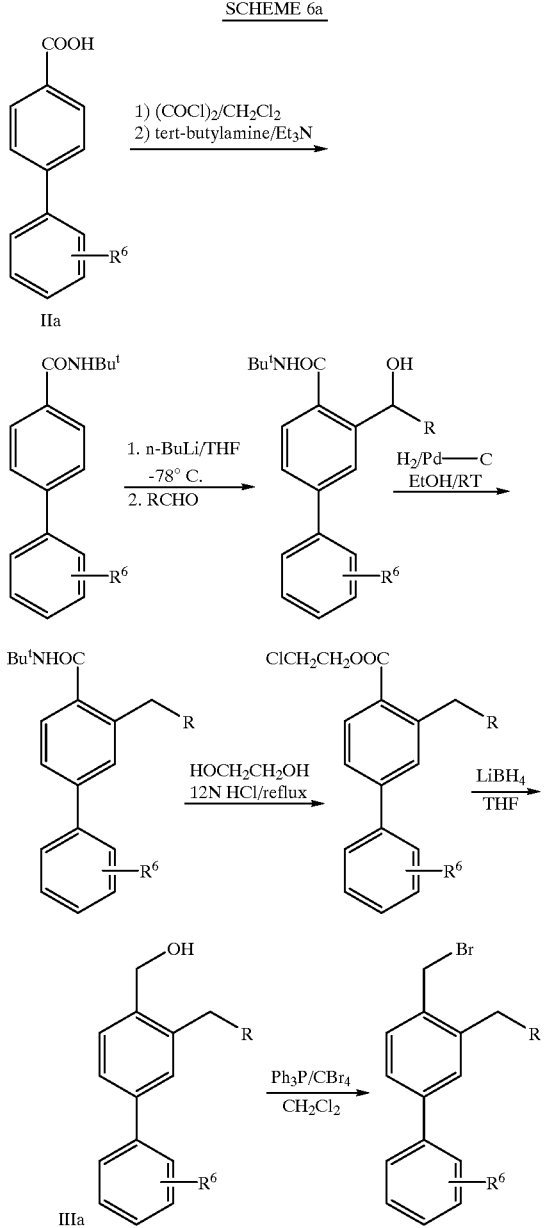
SCHEME 7
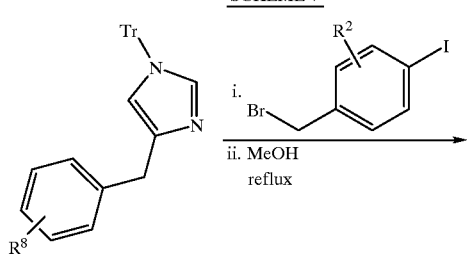
34
-continued
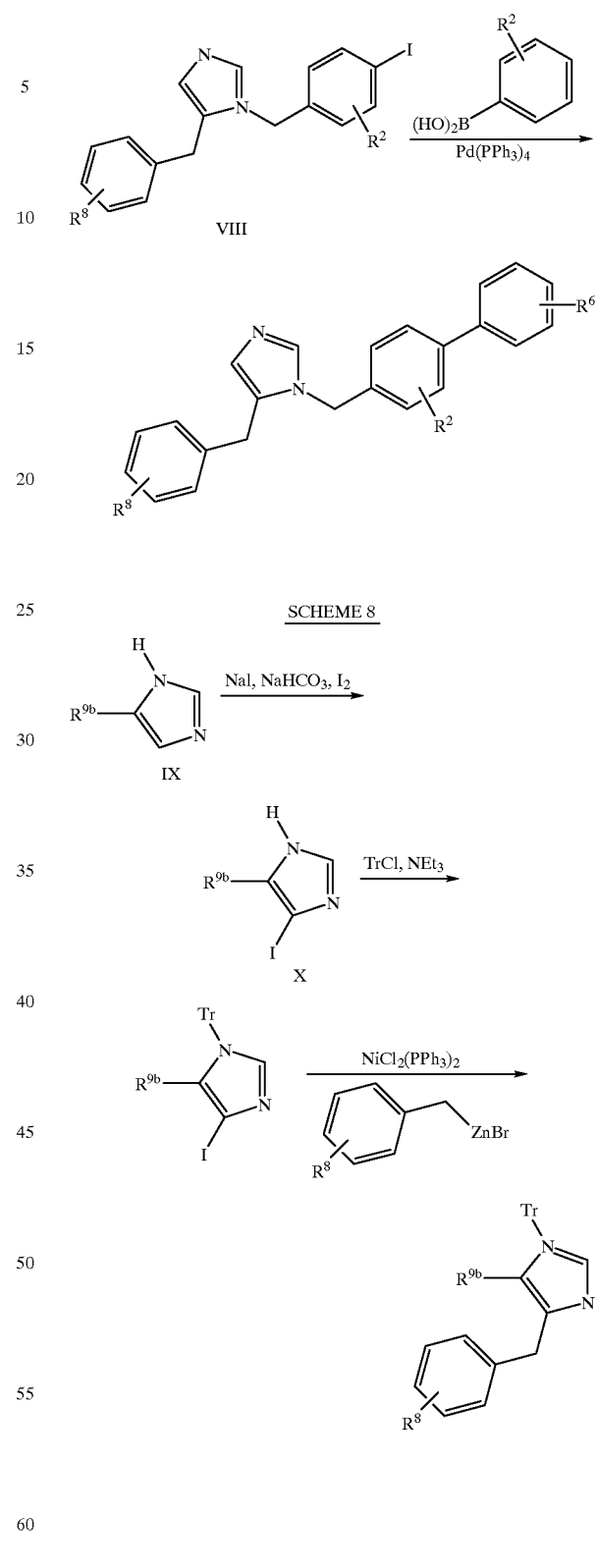
SCHEME 8

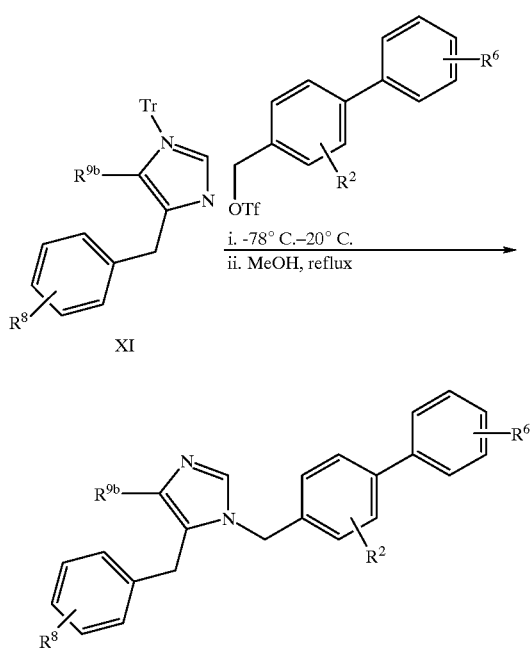
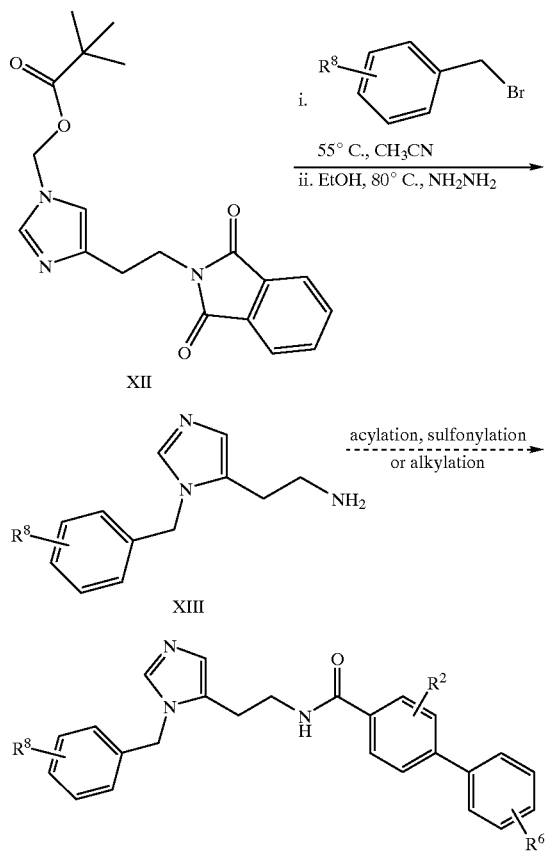
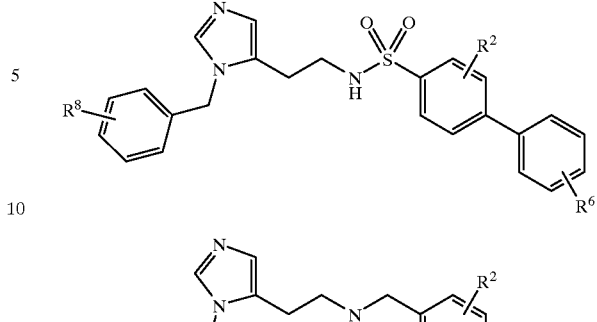
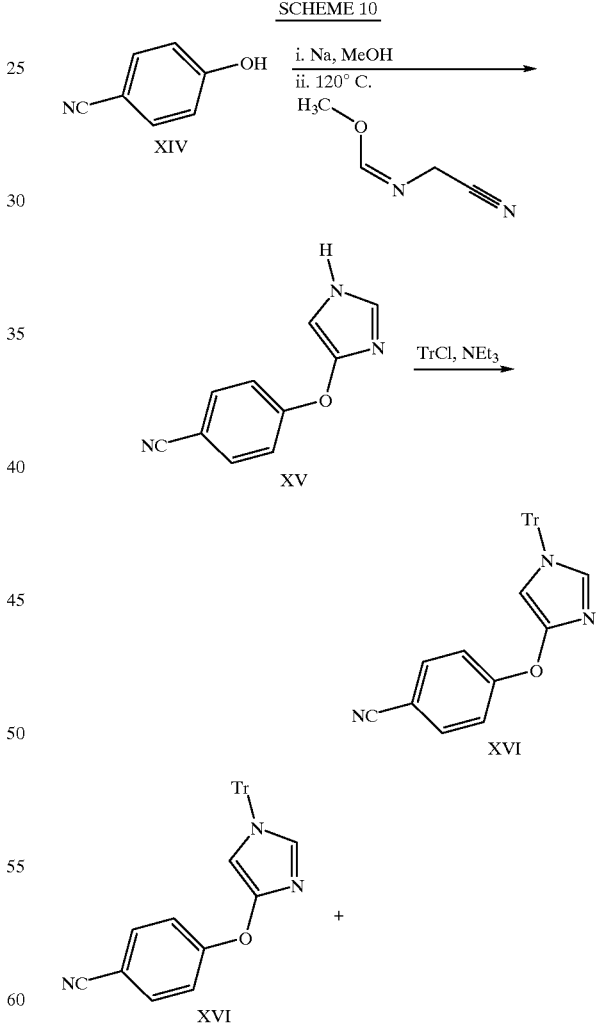

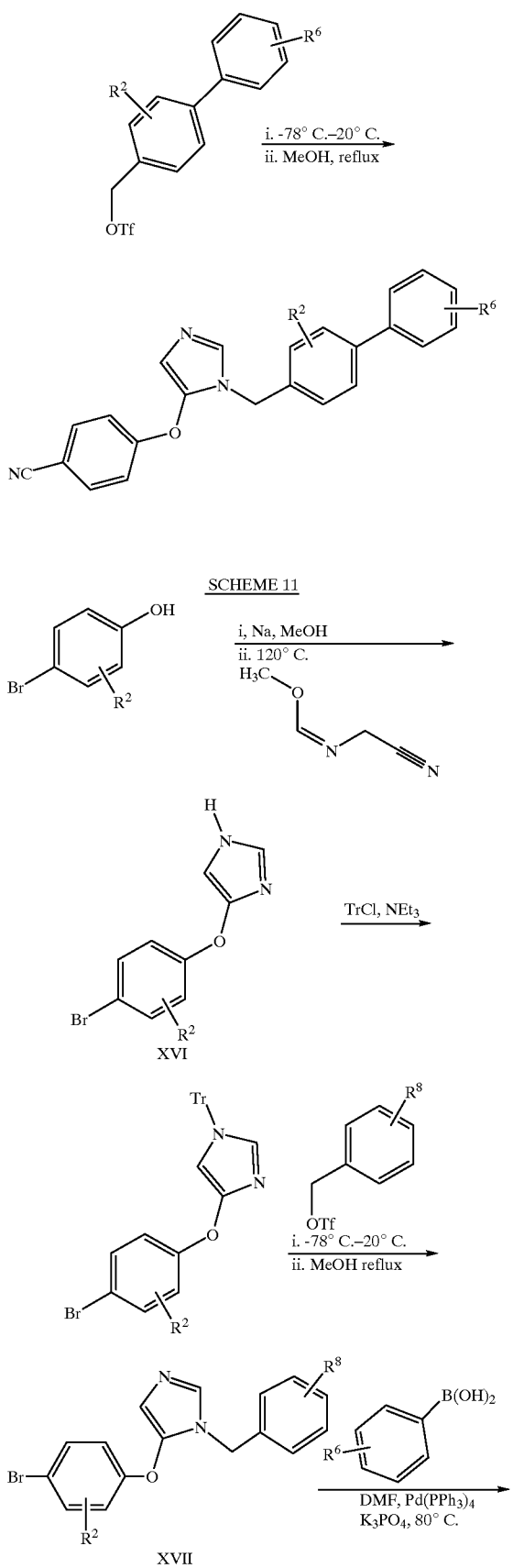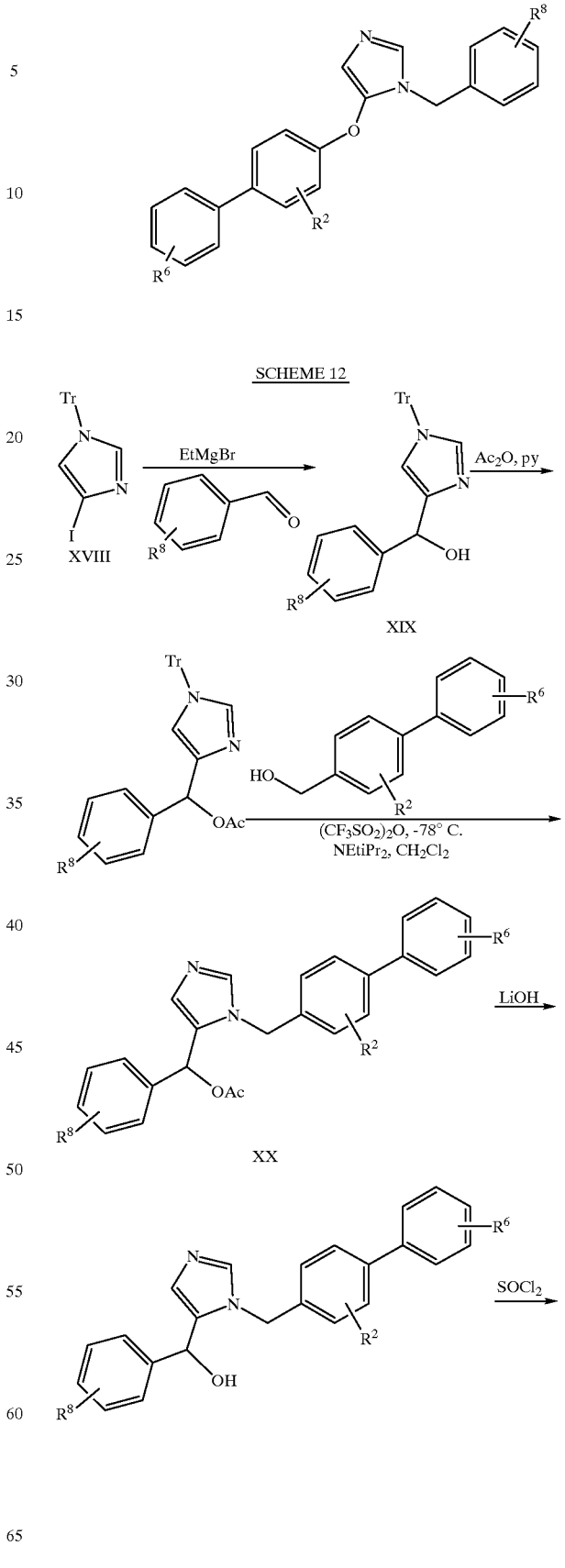

-continued

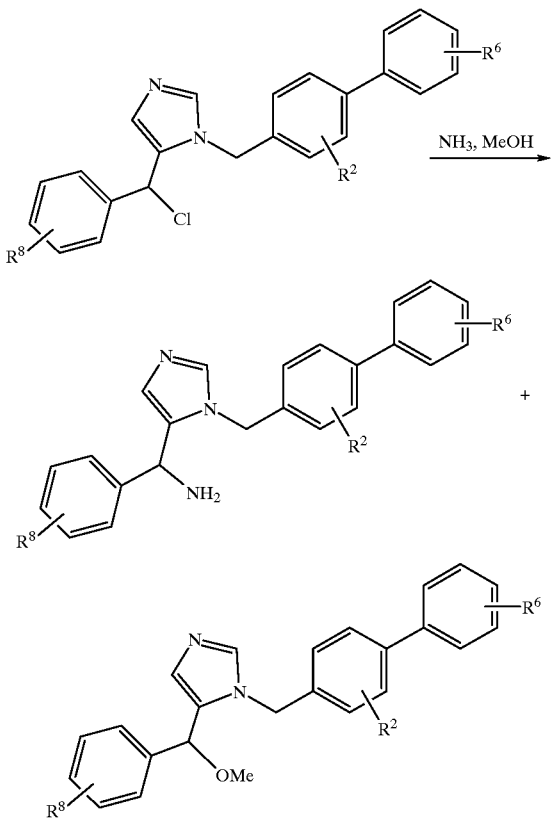

SCHEME 13

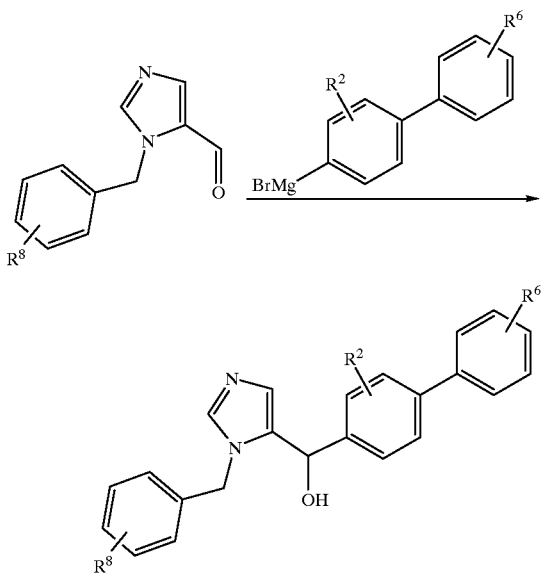

Schemes 16–20 illustrate reactions wherein the moiety

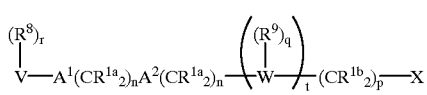

incorporated in the compounds of the instant invention is represented by other than a substituted imidazole-containing group.

Thus, the intermediates whose synthesis are illustrated in Schemes hereinabove and other biheteroaryl intermediates obtained commercially or readily synthesized, can be coupled with a variety of aldehydes. The aldehydes can be prepared by standard procedures, such as that described by O. P. Goel, U. Krolls, M. Stier and S. Kesten in i Organic Syntheses, 1988, 67, 69–75, from the appropriate amino acid (Scheme 14). Grignard chemistry may be utilized, as shown in Scheme 14, to incorporate the biaryl moiety. Thus, a suitably substituted biaryl Grignard reagent is reacted with an aldehyde to provide the C-alkylated instant compound XXI. Compound XXI can be deoxygenated by methods known in the art, such as a catalytic hydrogention, then deprotected with trifluoroacetic acid in methylene chloride to give the final compound XXII. The final product XXII may be isolated in the salt form, for example, as a trifluoroacetate, hydrochloride or acetate salt, among others. The product diamine XXII can further be selectively protected to obtain XXIII, which can subsequently be reductively alkylated with a second aldehyde to obtain XXIV. Removal of the protecting group, and conversion to cyclized products such as the dihydroimidazole XXV can be accomplished by literature procedures.

If the biaryl subunit reagent is reacted with an aldehyde which also has a protected hydroxyl group, such as XXVI in Scheme 15, the protecting groups can be subsequently removed to unmask the hydroxyl group (Schemes 15, 16). The alcohol can be oxidized under standard conditions to e.g. an aldehyde, which can then be reacted with a variety of organometallic reagents such as Grignard reagents, to obtain secondary alcohols such as XXX. In addition, the fully deprotected amino alcohol XXXI can be reductively alkylated (under conditions described previously) with a variety of aldehydes to obtain secondary amines, such as XXXII (Scheme 16), or tertiary amines.

The Boc protected amino alcohol XXVIII can also be utilized to synthesize 2-aziridinylmethylbiaryl such as XXXIII (Scheme 17). Treating XXVIII with, 1,1'-sulfonyldiimidazole and sodium hydride in a solvent such as dimethylformamide led to the formation of aziridine XXXIII. The aziridine is reacted with a nucleophile, such as a thiol, in the presence of base to yield the ring-opened product XXXIV.

In addition, the biaryl subunit reagent can be reacted with aldehydes derived from amino acids such as O-alkylated tyrosines, according to standard procedures, to obtain compounds such as XL, as shown in Scheme 18. When R' is an aryl group, XL can first be hydrogenated to unmask the phenol, and the amine group deprotected with acid to produce XLI. Alternatively, the amine protecting group in XL can be removed, and O-alkylated phenolic amines such as XLII produced.

Schemes 19–22 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

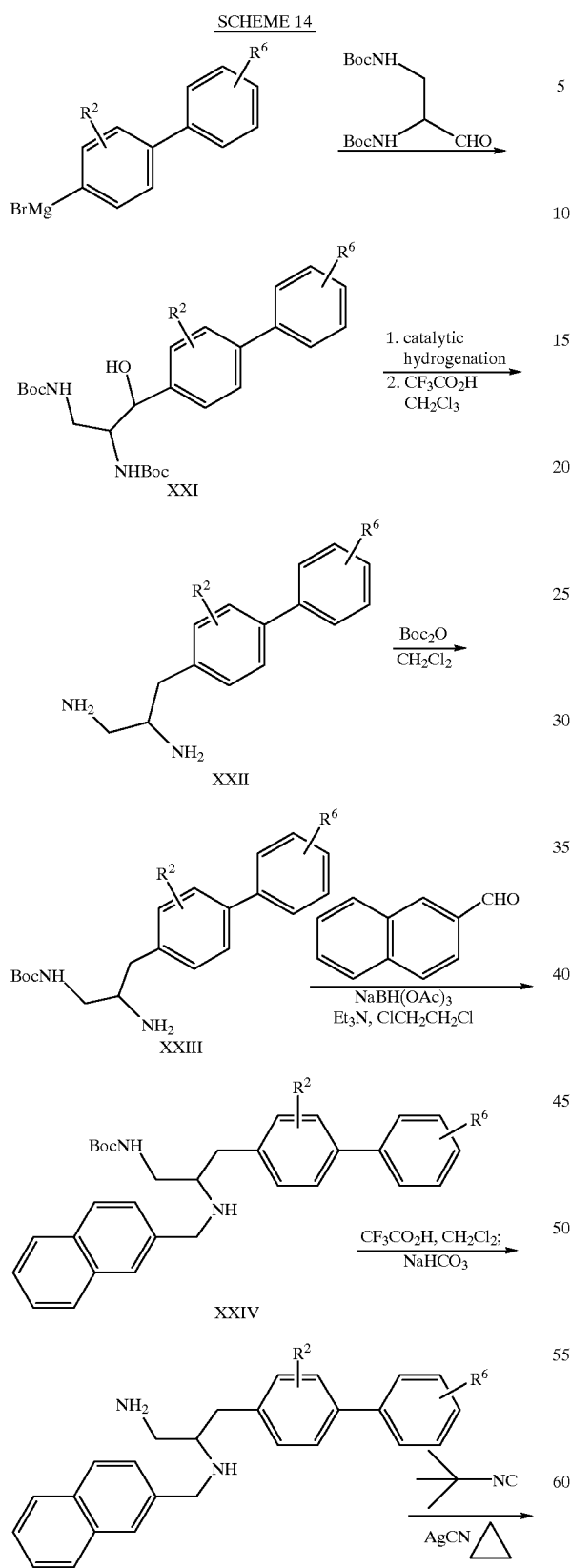
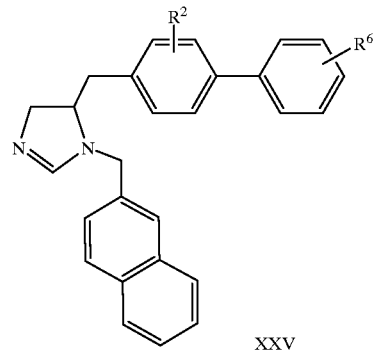
SCHEME 14
SCHEME 15

SCHEME 16
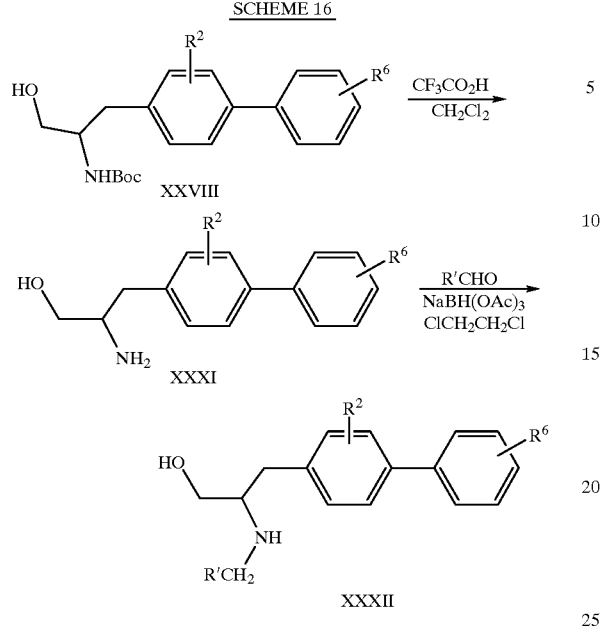
SCHEME 17
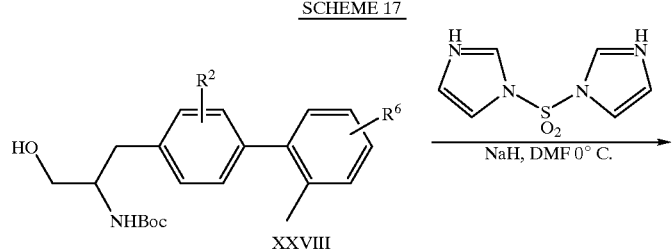
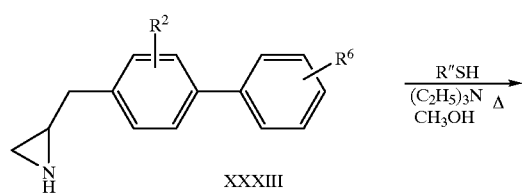
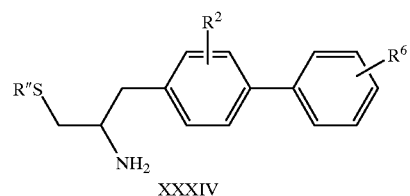

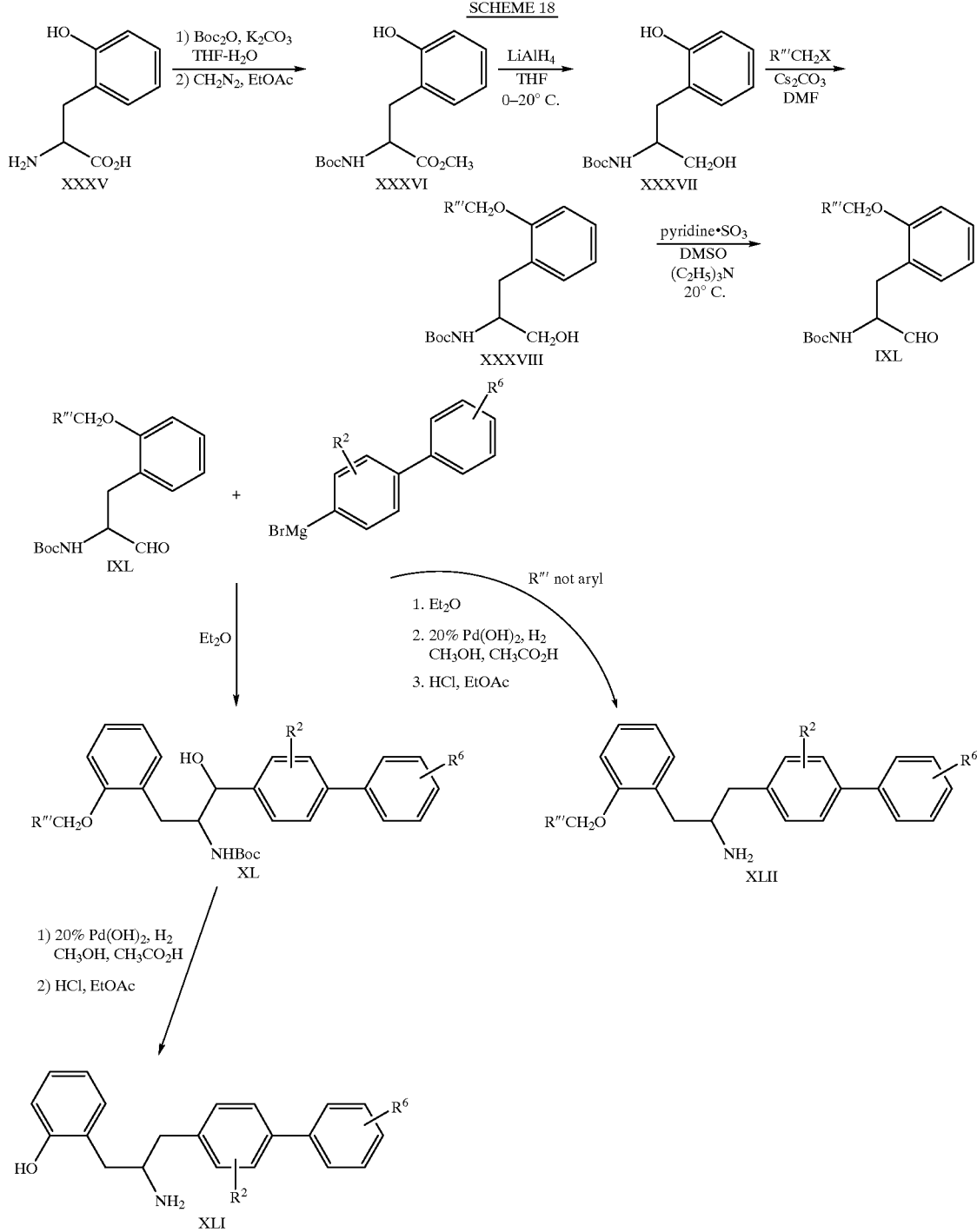

-continued
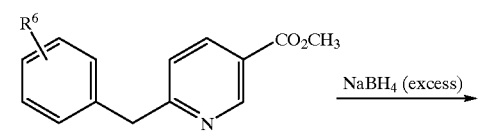
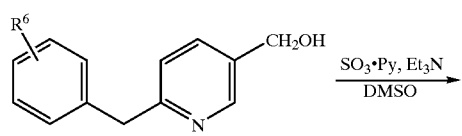
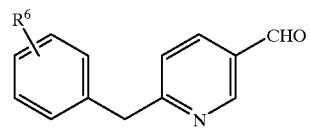
SCHEME 20
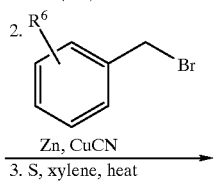
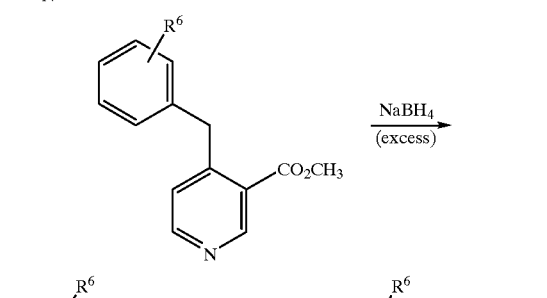
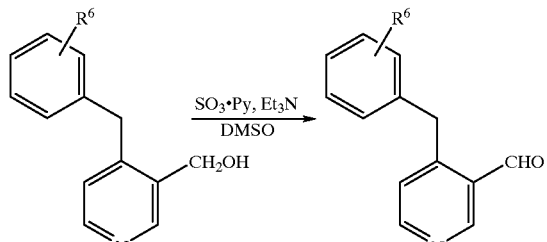
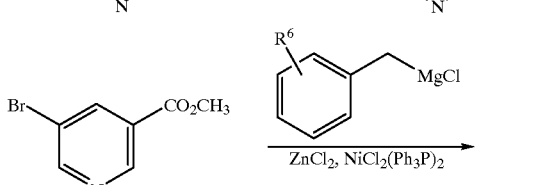
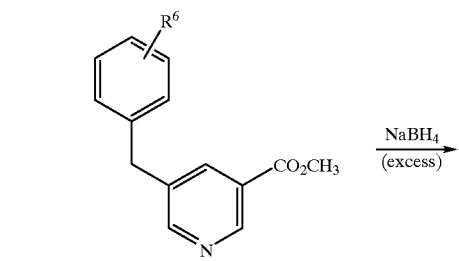
-continued
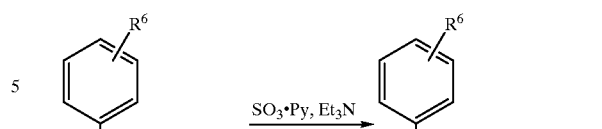
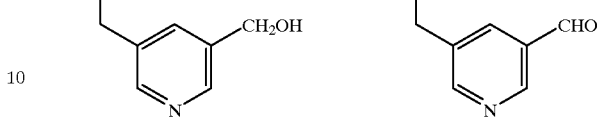
SCHEME 21
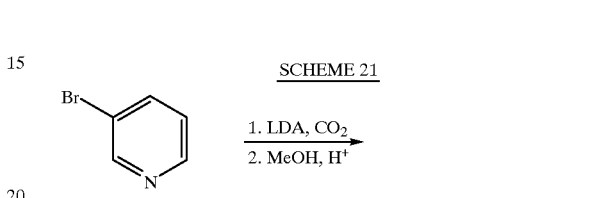
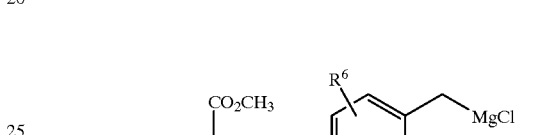
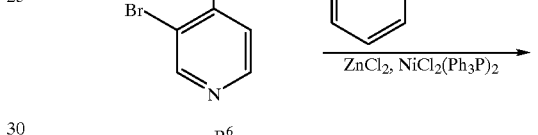
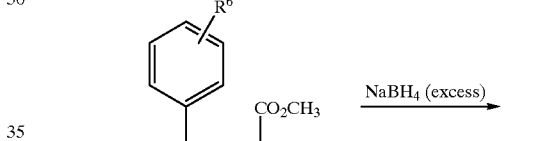
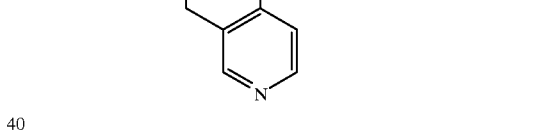
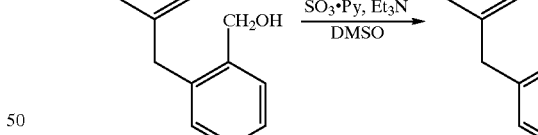
SCHEME 22
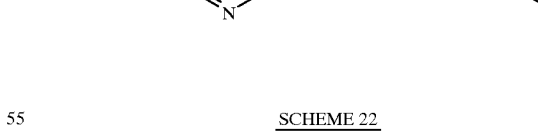
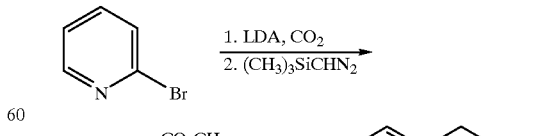
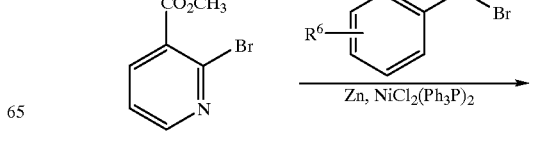

-continued

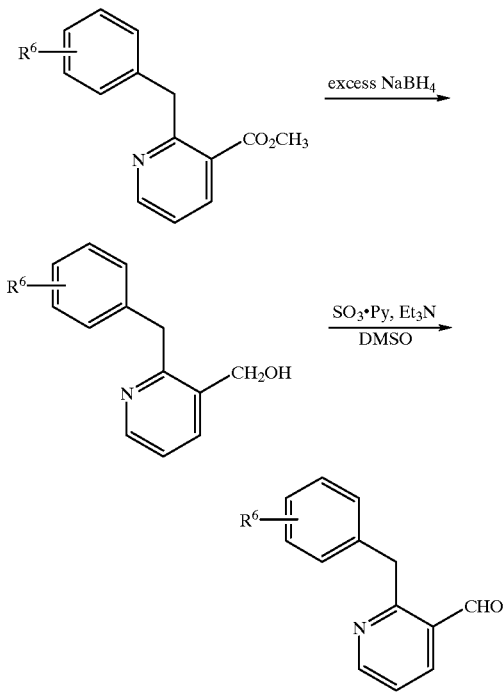

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scI, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. i *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If fomulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for a sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

1-(4-Biphenylmethyl)-5-(4-cyanobenzyl)imidazole hydrochloride salt

Step A: 1-Trityl-4-(4-cyanobenzyl)-imidazole

To a suspension of activated zinc dust (3.57 g, 54.98 mmol) in THF (50 mL) was added dibromoethane (0.315 mL, 3.60 mmol) and the reaction stirred under argon for 45 minutes, at 20° C. The suspension was cooled to 0° C. and a-bromo-p-tolunitrile (9.33 g, 47.6 mmol) in THF (100 mL) was added dropwise over a period of 10 minutes. The reaction was then allowed to stir at 20° C. for 6 hours and bis(triphenylphosphine)Nickel II chloride (2.40 g, 3.64 mmol) and 4-iodo-1-tritylimidazole (15.95 g, 36.6 mmol, S. V. Ley, et al., J. Org. Chem. 56, 5739 (1991)) were added in one portion. The resulting mixture was stirred 16 hours at 20° C. and then quenched by addition of saturated $NH_4Cl$ solution (100 mL) and the mixture stirred for 2 hours. Saturated aq. $NaHCO_3$ solution was added to give a pH of 8 and the solution was extracted with EtOAc (2×250 mL), dried ($MgSO_4$) and the solvent evaporated in vacuo. The residue was chromatographed (Silica gel, 0–20% EtOAc in $CH_2Cl_2$) to afford the title compound as a white solid.

$^1$H NMR ($CDCl_3$, 400 Mz) δ (7.54 (2H, d, J=7.9 Hz), 7.38(1H, s), 7.36–7.29 (11H, m), 7.15–7.09(6H, m), 6.58 (1H, s) and 3.93(2H, s) ppm.

Step B: 1-(4-Biphenylmethyl)-5-(4-cyanobenzyl)imidazole hydochloride salt

To 1-trityl-4-(4-Cyanobenzyl)-imidazole (608 mg, 1.43 mmol) in acetonitrile (2 mL) was added 4-chloromethylbiphenyl (290 mg, 1.43 mmol) and the mixture heated at 55° C. for 16 hours. The residue was dissolved in methanol (30 ml) and heated at reflux for 20 minutes, cooled and evaporated to dryness. The residue was partitioned between sat. aq. $NaHCO_3$ solution and $CH_2C_{12}$. The organic layer was dried, ($MgSO_4$) and the solvent evaporated in vacuo. The residue was chromatographed (Silica gel, 5% MeOH in $CH_2Cl_2$) to afford the imidazole which was converted to the HCl salt by treatment with one equivalent of HCl in aqueous acetonitrile. Evaporation of solvent in vacuo afforded the title compound as a white powder.

Anal. Calcd for $C_{24}H_{19}N_3$•1.00 HCl: C, 74.70; H, 5.22; N, 10.89. Found: C, 74.70; H, 5.31; N, 10.77. FAB MS 350 ($MH^+$); $^1$H NMR $CD_3OD$ δ 9.03(1H, s), 7.65–7.50(5H, m), 7.44(2H, t, J=7.5 Hz), 7.39(1H, s), 7.35(1H, t, J=7.3 Hz), 7.26(2H, d, J=8.1 Hz), 7.20(2H, d, J=8.1 Hz), 5.42(2H, s) and 4.17(2H, s) ppm.

Example 2

1-(2-Biphenylmethyl)-5-(4-cyanobenzyl)imidazole hydrochloride salt

To 1-trityl-4-(4-cyanobenzyl)-imidazole (250 mg, 0.588 mmol) in acetonitrile (1 mL) was added 2(bromomethyl)biphenyl (0.108 mL, 0.591 mmol) and the mixture heated at 55° C. for 16 hours. The solvent was evaporated in vacuo. The residue was dissolved in methanol (10 mL) and heated at reflux for 30 minutes, cooled and the solvent evaporated in vacuo. The residue was partitioned between sat. aq. $NaHCO_3$ solution and $CH_2Cl_2$. The organic layer was dried, ($NaSO_4$) and the solvent evaporated in vacuo. The residue was chromatographed (silica gel, 3% MeOH in $CH_2Cl_2$) to afford the imidazole, which was converted to the HCl salt by treatment with one equivalent of HCl in aqueous acetonitrile. Evaporation of solvent in vacuo afforded the title compound as a white solid.

Anal. Calcd. for $C_{24}H_{19}N_3$•1.00HCl: C, 74.70; H, 5.22; N, 10.89. Found: C, 74.60; H, 5.26; N, 10.97. FAB MS 350 ($MH^+$); $^1$H NMR ($CD_3OD$, 400 MHz) δ 8.39(1H, s), 7.59 (2H, d, J=8.4 Hz), 7.48(1H, t, J=6.5 Hz), 7.46–7.36(3H, m), 7.30(1H, d, J=6.6 Hz), 7.28–7.18(3H, m), 7.13(2H, d, J=8.1 Hz), 5.31(2H, s) and 3.78(2H, s) ppm.

Example 3

1-(3-Biphenylmethyl)-5-(4-cyanobenzyl)imidazole trifluoroacetate salt

Step A: 3-(Bromomethyl)biphenyl

To a solution of 3-phenyltoluene (1.80 mL, 10.9 mmol) in carbon tetrachloride (50 mL) was added N-bromosuccinimide (2.124 g, 11.93 mmol) and the mixture heated to 70° C. AIBN (50 mg, 0.30 mmol) was added and the mixture refluxed for 30 mins. Additional AIBN was added (50 mg, 0.30 mmol) and the mixture refluxed for 16 hours. The reaction was cooled, filtered, and the solvent evaporated in vacuo. The residue was chromatographed (Silica gel, 5% EtOAc in hexanes) to afford the title compound as a white solid.

Step B: 1-(3-Biphenylmethyl)-5-(4-cyanobenzyl)imidazole trifluoroacetate salt

To 1-trityl-4-(4-cyanobenzyl)-imidazole (251 mg, 0.590 mmol) in acetonitrile (1 mL) was added 3-(bromomethyl)biphenyl (145 mg, 0.587 mmol) and the mixture heated at 55° C. for 16 hours. The residue was dissolved in methanol (10 mL) and heated at reflux for 30 minutes, cooled and evaporated to dryness. The residue was partitioned between sat. aq. $NaHCO_3$ solution and $CH_2Cl_2$. The organic layer was dried, ($NaSO_4$) and the solvent evaporated in vacuo. The residue was chromatographed (Silica gel, 2–5% MeOH in $CH_2Cl_2$) and further purified by preparative HPLC, (gradient elution, 95:5 to 5:95% water:acetonitrile containing 0.1% trifluoroacetic acid) to afford the title compound.

Anal. Calcd. for $C_{24}H_{19}N_3 \cdot 1.10 \ C_2HO_2F_3 \cdot 0.65 \ H_2O$: C, 64.68; H, 4.43; N, 8.64. Found: C, 64.68; H, 4.43; N, 8.50. FAB MS 350 (MH$^+$); $^1$H NMR (CD$_3$OD, 400 MHz) δ 9.05(1H, d, J=1.6 Hz), ), 7.58(1H, d, J=7.6 Hz), 7.55–7.48 (4H, m), 7.48–7.32(5H, m), 7.29(1H, s), 7.24(2H, d, 8.1 Hz), 7.13(1H, dd, J=7.7 and 0.8 Hz), 5.46(2H, s) and 4.20(2H, s) ppm.

Example 4

1-(4-Cyanobenzyl)-5-(4'-phenylbenzamido)ethylimidazole

Step A: 1-(4-Cyanobenzyl)-5-aminoethylimidazole $N^G$-pivaloyloxymethyl-$N^\alpha$-phthaloylhistamine$^1$ (4.55 g, 12.8 mmol) and a-bromo-p-tolunitrile (3.77 g, 19.2 mmol) were dissolved in acetonitrile (70 mL) and heated at 55° C. for 4 hours, cooled to room temperature, filtered and the imidazolium salt retained as a white solid. The filtrate was evaporated in vacuo to a volume of 30 mL and heated at 55° C. for 16 hours. The solution was cooled and the white solid collected by filtration. The solids were combined, and dissolved in ethanol (50 mL). Hydrazine (0.287 mL, 9.06 mmol) was added and the mixture heated at reflux for 16 hours. Dimethyl phthalate (2.22 mL, 13.57 mmol) was added and reflux was continued for 6 hours. The reaction mixture was cooled to 0° C., the solid was removed by filtration, concentrated to dryness, and the residue chromatographed (Silica gel, 3% $CH_2Cl_2$ then 8% $NH_4OH$ in $CH_3OH$) to afford the title compound.

$^1$H NMR (CD$_3$OD, 400 MHz) δ 7.76 (1H, s), 7.74 (2H, d, J=8 Hz), ), 7.27 (2H, d, J=8 Hz), 6.88 (1H, s), 5.35 (2H, s), 2.76 (2H, t, J=6 Hz) and 2.60(2H, t, J=6 Hz) ppm. 1. C. Emmett, F. H. Holloway, and J. L. Turner, *J. Chem. Soc., Perkin Trans.* 1, 1341, (1979))

Step B: 1-(4-Cyanobenzyl)-5-(4'-phenylbenzamido)ethylimidazole

To a solution of 1-(4-cyanobenzyl)-5-aminoethylimidazole (107 mg, 0.358 mmol), 4-phenylbenzoic acid (70.9 mg, 0.358 mmol), 3-hydroxy-1,2,3-benzotriazin-4(3H)-one, (72.6 mg, 0.445 mmol) and triethylamine (0.215 mL, 1.54 mmol) in DMF (4.0 mL) was added 1-(3-dimethylaminopropyl)-3-ethylcarbodiimide hydrochloride, EDC, (83.3 mg, 0.435 mmol) and the mixture stirred for 16 hours at ambient temperature. The reaction was partitioned between sat. aq. $NaHCO_3$ solution and EtOAc. The organic layer was dried, ($Na_2SO_4$) and the solvent evaporated in vacuo. The residue was chromatographed (Silica gel, 5% MeOH in $CH_2Cl_2$) to afford the imidazole which was converted to the HCl salt by treatment with one equivalent of HCl in aqueous acetonitrile. Evaporation of the solvent in vacuo afforded the title compound as a white solid.

Anal. Calcd. for $C_{26}H_{22}N_4O \cdot 1.00 \ HCl \cdot 0.95 \ H_2O$: C, 67.88; H, 5.46; N, 12.18. Found: C, 67.83; H, 5.47; N, 11.97. FAB MS 407 (MH$^+$); $^1$H NMR (CD$_3$OD, 400 MHz) δ 9.00(1H, s),), 8.67(1H, m), 7.90–7.60(8H, m),7.58–7.30(6H, m), 5.65(2H, s), 3.65(2H, t, J=5.4 Hz) and 2.95(2H, t, J=6.4 Hz) ppm.

Example 5

1-(2'-Trifluoromethyl-4-biphenylmethyl)-5-(4-cyanobenzyl)imidazole hydrochloride salt Step A: 4-(2-trifluoromethylphenyl)benzoic acid To a solution of 4-carboxybenzeneboronic acid (1.218 g, 7.340 mmol) and $Na_2CO_3$ (2.40 g, 22.6 mmol) in water (75 mL) was added p-dioxane (75 mL). This mixture was treated sequentially with 2-iodobenzotrifluoride (1.05 mL, 7.48 mmol) and palladium (II) acetate (151 mg, 0.673 mmol) and allowed to stir at ambient temperature for 16 hours. The solvent was evaporated in vacuo. To the residue was added EtOAc (400 mL) and water (300 mL). The aqueous layer was acidified to pH 1 with 1.0 N aq. HCl and the layers separated. The aqueous layer was extracted with EtOAc (2×200 mL). The organic extracts were combined, washed with brine (200 mL), 5% aq. $Na_2S_2O_3$ (200 mL), saturated NaCl (200 mL), dried ($Na_2SO_4$), and the solvent evaporated in vacuo to afford the title compound as a yellow solid. $^1$H NMR (CDCl$_3$, 400 MHz) d 8.14(2H, d, J=8.1 Hz), ), 7.77(1H, d, J=7.9 Hz), 7.60(1H, t, J=7.5 Hz), 7.52(1H, t, J=7.3 Hz), 7.44(2H, d, J=8.1 Hz) and 7.33(1H, d, J=7.5 Hz) ppm.

Step B: 4-(2'-trifluoromethylphenyl)benzylalcohol

To a solution of 4-(2'-trifluoromethylphenyl)benzoic acid (1.525 g, 5.728 mmol) in THF (25 mL) at 0° C. was added 1.0 M lithium aluminum hydride in tetrahydrofuran (12.0 mL, 12.0 mmol) over 10 minutes. The reaction was allowed to stir at ambient temperature for 3 hours, cooled to 0° C., and quenched by dropwise addition of water (0.5 mL), 4 N aq. NaOH (0.5 mL), and water (1.5 mL). The reaction was filtered through a pad of Celite and the filtrate evaporated in vacuo. The residue was chromatographed (Silica gel, 20% EtOAc in hexanes) to afford the title compound.

$^1$H NMR (CDCl$_3$, 400 MHz) δ 7.74(1H, d, J=7.7 Hz), ), 7.55(1H, d, J=7.4 Hz), 7.47(1H, t, J=7.4 Hz), 7.41(2H, d, J=7.9 Hz), 7.36–7.30(3H, m) and 4.78(2H, s) ppm.

Step C: 1-(2'-Trifluoromethyl-4-biphenylmethyl)-5-(4-cyanobenzyl)imidazole hydrochloride salt To a solution of 4-(2'-trifluoromethylphenyl) benzylalcohol (362 mg, 1.44 mmol) and diisopropylethylamine (0.260 mL, 1.49 mmol) in dichloromethane (6.0 mL) at −78° C. was added trifluoromethanesulfonic anhydride (0.250 mL, 1.49 mmol) and the mixture stirred at −78° C. for 1 hour. To this mixture was added a solution of 1-trityl-4-(4-cyanobenzyl)-imidazole (613 mg, 1.44 mmol) in dichloromethane (6.0 mL). The mixture was allowed to warm to ambient temperature and stirred for 2 hours. The solvent was evaporated in vacuo. The residue was dissolved in methanol (15 mL), heated at reflux for 1 hour, and the solvent evaporated in vacuo. The residue was partitioned between $CH_2Cl_2$ and sat. aq. $NaHCO_3$ solution. The organic layer was dried, ($Na_2SO_4$) and the solvent evaporated in vacuo. The residue was chromatographed (Silica gel, 0–2% MeOH in $CH_2Cl_2$) and further purified by preparative HPLC, (gradient elution, 95:5 to 5:95% water:acetonitrile containing 0.1% trifluoroacetic acid) to afford the trifluoroacetic acid salt. The salt was partitioned between EtOAc and sat. aq. $NaHCO_3$ solution, the organic layer dried, ($Na_2SO_4$) and the solvent evaporated in vacuo to afford the imidazole. The amine was converted to the HCl salt by treatment with 1.0 equivalent of HCl in aqueous acetonitrile. Evaporation of the solvent in vacuo afforded the title compound as a white solid.

Anal. Calcd. for $C_{25}H_{18}N_3F_3$.1.00 HCl.0.85 $H_2O$: C, 64.00; H, 4.45; N, 8.96. Found: C, 64.05; H, 4.24; N, 8.80. FAB MS 418 ($MH^+$); $^1H$ NMR ($CD_3OD$, 400 MHz) δ 9.10(1H, s), ), 7.78(1H, d, J=7.1 Hz), 7.70–7.62(3H, m), 7.56(1H, t, J=7.5 Hz), 7.43(1H, s), 7.38–7.24(5H, m), 7.19 (2H, d, 8.1 Hz)), 5.48(2H, s) and 4.18(2H, s) ppm.

Example 6

1-(4-Biphenylethyl)-5-(4-cyanobenzyl)imidazole hydrochloride salt

Step A: 4-Biphenylethanol

The 4-biphenylethanol was prepared using the protocol described in example 5, step B and 4-biphenylacetic acid.

$^1H$ NMR ($CDCl_3$, 400 MHz) δ 0.60–7.55(4H, m), 7.43 (2H, t, J=7.8 Hz), 7.37–7.28(3H, m), 3.91(2H, q, J=6.4 Hz), 2.92(2H, t, J=6.6 Hz), 1.40(1H, t, J=5.8 Hz) ppm.

Step B: 1-(4-Biphenylethyl)-5-(4-cyanobenzyl)imidazole hydrochloride salt

The title compound was prepared using the protocol described in example 5, step C and 4-biphenylethanol Anal. Calcd. for $C_{25}H_{21}N_3$.1.00 HCl.0.30 $H_2O$: C, 74.08; H, 5.62; N, 10.37. Found: C, 74.40; H, 5.52; N, 9.98. FAB MS 364 ($MH^+$); $^1H$ NMR ($CDCl_3$, 400 MHz) δ 8.78(1H, d, J=1.6 Hz), 7.70(2H, d, J=8.2 Hz), 7.62–7.54(4H, m), 7.48–7.30(5H, m), 7.20–7.12(3H, m), 4.43(2H, t, J=6.9 Hz), 4.04(2H, s), and 3.10(2H, t, J=6.8 Hz) ppm.

Example 7

1-(2'-Bromo-4-biphenylmethyl)-5-(4-cyanobenzyl) imidazole hydrochloride salt

Step A: 4-(2'-Bromophenyl)benzaldehyde

To a solution of 4-formylbenzeneboronic acid (1.19 g, 7.96 mmol) and $Na_2CO_3$ (1.68 g, 15.8 mmol) in water (60 mL) was added p-dioxane (60 mL). This mixture was treated sequentially with 2-bromo iodobenzene (2.25 g, 7.95 mmol) and palladium (II) acetate (159 mg, 0.708 mmol) and allowed to stir at ambient temperature for 16 hours. The solvent was evaporated in vacuo. To the residue was added EtOAc (400 mL) and water (300 mL). The aqueous layer was extracted with EtOAc (2×200 mL). The organic extracts were combined, washed with brine (200 mL), 5% aq. $Na_2S_2O_3$ (200 mL), brine1 (200 mL), dried, ($Na_2SO_4$) and the solvent evaporated in vacuo to afford the title compound which was used in the next step without further purification.

Step B: 4-(2'-Bromophenyl)benzyl alcohol

To a solution of 4-(2'-bromophenyl)benzaldehyde 1.55 g, 7.95 mmol) in ethanol (15 mL) at 0° C. was added sodium borohydride (2.22 g, 58.7 mmol) and the reation stirred for 1 hour. The reaction was quenched with saturated aq. $NH_4Cl$ and extracted into diethyl ether. The organic extracts were washed with brine, dried, ($Na_2SO_4$) and evaporated in vacuo. The residue was purified by chromatography (Silica gel, 25% EtOAc in hexanes) to afford the title compound as a colourless oil.

$^1H$ NMR ($CDCl_3$, 400 MHz) δ 7.66(1H, dd, J=8.1 and 1.1 Hz), 7.45–7.30(6H, m), 7.23(1H, m) and 4.66(2H, s) ppm.

Step C: 1-(2'-Bromo-4-biphenylmethyl)-5-(4-cyanobenzyl)-imidazole hydrochloride salt The title compound was prepared using the protocol described in example 5, step C and 4-(2'-bromophenyl) benzyl alcohol.

Anal. Calcd. for $C_{24}H_{18}N_3Br$.100 HCl.1.46$H_2O$: C, 58.70; H, 4.50; N, 8.56. Found: C, 58.66; H, 4.10; N, 8.27. FAB MS 430($MH^+$); $^1H$ NMR ($CD_3OD$ 400 MHz) δ 9.11 (1H, s), 7.68(1H, d, J=8.1 Hz), 7.62(2H, d, J=8.3 Hz), 7.50–7.16(10H, m), 5.48(2H, s) and 4.20(2H, s) ppm.

Example 8

1-(2'-Methyl-4-biphenylmethyl)-5-(4-cyanobenzyl) imidazole hydrochloride salt

The title compound was prepared using the protocol described in example 5, steps A–C using 2-iodotoluene.

Anal. Calcd. for $C_{25}H_{21}N_3$.1.00 HCl.0.65 $H_2O$: C, 73.13; H, 5.47; N, 10.23. Found: C, 73.16; H, 5.70; N, 10.20. $^1H$ NMR ($CD_3OD$ 400 MHz) δ 9.06(1H, d, J=1.6 Hz), 7.62(2H, d, J=8.4 Hz), 7.42(1H, s), 7.35–7.10(10H, m), 5.44(2H, s), 4.21(2H, s) and 2.20(3H, s) ppm.

Example 9

1-(2'-Trifluoromethoxy-4-biphenylmethyl)-5-(4-cyanobenzyl) imidazole hydrochloride salt The title compound was prepared using the protocol described in example 5, steps A≧C using 2-trifluoromethoxyiodobenzene.

$^1H$ NMR ($CD_3OD$ 400 MHz) δ 9.08(1H, d, J=1.6 Hz), 7.61(2H, d, J=8.4 Hz), 7.52–7.38(7H, m), 7.29(2H, d, J=8.1 Hz), 7.23(2H, d, J=8.1 Hz), 5.47(2H, s) and 4.17(2H, s) ppm.

Example 10

1-(4-(3',5'-dichloro)-biphenylmethyl)-5-(4-cyanobenzyl)imidazole hydrochloride salt The title compound was prepared using the protocol described in example 5, steps A–C using 3,5-dichloroiodobenzene.

Anal. Calcd. for $C_{24}H_{17}N_3Cl_2$.1.00 HCl.0.35 $H_2O$: C, 62.52; H, 4.09; N, 9.11. Found: C, 62.57; H, 3.88; N, 9.04. FAB MS 418($MH^+$); $^1H$ NMR ($CD_3OD$ 400 MHz) δ 9.08 (1H, s), 7.57(6H, m), 7.44(2H, d, J=4.2 Hz), 7.32–7.20(4H, m), 5.46(2H, s) and 4.17(2H, s) ppm.

Example 11

1-(2'-Methoxy-4-biphenylmethyl)-5-(4-cyanobenzyl) imidazole hydrochloride salt

The title compound was prepared using the protocol described in example 5, steps A–C using 2-methoxyiodobenzene.

Anal. Calcd. for $C_{25}H_{21}N_3O$.100 HCl: C, 72.19H, 5.33; N, 9.79. Found: C, 72.12; H, 5.31; N, 10.10. $^1H$ NMR ($CD_3OD$, 400 MHz) δ 9.05(1H, d, J=1.3 Hz), 7.60(2H, d, J=7.2 Hz), 7.44(2H, d, J=8.2 Hz), 7.41 (1H, s), 7.38–7.20 (4H, m), 7.16(2H, d, J=8.1 Hz), 7.07(1H, d, J=8.0 Hz), 7.01(1H, t, J=7.5 Hz), 5.42(2H, s), 4.19(2H, s) and 3.80(3H, s) ppm.

Example 12

1-(2'-Chloro-4-biphenylmethyl)-5-(4-cyanobenzyl) imidazole hydrochloride salt

The title compound was prepared using the protocol described in example 5, steps A–C using 2-chloro iodobenzene.

Anal. Calcd. for $C_{24}H_{18}N_3.1.00$ $HCl.0.20H_2O$: C, 68.05 H, 4.61; N, 9.91. Found: C, 68.00; H, 4.77; N, 9.56. $^1H$ NMR (CD$_3$OD, 400 MHz) δ 9.09(1H, d, J=1.3 Hz), 7.61 (2H, d, J=7.2 Hz), 7.55–7.25(9H, m), 7.20(2H, d, J=8.1 Hz), 5.47(2H, s) and 4.21(2H, s) ppm.

Example 13

1-(2-Chloro-4-biphenylmethyl)-5-(4-cyanobenzyl) imidazole hydrobromide salt

Step A: 2-Chloro-4-phenyl toluene

A mixture of 2-chloro-4-iodotoluene(2.94 g, 11.63 mmol), phenyl boronic acid (1.56 g, 12.79 mmol), barium hydroxide (5.50 g, 17.44 mmol), DME (3 mL) and water (15 mL) was purged with dry argon. Tetrakis(triphenylphosphine)palladium(O) (672 mg, 0.58 mmol) was added, and the resultant solution was stirred at 80° C. for 4 hours. The solvents were evaporated in vacuo, and the residue partitioned between EtOAc and water and acidified with 1M aq. HCl. The aqueous extract was separated, and extracted with EtOAc. The organic extracts were combined, washed with NaHCO$_3$ and 5% aq. Na$_2$S$_2$O$_3$, dried, (Na$_2$SO$_4$) filtered and the solvent evaporated in vacuo. The residue was purified by chromatography (Silica gel, 10% EtOAc in hexanes) to afford the title compound. $^1H$ NMR (CDCl$_3$ 400 MHz) δ 7.62–7.54 (3H, m), 7.48–7.25(5H, m) and 2.43(3H, s) ppm.

Step B: 1-(Bromomethyl)-2-chloro-4-biphenyl

To a solution of 2-chloro-4-phenyl toluene (911 mg, 4.50 mmol) in carbon tetrachloride (18 mL) was added N-bromosuccinimide (800 mg, 4.50 mmol) and the mixture heated to 70° C. AIBN (16.4 mg, 0.10 mmol) was added and the mixture refluxed for 2 hours. The reaction was cooled, filtered, and the solvent evaporated in vacuo. The residue was chromatographed (Silica gel, 15% CH$_2$Cl$_2$ in hexanes) to afford the title compound as a white solid.

$^1H$ NMR (CDCl$_3$, 400 MHz) δ 7.62(1H, d, J=1.7 Hz), 7.60–7.34(7H, m) and 4.65(2H, s) ppm.

Step C: 1-(2-Chloro-4-biphenylmethyl)-5-(4-cyanobenzyl)-imidazole hydrobromide salt.

A suspension of 1-(bromomethyl)-2-chloro-4-biphenyl (500 mg, 1.78 mmol), 1-trityl-4-(4-cyanobenzyl)-imidazole (756 mg, 1.78 mmol) in acetonitrile (5 mL) was stirred at 55° C. for 16 hours. The solvent was evaporated in vacuo and the residue dissolved in methanol and stirred at reflux for 1 hour. The solvent was evaporated in vacuo. The residue suspended in EtOAc (10 mL) and the product isolated as a white solid by filtration. The solids were washed with EtOAc (5 mL) and diethylether (10 mL) and dried in vacuo.

Anal. Calcd. for $C_{24}H_{18}N_3Cl.1.00$ HBr.0.30H$_2$O C, 61.31 H, 4.20 N, 8.94. Found: C, 61.61; H, 4.23; N, 8.55. $^1H$ NMR (CD$_3$OD, 400 MHz) δ 8.99(1H, d, J=1.4 Hz), 7.65(1H, d, J=2.3 Hz), 7.62–7.54(4H, m), 7.54–7.43(4H, m), 7.40(1H, m), 7.29(2H, d, J=8.4 Hz), 7.11(1H, d, J=7.8 Hz), 5.52(2H, s) and 4.24(2H, s) ppm.

Example 14

1-(3-Chloro-4-biphenylmethyl)-5-(4-cyanobenzyl) imidazole hydrochloride salt

The title compound was prepared using the protocol described in example 13, steps A–C using 3-chloro-4-iodotoluene. The imidazole was isolated by chromatography (Silica gel, 2–3% MeOH in CH$_2$Cl$_2$), and converted to the HCl salt by treatment with HCl gas in EtOAc and evaporation of the solvent in vacuo.

Anal. Calcd. for $C_{24}H_{18}ClN_3.1.00$ HCl.0.30H$_2$O: C, 67.71H, 4.64; N, 9.87. Found: C, 67.75; H, 4.69; N, 9.73. $^1H$ NMR (CD$_3$OD, 400 MHz) δ 9.19(1H, s), 7.58(2H, d, J=8.0 Hz), 7.55–7.30(6H, m), 7.30–7.00(5H, m), 5.45(2H, s) and 4.23(2H, s) ppm.

Example 15

1-(4-(3',5'-Bis-tifluoromethyl)-biphenymethyl)-5-(4-cyanobenzyl) imidazole hydrochloride salt Step A: Methyl 4-(3',5'-Bis-trifluoromethylphenyl)benzoate To a solution of 3',5'-trifluoromethylbenzeneboronic acid (0.430 g, 1.57 mmol) and barium hydroxide octahydrate (0.675 g, 2.14 mmol) in water (1.5 mL) was added DME (5 mL). This mixture was treated sequentially with methyl-4-iodobenzoate (0.375 g, 1.43 mmol) and tetrakis triphenylphosphine palladium (0) (83 mg, 0.07 mmol) and heated at 80° C. for 5 hours. The reaction cooled, acidified to pH 1 with aq. HCl and extracted with EtOAc (2×50 mL) The combined organic extracts were washed with sat. aq. NaHCO$_3$, brine, dried, (Na$_2$SO$_4$) and the solvent evaporated in vacuo. The residue was dissolved in methanol (50 mL), saturated with gasseous HCl and stirred for 16 hours at ambient temperature. The solvent was evaporated in vacuo to afford the title compound as a solid. $^1H$ NMR (CDCl$_3$, 400 MHz) δ 8.17(2H, d, J=8.4 Hz), 8.04(2H, s), 7.91(1H, s), 7.68(2H, d, J=8.4 Hz) and 3.97(3H, s) ppm.

Step B: 1-(4-(3',5'-Bis-trifluoromethyl)-biphenylmethyl)-5-(4-cyanobenzyl)imidazole hydrochloride salt The title compound was prepared using the protocol described in example 5, steps B–C using methyl-{4-(3',5'-bistrifluoromethylphenyl)benzoate.

Anal. Calcd. for $C_{26}H_{17}N_3F_6.1.80$ HCl C, 60.69; H, 3.49; N, 8.17. Found: C, 60.69; H, 3.35; N, 7.92. FAB MS 486(MH$^+$); $^1H$ NMR (CD$_3$OD,400 MHz) δ 9.70(1H, d, J=1.4 Hz),8.16(2H, s), 7.98(1H, s), 7.68(2H, d, J=8.4 Hz), 7.57(2H, d, J=8.4 Hz), 7.43(1H, s), 7.27(4H, m), 5.47(2H, s) and 4.17(2H, s) ppm.

Example 16

1-(2'-Trifluoromethyl-4-biphenylmethyl)-5-(4-cyanobenzyl)-4-methylimidazole hydrochloride salt Step A: 4-Iodo-5-methylimidazole To a solution of 4-methyl imidazole(8.20 g, 100 mmol) and sodium carbonate (21.2 g, 200 mmol) in water (650 mL) was added a solution of sodium iodide (26.5 g, 180 mmol) and iodine (25.4 g, 100 mmol) in water (350 mL) over 90 minutes at room temperature. The reaction was stirred a further 30 minutes and filtered. The resulting white solid was washed with water and dried in vacuo at 50° C.

$^1H$ NMR (CD$_3$OD 400 MHz) d 7.57 (1H, s) 4.86(1H, brs) and 2.20(3H, s)ppm.

Step B: 1-Trityl-4-iodo-5-methylimidazole

To a cold (0° C.) solution of 4-iodo-5-methylimidazole (5.0 g, 24.0 mmol) and triethylamine (5.0 mL, 36.0 mmol) in CH$_2$Cl$_2$ (100 mL) and 1,4-dioxane (50 mL) was added trityl chloride (8.0 g, 29.0 mmol). The resultant mixture was stirred for 2 hours and quenched with ice and extracted with diethyl ether. The organic extracts were washed with sat. aq. NaHCO$_3$, dried (K$_2$CO$_3$) and the solvent evaporated in vacuo. The product mixture was concentrated onto silica gel and chromatographed (Silica gel, 30–50% EtOAc in hexanes) to afford the title compound as a pale yellow powder.

$^1$H NMR (CDCl$_3$, 400 MHz) δ 7.43(1H, s), 7.35–7.30 (9H, m), 7.25–7.10 (6H, m) and 2.27(3H, s) ppm.

Step C: 1-Trityl-4-(4-cyanobenzyl)5-methylimidazole

To a suspension of activated zinc dust (0.262 g, 3.99 mmol) in THF (1 mL) was added dibromoethane (0.035 mL, 0.039 mmol) and the reaction stirred under argon at 20° C. for 45 minutes. The suspension was cooled to 0° C. and a-bromo-p-tolunitrile (0.51 g, 2.60 mmol) in THF (3 mL) was added dropwise over a period of 10 minutes. The reaction was then allowed to stir at 20° C. for 45 minutes and bis(triphenylphosphine)Nickel II chloride (0.130 g, 0.399 mmol) and 5-iodo-1-trityl imidazole (15.95 g, 36.6 mmol) were added in one portion The resulting mixture was stirred 3 hours at 20° C. and then quenched by addition of saturated NH$_3$ solution (2 mL) and the mixture stirred for 3 hours, extracted with EtOAc (2×25 mL), dried (MgSO$_4$) and the solvent evaporated in vacuo. The residue was chromatographed (Silica gel, 20% EtOAc in CH$_2$Cl$_2$ to afford the title compound as a white solid.

$^1$H NMR (CD$_3$OD, 400 MHz) δ 7.62 (2H, d, J=8.3 Hz), 7.40–7.34(9H, m), 7.31(2H, d, J=8.3 Hz), 7.26(1H, s), 7.18–7.10(6H, m), 3.93(2H, s), and 1.41(3H, s) ppm.

Step D: 1-(2'-Trifluoromethyl-4-biphenylmethyl)-5-(4-cyanobenzyl)-4-methylimidazole hydrochloride salt The title compound was prepared using the protocol described in example 5, step C using 1-trityl-4-(4-cyanobenzyl)-5-methylimidazole.

Anal. Calcd. for C$_{26}$H$_{20}$N$_3$F$_3$·1.00 HCl C, 66.74 H, 4.52; N, 8.98. Found: C, 66.42; H, 4.42; N, 8.86. $^1$H NMR (CD$_3$OD 400 MHz) δ 8.98(1H, s), 7.77(1H, d, J=7.8 Hz), 7.66(1H, t, J=7.5 Hz), 7.62–7.50(3H, m), 7.35–7.00(7H, m), 5.37(2H, 4.20(2H, s) and 2.34(3H, s) ppm.

Example 17

1-(4-Biphenylmethyl)-5-(4-cyanophenyloxy)-imidazole

Step A: 5-(4-Cyanophenyloxy)imidazole

Sodium metal (1.10 g, 47.8 mmol) was dissolved in anhydrous methanol and 4-cyanophenol (5.70 g, 47.8 mmol) was added. The resultant solution was concentrated and dried under vacuum overnight. A mixture of this sodium salt and 4-cyanophenol (25 g, mp 110–113° C.) was heated to 125–130° C. and neat methyl N-(cyanomethyl) methanimidate (5.0 g, 51 mmol; Hosmane, R. S. et al, J. Org. Chem., 1212, 1984) was added dropwise over a period of 10 minutes under a slow stream of dry argon. The resultant mixture was stirred at 120° C. for 2 hours, cooled, and the reaction product partitioned between methylene chloride (500 mL) and aqueous sodium hydroxide (1 M, 500 mL). The aqueous layer was separated and extracted with methylene chloride (3×100 mL). The organic extracts were combined, washed with brine (100 mL), dried (K$_2$CO$_3$), and the solvent evaporated in vacuo. The residue was purified by chromatography (Silica gel, 3:7 acetone in CHCl$_3$) to afford the title compound as a white powder.

$^1$H NMR (DMSO-d$_6$ 400 MHz) δ 7.79 (2H, d, J=9.0 Hz), 7.54 (1H, s), 7.11 (2H, d, J=9.0 Hz) and 6.96 (1H, s) ppm.

Step B: 4-(4-Cyanophenyloxy)-1-trityl-imidazole

To a cold (0° C.) solution of 4-(4-cyanophenyloxy)-imidazole (155 mg, 0.84 mmol) and triethylanine (0.129 mL, 0.92 mmol) in DMF (1 mL) was added trityl chloride (245 mg, 0.88 mmol). The resultant mixture was stirred at ambient temperature for 5 days. The product mixture was concentrated onto silica gel, chromatographed (Silica gel, 1:9 acetone in CHCl$_3$) to afford the title compound as a white powder.

$^1$H NMR (CDCl$_3$ 400 MHz) δ 7.57 (2H, d, J=9.0 Hz), 7.38 (1H, s), 7.35–7.09 (16H, m), 7.08 (2H, d, J=9.0 Hz) and 6.54(1H, s) ppm.

Step C: 1-(4-Biphenylmethyl)-5-(4-cyanophenyloxy)-imidazole

The title compound was prepared u:sing the protocol described in example 5, step C using 4-biphenyl methanol and substituting 4-(4-cyanobenzyl)-1-trityl-imidazole with 4-(4-cyanophenyloxy)-1-trityl-imidazole. The title compound was purified by chromatography (Silica gel 3:7 acetone in CHCl$_3$) and obtained as a white solid.

Anal. Calcd for C$_{23}$H$_{17}$N$_3$O·0.35 H$_2$O: C, 77.23; H, 4.99; N, 11.75. Found: C, 77.30; H, 4.95; N, 11.58. $^1$H NMR (CDCl$_3$, 400 MHz) δ 7.80–7.35 (10 H, m), 7.16 (2H, d, J=8.1 Hz), 7.01(2H, d, J=8.8 Hz), 6.74 (1H, s) and 4.98 (2H, s) ppm.

Using the same procedure but substituting 4-(2-trifluoromethylphenyl)-benzylalcohol for biphenylmethanol in Step C the following compound was prepared:

1-(4-(2-trifluoromethylphenyl)phenyl methyl)-5-(4-cyanophenyloxy)-imidazole

Anal. Calcd for C$_{24}$H$_{16}$N$_3$OF$_3$·0.3 H$_2$O: C, 67.86; H, 3.94; N, 9.89. Found: C, 67.85; H, 3.84; N, 9.73.

Using the same procedure but substituting 4-bromophenol for 4-cyanophenol in Step A the following compound was prepared:

1-(4-Biphenylmethyl)-5-(4-bromophenyloxy)-imidazole

Anal. Calcd for C$_{22}$H$_{17}$BrN$_2$O: C, 65.20; H, 4.23; N, 6.91. Found: C, 65.26; H, 4.33; N, 6.80.

Example 18

5-(4-Cyanophenyloxy)-1-(2'-methyl-4-biphenylniethyl)-imidazole hydrochloride salt The title compound was prepared using the protocol described in example 17, step C, substituting 4-biphenylmethanol with 2'-methyl-4-biphenylmethanol. The hydrochloride salt was obtained by treatment of a solution of the imidazole in acetonitrile with aq. HCl and evaporation of the solvents in vacuo.

Anal. Calcd for C$_{23}$H$_{17}$N$_3$O·0.58 H$_2$O·1.45 HCl: C, 67.23; H, 5.08; N, 9.80. Found: C, 67.30; H, 5.08; N, 9.74. $^1$H NMR CDCl$_3$ δ 7.56 (2H, d, J=6.9 Hz), 7.46 (1H, s), 7.26–7.10 (8H, m), 7.02 (2H, d, J=8.8 Hz), 6.75 (1H, s), 4.99 (2H, s) and 2.19 (3H, s) ppm.

Example 19

5-(4-Biphenyloxy)-1-(4-cyanobenzyl)-imidazole trifluoroacetate salt

Step A: 4-(4-Bromophenyloxy)imidazole

The title compound was prepared as white solid using the protocol described in example 17—step A, substituting 4-cyanophenol with 4-bromophenol, and performing the reaction at 100–110° C.

$^1$H NMR (DMSO-d$_6$ 400 MHz) δ 7.49(1H, s), 7.48(2H, d, J=9.0 Hz), 6.93(2H, d, J=9.0 Hz) and 6.85(1H, s) ppm.

Step B: 4-(4-Bromophenyloxy)-1-trityl-imidazole

The title compound was prepared as white solid using the protocol described in example 17—step B, using 4-(4-bromophenyloxy) imidazole.

Step C: 5-(4-Bromophenyloxy)-1-(4-cyanobenzyl)-imidazole

The title compound was prepared as a white solid using the protocol described in example 5, step C using, 4-cyanobenzyl alcohol and 4-(4-bromophenyloxy)-1-tritylimidazole. The title compound was purified by chromatography (Silica gel 3:7 acetone in CHCl$_3$).

$^1$H NMR (CDCl$_3$ 400 MHz) δ 7.61(2H, d, J=8.1 Hz), 7.38(2H, d, J=9.0 Hz), 7.37(1H, s), 7.21(2H, d, J=9.0 Hz), 6.63(1H, s) and 5.03(2H, s) ppm.

Step D: 5-(4-Biphenyloxy)-1-(4-cyanobenzyl)-imidazole trifluoroacetate salt

A mixture of 5-(4-bromophenyloxy)-1-(4-cyanobenzyl)-imidazole (100 mg, 0.28 mmol), phenyl boronic acid (69 mg, 0.56 mmol), K$_3$PO$_4$ (240 mg, 1.13 mmol), and DMF (5 mL) was purged with dry argon for a period of 15 minutes. Tetrakis(triphenylphosphine)palladium(0) (33 mg, 0.028 mmol) was added, and the resultant solution was stirred at 80° C. for 18 hours. The solvents were evaporated in vacuo, and the residue partitioned between CH$_2$Cl$_2$ and water. The aqueous extract was separated, and extracted with CH$_2$Cl$_2$. The organic extracts were combined, dried (Na$_2$SO$_4$, filtered and evaporated in vacuo. The residue was purified by chromatography (Silica gel, eluting with 3:7 acetone in CHCl$_3$, and the trifluoroacate salt obtained by treatment of a solution of the imidazole in acetonitrile with aqueous TFA and evaporation of the solvents in vacuo.

Anal. Calcd for C$_{23}$H$_{17}$N$_3$O•1.25 TFA: C, 62.01; H, 3.72; N, 8.51. Found: C, 61.99; H, 3.69; N, 8.13. $^1$H NMR (CDCl$_3$, 400 MHz) δ 7.60(2H, d, J=8.3 Hz), 7.54–7.32(8H, m), 7.23(2H, d, J=8.5 Hz), 7.00(2H, d, J=8.8 Hz), 6.72(1H, s) and 5.06 (2H, s) ppm.

Example 20

5-(2'-Methyl-4-biphenoxy)-1-(4-cyanobenzyl)-imidazole trifluoroacetate salt

The title compound was prepared as a white solid using the protocol described in example 19—step D, substituting phenyl boronic acid with o-tolylboronic acid, and stirring the reaction mixture at 100° C. for 24 hours.

Anal. Calcd for C$_{24}$H$_{19}$N$_3$O•1.30 TFA•0.75 H$_2$O: C, 60.72; H, 3.98; N, 7.99. Found: C, 60.77; H, 4.00; N, 7.76. $^1$H NMR (CDCl$_3$ 400 MHz) δ 7.61(2H, d, J=8.5 Hz), 7.41(1H, s), 7.27–7.18(8H, m), 6.98(2H, d, J=8.8 Hz),6.70 (1H, s), 5.08(2H, s) and 2.25(3H, s) ppm.

Example 21

5-(4-(3',5'-dichloro)biphenylmethyl)-1-(4-cyanobenzyl)imidazole hydrochloride salt Step A: 4-(3',5'-Dichlorophenyl) benzyl alcohol The title compound was prepared using the protocol described in example 5, steps A–B using 3,5-dichloroiodobenzene.

$^1$H NMR (CDCl$_3$, 400 MHz) δ 7.54(2H, dt, J=8.20 and 2.0 Hz), 7.48–7.43(4H, m), 7.33(1H, t, J=2.0 Hz), 4.76(2H, d, J=5.9 Hz) and 1.68(1H, t, J=5.9 Hz) ppm.

Step B: 4-(3',5'-Dichlorophenyl) benzyl bromide

To a solution of triphenylphospine (636 mg, 2.42 mmol) and carbon tetrabromide (830 mg, 2.50 mmol) in diethyl ether (5 mL) was added a solution of 4-(3',5'-bis-chlorophenyl) benzyl alcohol (50 mg, 1.98 mmol) in CH$_2$Cl$_2$ (12 mL). The reaction was stirred at ambient temperature for 16 hours, silica gel was than added and the solvent evaporated in vacuo. The product was isolated by chromatography (Silica gel, 10–30% EtOAc in hexanes) and obtained as a white solid.

$^1$H NMR (CDCl$_3$, 400 MHz) δ 7.54–7.46(4H, m), 7.46–7.43(2H, m), 7.35(1H, m) and 4.54(2H, s) ppm.

Step C: 1-Trityl-4-(4-(3',5'-dichloro)-biphenylmethyl-imidazole

To a suspension of activated zinc dust (0.080 g, 1.22 mmol) in THF (0.25 mL) was added dibromoethane (0.011 mL, 0.122 mmol) and the reaction stirred under argon at 20° C. for 45 minutes. 4-(3',5'-Dichlorophenyl) benzyl bromide (0.250 g, 0.791 mmol) in THF (1 mL) was added dropwise over a period of 10 minutes. The reaction was then allowed to stir at 20° C. for 45 minutes and bis(triphenylphosphine) Nickel II chloride (0.04 g, 0.031 mmol) and 4-iodo-1-trityl-imidazole (15.95 g, 36.6 mmol) were added in one portion. The resulting mixture was stirred 16 hours at 20° C. and then quenched by addition of sat. aq. NH$_4$Cl solution (2 mL) and the mixture stirred for 3 hours, extracted with EtOAc (2×25 mL), dried (MgSO$_4$) and the solvent evaporated in vacuo. The residue was chromatographed (Silica gel, 30–50% EtOAc in CH$_2$Cl$_2$) to afford the title compound as a white solid.

$^1$H NMR (CDCl$_3$, 400 MHz) δ 7.50–7.28 (15H, m), 7.18–7.10(6H, m), 6.59(1H, s) and 3.93(2H, s) ppm.

Step D: 5-(4-(3',5'-Dichloro)-biphenylmethyl)-1-(4-cyanobenzyl) imidazole hydrochloride salt A suspension of 4-cyanobenzyl bromide (19.1 mg, 0.097 mmol) and the trityl derivative from step C (52.5 mg, 0.096 mmol) in acetonitrile (0.4 mL) was stirred at 55° C. for 16 hours. The solvent was evaporated in vacuo and the residue dissolved in methanol (4 mL) and stirred at reflux for 1 hour. The solvent was evaporated in vacuo and partitioned between EtOAc and sat. aq. NaHCO$_3$ the organic layer was dried, (Na$_2$SO$_4$) and evaporated in vacuo. The residue was chromatograped (Silica gel, 2% MeOH in CH$_2$Cl$_2$), to afford the imidazole, which was dissolved in acetonitrile and converted to the HCl salt by addition of 1 equivalent of 1 M HCl. Evaporation of the solvent in vacuo afforded the title compound as a white solid.

$^1$H NMR (CD$_3$OD 400 MHz) δ 8.97(1H, s), 7.63(2H, d, J=8.2 Hz), 7.53(2H, s), 7.48(2H, d, J=8.2 Hz), 7.42(2H, s), 7.21(2H, d, J=8.0 Hz), 7.18(2H, d, J=8.2 Hz), 5.49(2H, s) and 4.07(2H, s) ppm.

Example 22

1-(4-biphenylmethyl)-5-(1-(R,S)-acetoxy-1-(4-cyanophenyl)methylimidazole hydrochloride salt Step A: 1-Trityl-4-(1-(R,S)-hydroxy-1-(4-cyanophenyl) methylimidazole To a solution of 1-trityl-4-iodoimidazole[1] (10 g, 23 mmol) in CH$_2$Cl$_2$ (93 mL) at room temperature was added ethyl magnesium bromide (8.4 mL of a 3M solution in diethyl ether) and the reaction stirred for 2 hours. 4-Cyanobenzaldehyde (3.36g, 25.21 mmol) was added and the reaction stirred a further 16 hours. The reaction was quenched with sat. aq. NH$_4$Cl and stirred until homogeneous. The pH was adjusted to 8.5 with sat. aq. NaHCO$_3$ and extracted with CH$_2$Cl$_2$. The combined organic extracts were washed with brine, dried (MgSO$_4$) and the solvent evaporated in vacuo. The resulting white solid was suspended in EtOAc (200 mL) and collected by filtration.

$^1$H NMR (CDCl$_3$, 400 MHz) δ 7.60(2H, d, J=8.2 Hz), 7.52(2H, d, J=8.2 Hz), 7.41(1H, d, J=1.4 Hz), 7.38–7.20(9H, m), 7.15–7.02(6H, m), 6.62(1H, s), 5.79(1H, d, J=4.6 Hz), and 3.11(1H, d, J=4.6 Hz) ppm. 1.*Journal of Organic Chemistry* 56, 5739, 1991.

Step B: 1-Trityl-4-(1-(R,S)-acetoxy-1-(4-cyanophenyl) methylimidazole

A solution of 1-trityl-4-(1-(R,S)-hydroxy-1-(4-cyanophenyl)methylimidazole (2.00 g, 4.53 mmol), pyridine (1.10 mL) and acetic anhydride (0.641 mL) in DMF (20 mL) at room temperature was stirred for 16 hours. The reaction was quenched with sat. aq. NaHCO$_3$ (50 mL) and water (50 ml), extracted with ethyl acetate dried, (MgSO$_4$) and the solvent evaporated in vacuo. The resulting solids were washed with diethylether to provide the title compound as an off white solid.

$^1$H NMR (CDCl$_3$, 400 MHz) δ 7.62(2H, d, J=8.4 Hz), 7.53(2H, d, J=8.2 Hz), 7.39(1H, d, J=1.3 Hz), 7.38–7.28(9H, m), 7.15–7.02(6H, m), 6.78(2H, s) and 2.12(3H, s) ppm.

Step C: 1-(4-Biphenylmethyl)-5-(1-(R,S)-acetoxy-1-(4-cyanophenyl)methylimidazole hydrochloride salt The title compound was prepared using the protocol described in example 5, step C using 1-trityl-4-(1-(R,S)-acetoxy-1-(4-cyanophenyl)methylimidazole and 4-biphenylmethanol.

Anal. Calcd. for C$_{26}$H$_{21}$N$_3$O$_2$.1.00 HCl.0.55H$_2$O C, 68.81H, 5.13 N, 9.26. Found: C, 68.98; H, 5.22; N, 8.87. FAB MS 408(MH$^+$); $^1$H NMR (CD$_3$OD 400 MHz) δ 9.09 (1H, s), 7.70(2H, d, J=8.4 Hz), 7.61(4H, t, J=8.2 Hz), 7.45(1H, s), 7.45(4H, t, J=8.2 Hz), 7.36(1H, t, J=7.3 Hz), 7.23(2H, d, J=8.3 Hz), 7.05(1H, s), 5.54(2H, d, J=2.2 Hz) and 1.96(3H, s) ppm.

Example 23

1-(4-Biphenylmethyl)-5-(1-(R,S)-hydroxy-1-(4-cyanophenyl) methylimidazole hydrochloride salt To a solution of 1-(4-biphenylmethyl)-5-(1-(R,S)-acetoxy-1-(4-cyanophenyl)methylimidazole, from example 22, (389 mg 0.955 mmol) in THF (5 mL) at 0° C. was added lithium hydroxide (0.192 mL), 0.192 mmol)and the reaction stirred at room temperature for 3 hours. EtOAc (75 mL) and water (25 mL) were added and the organic layer separated, dried (MgSO$_4$) and the solvent evaporated in vacuo. The residue was purified by chromatography (Silica gel, 5% MeOH in CH$_2$Cl$_2$) and converted to the HCl salt by treatment with HCl in EtOAc and evaporation of the solvent in vacuo.

Anal. Calcd. for C$_{24}$H$_{19}$N$_3$O.0.70 HCl C, 73.73H, 5.08 N, 10.75. Found: C, 73.76; H, 5.17; N, 10.58. $^1$H NMR (CD$_3$OD, 400 MHz) δ 8.57(1H, s), 7.67(2H, d, J=8.4 Hz), 7.63–7.56(4H, m), 7.51(2H, d, J=8.0 Hz), 7.44(2H, t, J=7.4 Hz), 7.35(1H, t, J=7.5 Hz), 7.23(2H, d, J=8.2 Hz), 7.05(1H, s), 5.94(1H, s), 5.50(1H, d, J=15.4 Hz) and 5.45(1H, d, J=15.4 Hz) ppm.

Example 24

1-(4-Biphenylmethyl)-5-(1-(R,S)-amino-1-(4-cyanophenyl) methylimidazole hydrochloride salt A solution of 1-(4-biphenylmethyl)-5-(1-(R,S)-hydroxy-1-(4-cyanophenyl)methylimidazole (49.0 mg, 0.122 mmol) in thionyl chloride (5 mL) at room temperature was stirred for 45 minutes. The solvent was evaporated in vacuo and the residue was treated with 4M NH$_3$ in MeOH and the solution stirred for 1 hour and the solvents evaporated in vacuo. The residue was purified by chromatography (Silica gel, 2–5% NH$_4$OH in acetonitrile) and converted to the HCl salt by treatment with HCl in acetonitrile and evaporation of the solvent in vacuo.

Anal. Calcd. for C$_{24}$H$_{20}$N$_4$ 2.35HCl C, 64.04H, 5.00 N, 12.45. Found: C, 64.13; H, 4.98; N, 12.43. $^1$H NMR (CD$_3$OD 400 MHz) δ 9.20(1H, s), 7.93(1H, s), 7.64(2H, d, J=8.4 Hz), 7.54(2H, d, J=7.3 Hz), 7.48–7.40(4H, m), 7.36 (3H, m), 7.09(2H, d, J=8.2 Hz), 5.98(1H, s), 5.54(1H, d, J==14.9 Hz) and 5.45(1H, d, J=14.9 Hz) ppm.

Example 25

1-(4-biphenylmethyl)-5-(1-(R,S)-methoxy-1-(4-cyanophenyl)-methylimidazole

The title compound was obtained as a minor component by the protocol described in example 24.

$^1$H NMR (CD$_3$OD 400 MHz) δ 7.76(2H, d, J=8.2 Hz), 7.75(1H, s), 7.64(2H, d, J=7.6 Hz), 7.58(2H, d, J=8.2 Hz), 7.50–7.40(4H, m), 7.36(1H, t, J=7.5 Hz), 7.13(2H, d, J=7.9 Hz), 6.56(1H, s), 5.47(1H, s), 5.25(1H, d, J=15.4 Hz), 5.20(1H, d, J=15.4 Hz) and 3.17(3H, s) ppm.

Example 26

1-(4-Cyanobenzyl)-5-(1-hydroxy-1-(4-biphenyl)-methyl imidazole

Step A: 1-Triphenylmethyl-4-(hydroxymethyl)imidazole

To a solution of 4-(hydroxymethyl)imidazole hydrochloride (35.0 g, 260 mmol) in 250 mL of dry DMF at room temperature was added triethylamine (90.6 mL, 650 mmol), a white solid precipitated from the solution. Chlorotriphenylmethane (76.1 g, 273 mmol) in DMF (500 mL) was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: 1-Triphenylmethyl-4-(acetoxymethyl)imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl (2×1 L), sat. aq. NaHCO$_3$, and brine, and then dried, (Na$_2$SO$_4$) and concentrated in vacuo to provide the crude product. The acetate was isolated as a white powder which was sufficiently pure for use in the next reaction.

Step C: 1-(4-Cyanobenzyl)-5-(acetoxymethyl)imidazole hydrobromide

A solution of the product from Step B (85.8 g, 225 mmol) and a-bromo-p-tolunitrile (50.1 g, 232 mmol) in EtOAc (500 mL) was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, heated at 60° C. for two hours, cooled to room temperature, and filtered. The filtrate was concentrated in vacuo to a volume 100 mL, then heated at 60° C. for two hours, cooled to room temperature, and concentrated in vacuo to provide a pale yellow solid. All of the solid material was combined, dissolved in methanol (500 mL), and warmed to 60° C. After two hours, the solution was concentrated in vacuo to provide a white solid which was triturated with hexane to remove soluble materials. Evaporation of residual solvent in vacuo provided the titled product hydrobromide as a white solid which was used in the next step without further purification.

Step D: 1-(4-Cyanobenzyl)-5-(hydroxymethyl)imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO$_3$ and brine. The solution was then dried, (Na$_2$SO$_4$) filtered, and concentrated in vacuo to provide the crude product as a pale yellow fluffy solid which was sufficiently pure for use in the next step without further purification.

Step E: 1-(4-Cyanobenzyl)-5-imidazole carboxaldehyde

To a solution of the alcohol from Step D (21.5 g, 101 mmol) in DMSO (500 mL) at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried, ($Na_2SO_4$), and concentrated in vacuo to provide the aldehyde as a white powder which was sufficiently pure for use in the next step without further purificaton.

Step F: 1-(4-Cyanobenzyl)-5-(1-hydroxy-1-(4-biphenyl)-methyl imidazole

A Grignard reagent, freshly prepared from 4-bromobiphenyl (116 mg, 0.500 mmol) and magnesium turnings (11 mg, 0.73 mmol) in dry THF (0.50 mL) was added to a dry Argon-purged 3 mL flask containing the 1-(4-cyanobenzyl)-5-imidazole carboxaldehyde (105 mg, 0.50 mmol) in dry THF (0.2 mL) with vigorous stirring at room temperature. After 1 hour the reaction was quenched with sat. aq. $NH_4Cl$ (5 mL) and distributed between EtOAc (50 mL) and $H_2O$ (50 mL). The organic phase was evaporated in vacuo and the residue chromatographed (Silica gel, 5% MeOH in $CHCl_3$) to afford the title compound.

Anal. Calcd for $C_{24}H_{19}N_3O \cdot 0.10\ CHCl_3 \cdot 0.10\ CH_3OH$: C, 76.37 H, 5.16; N, 11.04. Found: C, 76.13; H, 5.10; N, 10.76. FAB MS 366 ($MH^+$).

Example 27

1-(4-Cyanobenzyl)-5-(1-oxo-1-(4-biphenyl)-methyl imidazole

The alcohol from example 26 (105 mg, 0.228 mmol) in dioxane (3 mL) and activated manganese dioxide (300 mg) and the mixture was stirred at reflux for 2 hours. The mixture was filtered and the clear filtrate was evaporated and the residue chromatographed (Silica gel, 3% MeOH in $CHCl_3$) to afford the title compound.

Anal. Calcd for $C_{24}H_{17}N_3O \cdot 0.35\ CHCl_3$: C, 72.17; H, 4.32; N, 10.37. Found: C, 71.87; H, 4.45; N, 10.29.

Example 28

1-(4-Cyanobenzyl)-5-(1-hydroxy-1-(3-fluoro-4-biphenyl)-methyl imidazole

A Grignard reagent, freshly prepared from 4-bromo-2-fluorobiphenyl] (251 mg, 1 mmol) and magnesium turnings (36 mg, 1.45 mmol) in dry THF (1 mL) was added to a dry argon-purged 5 mL flask containing 1-(4-cyanobenzyl)-5-imidazole carboxaldehyde (212 mg, 1 mmol) in dry THF (0.40 mL) with vigorous stirring at room temperature. After 1 hour the reaction was quenched with sat. aq. $NH_4Cl$ (10 mL) and distributed between EtOAc (100 mL) and $H_2O$ (50 mL). The organic phase was evaporated and the residue was chromatographed (Silica gel, 5% MeOH in $CHCl_3$) to afford the title compound.

Anal. Calcd for $C_{24}H_{18}N_3OF \cdot 0.05\ CHCl_3$: C, 74.18; H, 4.67; N, 10.79. Found: C, 74.13; H, 4.97; N, 10.48. FAB MS 384($MH^+$); $^1H$ NMR ($CDCl_3$, 400 MHz) δ 5.25(2H, d, J=3.6 Hz), 5.78 (1H, s), 6.84 (1H, s), 7.04–7.13 (4H, m), 7.30–7.39 (2H, m) and 7.45–7.55 (7H, m) ppm.

Example 29

1-(4-Cyanobenzyl)-5-(1-hydroxy-1-(3-biphenyl) methyl-imidazole

A Grignard reagent, freshly prepared from 3-biphenylbromide (116 mg, 0.50 mmol) and magnesium turnings (18 mg, 0.73 mmol) in dry THF (0.5 mL) was added to a dry Argon-purged 3 mL flask containing 1-(4-cyanobenzyl)-5-imidazole carboxaldehyde (105 mg, 0.50 mmol) in dry THF (0.20 mL) with vigorous stirring at room temperature. After 1 hour the reaction was quenched with sat. $NH_4Cl$ (5 mL) and distributed between EtOAc (50 mL) and $H_2O$ (50 mL). The organic phase was evaporated and the residue chromatographed (Silica gel, 5% MeOH in $CHCl_3$) to afford the title compound.

Anal. Calcd for $C_{24}H_{19}N_3O \cdot 0.10\ CHCl_3 \cdot 0.15 CH_3OH$: C, 75.34 H, 5.10; N, 10.87. Found: C, 75.25 H, 5.13; N, 10.48. FAB MS 366 ($MH^+$); $^1H$ NMR ($CDCl_3$, 400 MHz) δ 5.23 (2H, d, J=3.6 Hz), 5.78 (1H, s), 6.81(1H, s), 7.02(2H, d, J=3.6 Hz), 7.26 (2H, d, J=3.6 Hz) 7.32–7.37(3H, m) and 7.39–7.52 (7H, m) ppm.

Example 30

5-(2-[1,1'-Biphenyl]vinylene)-1-(4-cyanobenzyl) imidazole trifluoroacetic acid salt A mixture of 4-biphenyl bromide (260 mg, 1.1 mmol), 5-vinyl-1-(4-cyanobenzyl)imidiazole (248 mg, 1 mmol), palladium (II) acetate (10 mg), tri-o-tolylphosphine (30 mg), methylamine (500 mL) in DMF (1 mL) was heated at 95° C. for 20 hours. The dark solution was cooled and chromatographed (Silica gel, 1% MeOH in $CHCl_3$) to yield crude product which was further purified by preparative HPLC, (gradient elution, 95:5 to 5:95% water:acetonilrile containing 0.1% trifluoroacetic acid) to afford the title compound as a white solid.

Anal. Calcd. for $C_{24}H_{19}N_3 \cdot 1.40\ C_2HO_2F_3$: C, 64.07; H, 3.95; N, 8.06. Found: C, 64.05; H, 3.99; N, 7.68. FAB MS 362 ($MH^+$).

Example 31

1-[N-(1-(4-cyanobenzyl)-5-imidazolylmethyl) amino]-3-methoxy-4-phenylbenzene

Step 1: Preparation of 1-triphenylmethyl-4-(hydroxymethyl)-imidazole

To a solution of 4-(hydroxymethyl)imidazole hydrochloride (35 g) in 250 mL of dry DMF at room temperature was added triethylamine (90.6 mL). A white solid precipitated from the solution. Chlorotriphenylmethane (76.1 g) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step 2: Preparation of 1-triphenylmethyl-4-(acetoxymethyl)-imidazole

The product from Step 1 was suspended in 500 mL of pyridine. Acetic anhydride (74 mL) was added dropwise, and the reaction was stirred for 48 hours during which it became homogeneous. The solution was poured into 2 L of EtOAc, washed with water (3×1 L), 5% aq. HCl soln. (2×1 L), sat. aq. $NaHCO_3$, and brine, then dried ($Na_2SO_4$), filtered, and concentrated in vacuo to provide the crude product. The titled acetate product was isolated as a white powder (85.8 g) which was sufficiently pure for use in the next step.

Step 3: Preparation of 1-(4-cyanobenzyl)-5-(acetoxymethyl) imidazole hydrobromide A solution of the product from Step 2 (85.8 g) and α-bromo-p-tolunitrile (50.1 g) in 500 mL of EtO Ac was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid (50.4 g, 89% purity by HPLC) which was used in the next step without further purification.

Step 4: Preparation of 1-(4-cyanobenzyl)-5-(hydroxymethyl)-imidazole

To a solution of the acetate from Step 3 (50.4 g) in 1.5 L of 3:1 THF/water at 0° C. was added lithium hydroxide monohydrate (18.9 g). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product (26.2 g) as a pale yellow fluffy solid which was sufficiently pure for use in the next step without further purification.

Step 5: Preparation of 1-(4-cyanobenzyl)-5-imidazole-carboxaldehyde

To a solution of the alcohol from Step 4 (21.5 g) in 500 mL of DMSO at room temperature was added triethylamine (56 mL), then $SO_3$-pyridine complex (40.5 g). After 45 minutes, the reaction was poured into 2.5 L of EtOAc, washed with water (4×1 L) and brine, dried ($Na_2SO_4$), filtered, and concentrated in vacuo to provide the titled aldehyde (18.7 g) as a white powder which was sufficiently pure for use in the next step without further purification.

Step 6: Preparation of 1-[N-(1-(4-cyanobenzyl)-5-imidazolylmethyl)amino]-3-methoxy-4-phenylbenzene To a solution of 1-amino-3-methoxy-4-phenylbenzene in 1,2-dichloroethane at 0° C. was added 4A powdered molecular sieves and sodium triacetoxyborohydride. 1-(4-Cyanobenzyl)-5-imidazole-carboxaldehyde was added, followed by 5 drops of acetic acid. The cooling bath was removed after 5 hours, and the reaction was stirred for another 15 hours. The reaction was poured into ethyl acetate and water. The organic layer was extracted with sat. aq. $NaHCO_3$ solution and brine, then dried ($Na_2SO_4$) and concentrated in vacuo to provide the product.

Analysis calculated for $C_{25}H_{22}N_4O$: C, 73,38; H, 6.07; N, 12.53; Found: C, 73.36; H, 6.00; N, 12.49.

Example 32

1-(3'-Methyl-4-biphenylmethyl)-5-(4-cyanobenzyl) imidazole hydrochloride salt

The title compound was prepared using the protocol described in Example 5, steps A–C using 3-iodotoluene.

Anal. Calcd. for $C_{25}H_{21}N_3 \cdot 1.00$ HCl$\cdot 0.45$ $H_2O$: C, 73.75; H, 5.64; N, 10.32. Found: C, 73.69; H, 5.40; N, 10.39. FABMS 364 ($MH^+$).

Example 33

1-(4'-Methyl-4-biphenylmethyl)-5-(4-cyanobenzyl) imidazole hydrochloride salt

The title compound was prepared using the protocol described in Example 5, steps A–C using 4-iodotoluene.

Anal. Calcd. for $C_{25}H_{21}N_3 \cdot 1.00$ HCl$\cdot 0.10$ $H_2O$: C, 74.75; H, 5.57; N, 10.46. Found: C, 74.79; H, 5.37; N, 10.09. FABMS 364 ($MH^+$).

Example 34

1-(3'-Trifluoromethyl-4-biphenylmethyl)-5-(4-cyanobenzyl) idazole hydrochloride salt The title compound was prepared using the protocol described in Example 5, steps A–C using 3-trifluoomethyl iodobenzene.

FABMS 418 ($MH^+$).

Example 35

1-(4'-Trifluoromethyl-4-biphenylmethyl)-5-(4-csyanobenzyl) imidazole hydrochloride salt The title compound was prepared using the protocol described in Example 5, steps A–C using 4-trifluoromethyl iodobenzene.

Anal. Calcd. for $C_{25}H_{18}N_3F_3 \cdot 0.95$ HCl$\cdot 1.15$ $H_2O$: C, 58.97; H, 4.40; N, 8.25. Found: C, 58.92; H, 4.40; N, 8.43. FABMS 418 ($MH^+$).

Example 36

1-(3'-Chloro-4-biphenylmethyl)-5-(4-cyanobenzyl) imidazole hydrochloride salt

The title compound was prepared using the protocol described in Example 5, steps A–C using 3-chloroiodobenzene.

Anal. Calcd. for $C_{25}H_{21}N_3 \cdot 1.00$ HCl$\cdot 0.25$ $H_2O$: C, 68.00; H, 4.61; N, 9.91. Found: C, 67.95; H, 4.57; N, 10.30; FABMS 384 ($MH^+$).

Example 37

1-(4'-Chloro-4-biphenylmethyl)-5-(4-cyanobenzyl) imidazole hydrochloride salt

The title compound was prepared using the protocol described in Example 5, steps A–C using 4-chloroiodobenzene.

Anal. Calcd. for $C_{25}H_{21}N_3 \cdot 1.00$ HCl$\cdot 0.90$ $H_2O$: C, 66.03; H, 4.80; N, 9.63. Found: C, 66.09; H, 4.75; N, 9.48; FABMS 384 ($MH^+$).

Example 38

1-(2'3'-Dichloro-4-biphenylmethyl)-5-(4-cyanobenzyl)imidazoe hydrochloride salt

The title compound was prepared using the protocol described in Example 5, steps A–C using 2,3-dichloroiodobenzene.

FABMS 418 ($MH^+$).

Example 39

1-(2'4'-Dichloro-4-biphenylmethyl)-5-(4-cyanobenzyl)imidazole hydrochloride salt The title compound was prepared using the protocol described in Example 5, steps A–C using 2,4-dichloroiodobenzene.

Anal. Calcd. for $C_{24}Hl_7N_3Cl_2 \cdot 1.00$ HCl$\cdot 0.30$ $H_2O$: C, 62.64; H, 4.07; N, 9.13. Found: C, 62.64; H, 4.23; N, 8.86; FABMS 418 ($MH^+$).

Example 40

1-(2'5'-Dichloro-4-biphenylmethyl)-5-(4-cyanobenzyl)imidazole hydrochloride salt The title compound was prepared using the protocol described in Example 5, steps A–C using 2,5-dichloroiodobenzene.

Anal. Calcd. for $C_{24}H_{17}N_3Cl_2 \cdot 1.20$ HCl·0.35 $H_2O$: C, 61.55; H, 4.07; N, 8.97; Found: C, 61.53; H, 4.08; N, 9.03; FABMS 418 (MH$^+$).

Example 41

1-(3'-Trifluoromethoxy-4-biphenylmethyl)-5-(4-cyanobenzyl) imidazole hydrobromide salt The title compound was prepared using the protocol described in Example 13, steps A–C using 3-trifluoro iodobenzene.

Anal. Calcd. for $C_{25}H_{18}N_3OF_3 \cdot 1.00$ HCl.: C, 63.91; H, 4.08; N, 8.94; Found: C, 63.77; H, 3.97; N, 8.60; FAB HRMS exact mass calcd for $C_{25}H_{18}N_3OF_3$ 434.147543 (MH$^+$); found 434.148022.

Example 42

1-(2'-Fluoro-4-biphenylmethyl)-5-(4-cyanobenzyl) imidazole hydrobromide salt The title compound was prepared using the protocol described in Example 13, steps A–C using 2-fluoro iodobenzene.

Anal. Calcd. for $C_{24}H_{18}N_3F \cdot 1.20$ HBr.0.15 $H_2O$: C, 63.91; H, 4.31; N, 9.32; Found: C, 64.04; H, 4.12; N, 8.92; FABMS 368 (MH$^+$).

Example 43

1-(4-(2'-Trifluoromethylphenyl)-2-Chlorophenylmethyl)-5-(4-cyanobenzyl)imidazole hydrochloride salt The title compound was prepared using the protocol described in Example 13, steps A–C using 2-chloro-4-iodotoluene and 2-trifluoromethylbenzene boronic acid.

Anal. Calcd. for $C_{25}H_{17}N_3F_3Cl \cdot 1.00$ HCl.0.15 EtoAc: C, 61.31; H, 3.86; N, 8.38; Found: C, 61.33; H, 3.78; N, 8.15; FABMS 452 (MH$^+$).

Example 44

1-{1-(4-(2'-trifluoromethylphenyl)phenyl)ethyl}-5-(4-cyanobenzyl) imidazole hydrochloride salt Step A: 4-(2'-trifluoromethylphenyl)benzaldehyde To a solution of 4-formylbenzeneboronic acid (4.00 g, 26.7 mmol) and $Na_2CO_3$ (5.66 g, 53.4 mmol) in water (240 mL) was added p-dioxane (240 mL). This mixture was treated sequentially with 2-iodobenzotrifluoride (3.74 mL, 26.7 mmol) and palladium (II) acetate (540 mg, 2.40 mmol) and allowed to stir at ambient temperature for 24 hours. The solvent was evaporated in vacuo. To the residue was added EtOAc (400 inL) and water (300 mL). The aqueous layer was acidified to pH 2 with 1.0 N aq. HCl and the layers separated. The aqueous layer was extracted with EtOAc (2×200 mL). The organic extracts were combined, washed with brine (200 mL), 5% aq. $Na_2S_2O_3$ (200 mL), saturated NaCl (200 mL), dried ($Na_2SO_4$), and the solvent evaporated in vacuo and the residue chromatographed (Silica gel, 20–50% $CH_2Cl_2$ in hexanes) to afford the title compound.

$^1$H NMR (CDCl$_3$, 400 MHz) δ 10.09(1H, s), 7.93(2H, d, J=8.0 Hz), 7.78(1H, d, J=8.2 Hz), 7.60(1H, t, J=7.5 Hz), 7.55–7.45(3H, m) and 7.33(1H, d, J=8.0 Hz) ppm.

Step B: 1-(4-(2'-trifluoromethylphenyl)phenyl)ethanol

To a solution of 4-(2-trifluoromethylphenyl)-benzaldehyde (1.00 g, 0.40 mmol) in Et$_2$O (20 mL) at −70° C. was added methyl lithium (2.85 mL of a 1.4 M in Et$_2$O 0.40 mmol) over 10 minutes. The reaction was allowed to warm to ambient temperature and stirred for 1 hour. The reaction was quenched by dropwise addition of sat. aq. NH$_4$OH and extracted with Et$_2$O. The organic layer was washed with brine and dried(MgSO$_4$), and the solvent evaporated in vacuo. The residue was chromatographed (Silica gel, 20–50% $CH_2Cl_2$ in hexanes) to afford the title compound.

$^1$H NMR (CDCl$_3$, 400 MHz) δ 7.75(1H, d, J=7.7 Hz), ), 7.55(1H, t, J=7.4 Hz), 7.47(1H, t, J=7.4 Hz), 7.41(2H, d, J=7.9 Hz), 7.36–7.28(3H, m) and 4.98(1H, m) ppm.

Step C: 1-{1-(4-(2'-trifluoromethylphenyl)phenyl)ethyl}-5-(4-cyanobenzyl)imidazole hydrochloride salt The title compound was prepared using the protocol described in Example 5, step C using the alcohol from step B.

Anal. Calcd. for $C_{26}H_{20}N_3F_3 \cdot 1.00$ HCl.1.1 EtOAc: C, 66.52; H, 4.61; N, 8.81. Found: C, 66.74; H, 4.52; N, 8.98.

Example 45

1-(2'-Trifluoromethyl-4-biphenylpropyl)-5-(4-cyanobenzyl) imidazole

Step A: E-Ethyl-3-(4-(2'-trifluoromethylphenyl)phenyl) prop-2-enoate

To a solution of 4-(2'-trifluoromethylphenyl) benzaldehyde (1.00 g, 3.996 mmol, prepared using the protocol described in Example 44, step A) in $CH_2Cl_2$ (8.0 mL) was added (carbethoxymethylene) triphenylphosphorane (1.46 g, 4.196 mmol)and the reaction was stirred at room temperature for 16 hours. The solvent was evaporated in vacuo and the residue chromatographed (Silica gel, 2.5% EtOAc in hexanes) to afford the title compound.

$^1$HNMR (CD$_3$OD 400 MHz) δ 7.90–7.50(6H,m),), 7.40 7.35(3H,m), 6.60(1H,d, J=16.1 Hz), 4.27(2H, q, J=7.1 Hz), 1.34(3H, t, J=7.1 Hz),)ppm.

Step B: Ethyl-3-(4-(2'-trifluoromethylphenyl)phenyl)-propionoate

A solution of E-Ethyl-3-(4-(2'-trifluoromethylphenyl) phenyl)prop-2-enoate (0.444 g, 1.388 mmol) and 10% palladium on carbon (0.044 g) in ETOH (13.88 mL) was hydrogenated in a parr apparatus. The catalyst was removed by filtration through celite and the title compound obtained by solvent evaporation in vacuo.

$^1$H NMR (CD$_3$OD 400 MHz) δ 7.73(1H, d, J=7.7 Hz), 7.58(1H, t, J=7.7 Hz), 7.48(1H, t, J=7.7 Hz), 7.29(1H, d, J=7.7 Hz), 7.24 (2H, d, J=8.2 Hz), 7.19(2H, d, J=8.2 Hz), 4.10(2H, q, J=7.1 Hz), 2.96(2H, t, J=7.7 Hz), 2.65(2H, t, J=7.5 Hz) and 1.20(2H, qn, J=7.5 Hz) ppm.

Step C: 1-(2'-Trifluoromethyl-4-biphenylpropyl)-5-(4-cyanobenzyl)imidazole

The title compound was prepared using the protocol described in Example 5, steps B–C using the product from step B.

$^1$H NMR (CD$_3$OD 400 MHz) δ 7.75(1H, d, J=7.7 Hz), 7.70–7.60(3H, m), 7.52(1H, t, J=7.5 Hz), 7.33(1H, d, J=7.9 Hz), 7.21 (1H, d, J=7.6 Hz), 7.13 (2H, d, J=8.1 Hz), 6.78(1H, s), 4.03(2H, q, J=7.1 Hz), 3.86 (2H, t, J=7.5 Hz), 2.60(2H, t, J=7.5 Hz) and 1.92(2H, qn, J=7.5 Hz) ppm.

Example 46

1-(2'-N-t-Butoxycarbonylamino-4-biphenylmethyl)-5-(4-cyanobenzyl)imidazole

Step A: 4-(2'-Cyanophenyl)benzoic acid methyl ester.

To a solution of 2-bromobenzonitrile (1.00 g, 5.494 mmol), in THF (16.5 mL) at −100° C. was added t-butyl lithium (6.46 mL, of a 1.7M solution in pentane, 10.98 mmol. After 5 minutes zinc chloride(5.494 mL, of a 1M solution in THF, 5.494 mmol) was added. The reaction was stirred for 10 minutes at −78° C. and then allowed to warm to 0° C. and stirred for 1 hour. This solution was added via cannula to a solution of methyl-4-iodobenzoate (1.44 g, 5.494 mmol) and bis(triphenylphosphine) Nickel II chloride (0.359 g, 0.549 mmol) in THF (12 mL). The reaction stirred for 1 hour at 0° C. and then at ambient temperature for a further 16 hours. Saturated ammonium hydroxide solution (5 mL) was added and the mixture stirred until homogenous, extracted with EtOAc and the organic extracts washed with saturated brine, dried ($MgSO_4$) and evaporated in vacuo. The residue was chromatographed (Silica gel, 50% $CH_2Cl_2$ to 50%) EtOAc in hexanes) to afford the title compound.

$^1$H NMR ($CD_3OD$, 400 MHz) δ 8.15(2H, d, J=8.7 Hz),),7.87(1H, d, J=7.7 Hz), 7.77(1H, t, J=7.5 Hz),), 7.69(2H, d, J=8.7 Hz), 7.65–7.55(2H, m), and 3.95(3H, s) ppm.

Step B: 4-(2'-Aminomethylphenyl)hydroxymethylbenzene

To a solution of 4-(2'-cyanophenyl)benzoic acid methyl ester (0.428 g, 1.804 mmol) in tetrahydrofuran (14.3 mL) at 0° C. was added 1.0 M lithium aluminum hydride in tetrahydrofuran (3.61 mL, 3.61 mmol) over 10 minutes. The reaction was allowed to stir at ambient temperature for 3 hours, then warmed to 45° C. for 3 hours, cooled and quenched by dropwise addition of saturated $Na_2SO_4$ (0.46 mL). The reaction was diluted with diethylether, $Na_2SO_4$ was added, the mixture filtered through a pad of Celite and the filtrate evaporated in vacuo to afford the title compound.

$^1$H NMR ($CD_3OD$, 400 MHz) δ 7.47(1H, d, J=7.5 Hz), 7.42(2H, d, J=8.4 Hz), 7.40–7.15 (4H,m), 4.66(2H,s) and 3.73(2H,s) ppm.

Step C: 4-(2'-t-Butoxycarbonylaminomethylphenyl)hydroxymethylbenzene

To a solution of 4-(2'-aminomethylphenyl) hydroxymethylbenzene (0.374 g, 1.754 mmol) and triethylamine (0.269 mL, 1.929 mmol) in DMF (8.0 mL) at 0° C. was added 1-butylcarbonate (0.383 g, 1.754 mmol) in DMF (2.0 mL) over 10 minutes. The reaction was allowed to stir at ambient temperature for 16 hours. The reaction was diluted with EtOAc, washed with 10% aq. citric acid, and then sat. aq. $NaHCO_3$ and dried($Na_2SO_4$). The solvent was evaporated in vacuo and the residue chromatographed (Silica gel, EtOAc) to afford the title compound.

$^1$H NMR ($CD_3OD$, 400 MHz) δ 7.50–7.15(1H, m), 4.66 (2H,s), 4.15(2H,s) and 1.43(9H,s) ppm Step D: 1-(2'-N-t-Butoxycarbonylaminomethyl-4-biphenylmethyl)-5-(4-cyanobenzyl)imidazole The title compound was prepared using the protocol described in Example 5, step C using the product from step C.

FAB HRMS exact mass calcd for $C_{30}H_{30}N_4$ $O_2$ 479.244702 (MH$^+$); found 479.244189. Anal. Calcd. for $C_{30}H_{30}N_4$ $O_2$.0.10 $H_2O$: C, 75.29; H, 6.32; N, 11.71. Found: C, 75.20; H, 5.87; N, 11.27.

Example 47

1-(2'-Aminomethyl-4-biphenylmethyl)-5-(4-cyanobenzyl)imidazole hydrochloride salt A solution of 1-(2'-N-t-Butoxycarbonylaminomethyl-4-biphenylmethyl)-5-(4-cyanobenzyl)imidazole (43.7 mg, 0.094 mmol) in EtOAc (10 mL) was saturated with HCl gas. After 10 minutes the solvent was evaporated in vacuo to afford the title compound as a white solid.

FAB HRMS exact mass calcd for $C_{25}H_{22}N_4$ 379.192272 (MH$^+$); found 379.192525. Anal. Calcd. for $C_{25}H_{22}N_4$.0.75 HCl: C, 62.71; H, 5.21; N, 11.70. Found: C, 62.71; H, 5.14; N, 11.32.

Example 48

1-(2'-Acetylaminomethyl-4-biphenylmethyl)-5-(4-cyanobenzyl) imidazole

To a solution of 1-(2'-aminomethyl-4-biphenylmethyl)-5-(4-cyanobenzyl)imidazole hyrochloride (0.107 g, 0.237 mmol) and triethylamine (0.033 mL, 0.237 mmol) in $CH_2Cl_2$ (4.7 mL) at 0° C. was added acetic anhydride (0.383 g, 1.754 mmol). The reaction was allowed to stir at ambient temperature for 16 hours. The reaction was diluted with $CH_2Cl_2$, washed sat. aq. $Na_2CO_3$ and dried ($Na_2SO_4$). The solvent was evaporated in vacuo and the residue chromatographed (Silica gel, 3% MeOH in $CH_2Cl_2$) to afford the free base which was converted to the HCl salt.

FAB HRMS exact mass calcd for $C_{25}H_{22}N_4O$ 421.202837 (MH$^+$); found 421.203621. Anal. Calcd. for $C_{25}H_{22}N_4O$ 1.60 HCl: C, 67.72; H, 5.39; N, 11.70. Found: C, 67.58; H, 5.21; N, 11.77.

Example 49

1-(2'-Methylsulfonylaminomethyl-4-biphenylmethyl)-5-(4-cyanobenzyl)imidazole hydrochloride The title compound was prepared using the protocol described in Example 48, using methanesulfonyl chloride.

FAB HRMS exact mass calcd for $C_{26}H_{24}N_4O_2S$ 457.169823 (MH$^+$); found 457.170937. Anal. Calcd. for $C_{26}H_{24}N_4O_2S$ 1.70 HCl 0.20 EtOAc: C, 60.03; H, 5.13; N, 10.45. Found: C, 59.99; H, 4.93; N, 10.05.

Example 49

1-(2'-Ethylaminomethyl-4-biphenylmethyl)-5-(4-cyanobenzyl) imidazole hydrochloride To a solution of 1-(2'-aminomethyl-4-biphenylmethyl)-5-(4-cyanobenzyl)imidazole hydrochloride (0.100 g, 0.222 mmol) acetaldehyde (0.024 mL, 0.444 mmol) and 4A molecular sieves (300 mg) in MeOH (0.44 mL) at room temperature was added triethylamine to a pH of 7. Sodium cyanoborohydride (0.028 g, 0.444 mmol) was added and the reaction was stirred for 16 hours. The reaction was filtered through celite and the filtrate evaporated in vacuo. The residue was partitioned between $CH_2Cl_2$, and sat. aq. $Na_2CO_3$ and the organic layer separated and dried ($Na_2SO_4$). The solvent was evaporated in vacuo and the residue chromatographed (Silica gel, 3% $NH_4OH$ in Acetonitrile) to afford the free base which was converted to the HCl salt.

FAB HRMS exact mass calcd for $C_{27}H_{26}N_4$ 407.223572 (MH$^+$); found 421.223572.

Example 50

1-(2'-Phenylaminomethyl-4-biphenylmethyl)-5-(4-cyanobenzyl) imidazole hydrochloride To a slurry of 1-(2'-aminomethyl-4-biphenylmethyl)-5-(4-cyanobenzyl)imidazole hyrochloride (0.097 g, 0.216 mmol) triphenyl bismuth (0.166 g, 0.377 mmol) and copperII acetate (0.059 g, 0.323 mmol) in $CH_2Cl_2$ (0.43 mL) at room temperature was added triethylamine (0.045 mL, 0.323 mmol) and the reaction was stirred for 16 hours. Silica gel was added and the solvent evaporated in vacuo. The solid was applied to a column and chromatographed (Silica gel, 2% MeOH in $CH_2Cl_2$) to afford the free base which was converted to the HCl salt.

FAB HRMS exact mass calcd for $C_{31}H_{26}N_4$ 454.215747 ($MH^+$); found 454.212863.

Example 51

1-(2'-Glycinylaminomethyl-4-biphenylmethyl)-5-(4-cyanobenzyl) imidazole hydrochloride To a slurry of 1-(2'-aminomethyl-4-biphenylmethyl)-5-(4-cyanobenzyl)imidazole hyrochloride (0.0100 g, 0.222 mmol) N-Boc glycine (0.039 g, 0.222 mmol), triethylamine (0.093 mL, 0.666 mmol) and HOBT (0.030 g, 0.222 mmol) in $CH_2Cl_2$ (2.2 mL) at room temperature was added EDC (0.042 g, 0.222 mmol) and the reaction was stirred for 16 hours. The reaction was diluted with $CH_2Cl_2$ and washed with $NaHCO_3$ and the organic extracts dried ($Na_2SO_4$) and evaporated in vacuo. The residue was chromatographed (Silica gel, 2.5–5% MeOH in $CH_2Cl_2$) to afford the N-Boc glycinyl derivative. This material was dissolved in EtOAc (3 mL) and saturated with HCl gas. The reaction was stirred for 40 minutes at 0° C. and the solvent evaporated to afford the title compound as a white solid FABMS 436($MH^+$); $C_{27}H_{25}N_5O$; Anal. Calcd. for $C_{27}H_{25}N_5O$ 1.55 HCl 2.70 $H_2O$: C, 60.06; H, 5.96; N, 12.97. Found: C, 60.04; H, 5.96; N, 12.93.

Example 52

1-(2'-Methyl-4-biphenylmethyl)-2-chloro-5-(4-cyanobenzyl) imidazole and 1-(2'-Methyl-4-biphenylmethyl)-4-chloro 5-(4-cyanobenzyl) imidazole A solution of 1-(4-(4'-Methylbiphenylmethyl)-5-(4-cyanobenzyl)imidazole (120 mg, 0.330 mmol) in $CH_2Cl_2$ was treated with NCS (44 mg, 0.330 mmol) and the reaction stirred for 16 hours at room temperature. The solvent was evaporated in vacuo and the residue chromatographed (Silica gel, 2% MeOH in $CH_2Cl_2$) to afford a mixture of regioisomers. These were separated by preparative HPLC to afford the title compounds.

1-(2'-Methyl-4-biphenylmethyl)-2-chloro-5-(4-cyanobenzyl) imidazole;
$^1$H NMR ($CD_3OD$, 400 MHz) δ 7.54(1H, d, J=8.2 Hz), 7.27(2H, d, J=8.4 Hz), 7.25–7.10 (7H, m), 6.93(2H, d, J=8.4 Hz), 6.85(1H, s), 5.21(2H, s), 4.05(2H, s) and 2.20(3H, s)ppm.

1-(2'-Methyl-4-biphenylmethyl)-4-chloro 5-(4-cyanobenzyl) imidazole;
$^1$H NMR ($CD_3OD$, 400 MHz) δ 7.79(1H, s), 7.50(1H, d, J=8.2 Hz), 7.25–7.02 (9H, m), 7.00(2H, d, J=8.4 Hz), 5.15(2H, s), 4.05(2H, s) and 2.16(3H, s)ppm.

Example 53

1-(3'-Chloro-2-methyl-4-biphenylmethyl)-4-(4-cyanobenzyl)-imidazole hydrochloride salt Step A: Preparation of 4-trifluoromethylsulfonyloxy-3-methylbenzaldehyde To a solution of 4-hydroxy-3-methylbenzaldehyde (Aldrich; (1 g; 7.34 mmol) in 20 mL of $CH_2Cl_2$ at room temperature was added triethylamine (1.13 mL, 8.08 mmol), then triflic anhydride (1.36 mL, 8.08 mmol). After 2 h, the reaction was poured into $CH_2Cl_2$, washed with saturated $NaHCO_3$, then brine, dried, filtered, and concentrated in vacuo to provide the crude aldehyde. Column chromatography (silica gel; hexane:EtOAc 4:1) afforded the title compound as an oil.

Step B: Preparation of (3'-chlorophenyl)-3-methylbenzaldehyde

Following the procedure described for Example 13, step A, but using the product from step A above and 3-chlorobenzeneboronic acid as starting materials the title product was obtained.

Step C: Preparation of (3'-chlorophenyl)-3-methylbenzylalcohol

Following the procedure described for Example 7, step B, but using the product from step B above as starting material, the title product was obtained.

Step D: Preparation of 1-(3'-chloro-2-methyl-4-biphenylmethyl)-4-(4-cyanobenzyl)imidazole hydrochloride salt Using the alcohol from step C and following the procedure described for Example 5, step C with a subsequent purification by silica gel chromatography (EtOAc then 2% MeOH in $CHCl_3$). The first eluted material afforded the title compound after treatment with HCl and $Et_2O$.

Analysis calculated for $C_{25}H_{20}ON_3Cl•2.7HCl•0.3Et_2O$: C, 60.67; H, 4.99; N, 8.10; Found: C, 60.67; H, 4.62; N, 7.95.

Example 54

1-(3'-Chloro-2-methyl-4-biphenylmethyl)-5-(4-cyanobenzyl)imidazole hydrochloride salt Following the procedure of Example 53, step D, but collecting the later eluting material the title compound was obtained.

Analysis calculated for $C_{25}H_{20}N_3Cl•1.7HCl•0.2Et_2O$: C, 65.27; H, 5.03; N, 8.85; Found: C, 65.36; H, 5.03; N, 8.86.

Example 55

1-(3'-Trifluoromethyl-2-methyl-4-biphenylmethyl)-4-(4-cyanobenzyl)imidazole hydrochloride salt Following the procedure described for Example 53, steps B–C but using 3-trifluoromethylbenzeneboronic acid as starting materials, the title compound was obtained. It was isolated by silica gel chromatography (EtOAc then 2% MeOH in $CHCl_3$) collecting the first eluted material and then subsequent treatment with HCl and $Et_2O$.

Analysis calculated for $C_{26}H_{20}N_3F_3•1.4HCl•0.35$ EtOAc: C, 64.10; H, 4.75; N, 8.18; Found: C, 64.14; H, 4.50; N, 8.10.

Example 56

1-(3'-Trifluoromethyl-2-methyl-4-biphenylmethyl)-5-(4-cyanobenzyl)imidazole trifluoroacetic acid salt Following the procedure described for Example 53, steps B–C but using 3-trifluoromethylbenzeneboronic acid as starting materials, the title compound was obtained. It was isolated by silica gel chromatography (EtOAc then 2% MeOH in $CHCl_3$) collecting the second eluted material and then subsequent preparative HPLC purification.

Analysis calculated for $C_{26}H_{20}N_3F_3•1.35TFA•0.4H_2O$: C, 58.17; H, 3.77; N, 7.09; Found: C, 58.17; H, 3.78; N, 7.19.

Example 57

1-(3'-Methoxy-2-methyl-4-biphenylmethyl)-5-(4-cyanobenzyl)imidazole hydrochloride salt Step A: Preparation of 2-bromo-5-hydroxylmethyltoluene To a solution of 4-bromo-3-methyltenzoic acid (Aldrich; (3 g, 14 mmol) in 75 mL of THF at 0° C. was added BH$_3$.THF complex (1M in THF; 15 mL, 15 mmol). After stirring for 3 h at room temperature, 10 mL 1N NaOH was added slowly. The solution was poured into water and extracted with CHCl$_3$, washed with water then brine, dried and evaporated. Column chromatography of the product (silica gel; EtOAc) afforded the title compound as a solid.

Step B: Preparation of 4-(3'-methoxyphenyl)-3-methyl-benzylalcohol

Following the procedure described for Example 13, step A, but using the product from step A above and 3-methoxybenzene-boronic acid as starting materials the title product was obtained.

Step C: Preparation of 1-(3'-methoxy-2-methyl-4-biphenylmethyl)-5-(4-cyanobenzyl)imidazole hydrochloride salt Following the procedure described for Example 5, step C, but using the product from step B above as starting material, the title product was obtained.

Analysis calculated for C$_{26}$H$_{23}$N$_3$•1.2HCl: C, 71.41; H, 5.58; N, 9.61; Found: C, 71.34; H, 5.45; N, 9.83.

Example 58

1-(2'-Chloro-4'-fluoro-4-biphenylmethyl)-5-(4-cyanobenzyl)imidazole hydrochloride salt Step A: Preparation of 1-chloro-5-fluoro-2-trifluoromethyl-sulfonylyoxybenzene Following the procedure described for Example A, step A, but using 2-chloro-4-fluorophenol as starting materials the title product was obtained.

Step B: Preparation of 1-(2'-Chloro-4'-fluoro-4-biphenylmethyl)-5-(4-cyanobenzyl)imidazole hydrochloride salt Following the procedure described for Example 5, steps A–C, but using the product from step A above as; starting material, the title product was obtained.

Analysis calculated for C$_{24}$H$_{17}$N$_3$OClF•1.1HCl: C, 65.22; H, 4.13; N, 9.51; Found: C, 65.33; H, 4.27; N, 9.24.

Example 59

1-(2'-Ethyl-4-biphenylmethyl)-5-(4-cyanobenzyl) imidazole trifluoroacetic acid salt Following the procedure described for Example 5, steps A–C, but using 1-iodo-2-ethylbenzene as starting material, the title product was obtained.

Analysis calculated for C$_{26}$H$_{23}$N$_3$•1.35TFA•1.4H$_2$O: C, 61.93; H, 4.92; N, 7.55; Found: C, 61.96; H, 5.12; N, 7.16.

Example 60

1-(2'-(2-Propyl)-4-biphenylmethyl)-5-(4-cyanobenzyl)imidazole trifluoroacetic acid salt Following the procedure described for Example 5, steps A–C, but using 1-iodo-2-(2-propyl)benzene as starting material, the title product was obtained.

Analysis calculated for C$_{27}$H$_{25}$N$_3$•1.5TFA•0.75H$_2$O: C, 62.55; H, 4.90; N, 7.29; Found: C, 62.56; H, 4.95; N, 6.98.

Example 61

1-(2'-(2-Methyl-2-propyl)-4-biphenylmethyl)-5-(4-cyanobenzyl)imidazole hydrochloride salt Step A: Preparation of 2-(2-methyl-2-propyl)-1-trifluoromethyl-sulfonyloxybenzene Following the procedure described for Example 53, step A, but using 2-(2-methyl-2-propyl)phenol as starting materials the title product was obtained.

Step B: Preparation of 1-(2'-(2-methyl-2-propyl)-4-biphenylmethyl)-5-(4-cyanobenzyl)imidazole hydrochloride salt Following the procedure described for Example 5, steps A–C, but using the product from step A above as starting material, the title product was obtained.

Analysis calculated for C$_{28}$H$_{27}$N$_3$•1.75HCl: C, 71.64; H, 6.17; N, 8.95; Found: C, 71.71; H, 5.93; N, 8.56.

Example 62

1-(2'-Ethyl-4-biphenylmethy)-5-(4-(1H-tetrazol-5-yl))benzyl)imidazole trifluoroacetic acid salt 1-(2'-Ethyl-4-biphenylmethyl)-5-(4-cyanobenzyl) imidazole (from Example 59; 150 mg, 0.4 mmol) was dissolved in toluene (10 mL) and treated with trimethylsilylazide (0.15 mL, 1.08 mmol) and dibutyltin oxide (110 mg, 0.44 mmol). The mixture was heated at 100° C. for 16 h, cooled and the solvent removed in vacuo. Chromatography of the residue (silica gel; EtOH: NH$_4$OH: H$_2$O 20:1:1) gave an oil which was further purified by preparative HPLC to give the title compound.

FAB mass spectrum (M+H)=421.08; Analysis calculated for C$_{26}$H$_{24}$N$_6$•1.35TFA•0.15H$_2$O: C, 59.72; H, 4.48; N, 14.56; Found: C, 59.71; H, 4.42; N, 14.54.

Example 63

1-[1-(4-Cyanobenzyl)imidazol-5-ylmethoxy]-4-(2'-methylphenyl)-2-(3-N-phthalimido-1-propyl) benzene trifluoroacetic acid salt Step A: Preparation of 4-(2'-methylphenyl)phenol Following the procedure described for Example 5, step A, but 4-bromophenol 2-methylbenzeneboronic acid as starting materials the title product was obtained Step B: Preparation of 1-allyloxy-4-(2'-methylphenyl) benzene The phenol from step A (1.72 g, 9.35 mmol), CS$_2$CO$_3$ (3.6 g, 10.5 mmol) and allylbromide (0.9 mL, 10.3 mmol) in DMF (47 nmL) were stirred at room temperature for 48 h. The mixture was poured into water and extracted with EtOAc, washed with water (3×), brine, dried and evaporated to give the title compound as an oil.

Step C: Preparation of 2-allyl-4-(2-methylphenyl)phenol

To a stirred solution of BCl$_3$ (1M in p-xylene; 6.7 mL, 6.7 mmol) in chlorobenzene at −15° C. was added the allyl ether from step B (1.48 g, 6.6 mmol) in 5 mL of chlorobenzene. After 1 h at −15° C., the mixture was poured into ice/MeOH, extracted with Et$_2$O (3×), washed with saturated NaHCO$_3$, water then brine. The dried solution was evaporated to give the title compound as an oil.

Step D: Preparation of 2-allyl-1-benzyloxy-4-(2-methylphenyl)benzene

Following the procedure of step B but using benzyl bromide, the phenol from step C was converted into the title compound Step E: Preparation of 1-benzyloxy-2-(3-hidroxypropyl)-4-(2'-methylphenyl)benzene To a stirred solution of the allyl derivative from step D, (3.2 g, 10.2 mmol) in THF (40 mL) at 0° C. was added 9-BBN (0.5 M in THF; 30.6 mL, 15 mmol) and the mixture stirred for 4 h. The solution was treated with 30% $H_2O_2$/1N NaOH and after 15 minutes, poured into water and extracted with EtOAc (2×). The organic layers were washed with water, brine, dried and evaporated to give an oil. Chromatography on silica gel (hexane/EtOAc 4:1) afforded the title compound as an oil.

Step F: Preparation of 1-benzyloxy-2-(3-N-phthalimido-1-propyl)-4-(2'-methylphenyl)benzene To a stirred solution of the alcohol from step E, (1.5 g, 4.52 mmol) and triphenylphosphine (1.78 g, 5.65 mmol) in THF (30 mL) at room temperature was added dropwise a solution of DEAD (0.9 mL, 5.65 mmol) and phthalimide (731 mg, 5 mmol) in THF (5 mL). After stirring for 16 h, the mixture was concentrated in vacuo and the residue taken up in EtOAc. The solution was washed with 10% citric acid solution, saturated $NaHCO_3$, water then brine, dried and evaporated to give an oil. Column chromatography (silica gel; hexane:EtOAc 9:1) afforded the title compound as an oil.

Step G: Preparation of 2-(3-N-phthalimido-1-propyl)-4-(2'-methylphenyl)phenol

To a degassed solution of the benzylether from step F, (1.5 g, 3.3 mmol) in EtOH (30 mL) and EtOAc (5 mL) was added 300 µL of HOAc and 10% palladium hydroxide on carbon (150 mg) and this was then placed on a Parr hydrogenation apparatus at 50 psi of hydrogen. After shaking for 24 h, the mixture was filtered through celite, the solvent removed and the residue chromatographed (silica gel; hexane:EtOAc 3:1) to give the title compound as an oil.

Step H: Preparation of 1-(4-cyanobenzyl)-5-chloromethylimidazole hydrochloride

A suspension of 1-(4-cyanobenzyl)-5-hydroxymethylimidazole (Example 26, step D; 3.1 g, 14.5 mmol) in thionyl chloride (20 mL) was heated at 60° C. for 18 h. The excess thionyl chloride was removed in vacuo and the residue was azeotroped with $CHCl_3$ (3×) to give the title compound.

Step I: Preparation of 1-[1-(4-cyanobenzyl)imidazol-5-ylmethoxy]-4-(2'-methylphenyl)-2-(3-N-phthaliniido-1-propyl)benzene trifluoroacetic acid salt Following the procedure described for step B, but using the phenol from step G and 5-chloromethyl-1-(4-cyanobenzyl) imidazole hydrochloride from step H as starting materials, the title compound was obtained.

FAB mass spectrum (M+H)=567.10. Analysis calculated for $C_{36}H_{30}N_4O_3 \cdot 1.5TFA \cdot 1.0H_2O$: C, 61.98; H, 4.47; N, 7.41; Found: C, 61.91; H, 4.46; N, 7.31.

Example 64

1-(3',5'-Ditrifluoromethyl-2-methyl-4-biphenylmethyl)-5-(4-cyanobenzyl)imidazole hydrochloride salt Following the procedure described for Example 5, steps A–C, but using 4-bromo-3-methylbenzoic acid and 3,5-ditrifluoromethylbenzeneboronic acid as starting materials, the title product was obtained.

Analysis calculated for $C_{27}H_{19}N_3 \cdot 1.0HCl \cdot 0.25H_2O$: C, 60.00; H, 3.82; N, 7.78; Found: C, 59.91; H, 3.74; N, 7.75.

Example 65

1-(3',5'-Chloro-2-methyl-4-biphenylmethyl)-5-(4-cyanobenzyl)imidazole hydrochloride salt Following the procedure described for Example 5, steps A–C, but using 4-bromo-3-methylbenzoic acid and 3,5-dichlorobenzeneboronic acid as starting materials, the title product was obtained.

Analysis calculated for $C_{25}H_{19}N_3 Cl_2 \cdot 1.0HCl \cdot 1.5H_2O$: C, 60.56; H, 4.68; N, 8.47; Found: C, 60.40; H, 4.83; N, 8.23.

Example 66

1-(3',5'-Dimethyl-2-methyl-4-biphenylmethyl)-5-(4-cyanobenzyl)imidazole hydrochloride salt Following the procedure described for Example 5, steps A–C, but using 4-bromo-3-methylbenzoic acid and 3,5-dimethylbenzeneboronic acid as starting materials, the title product was obtained.

Analysis calculated for $C_{27}H_{25}N_3 \cdot 1.0HCl$: C, 75.77; H, 6.12; N, 9.82; Found: C, 75.66; H, 6.10; N, 9.71.

Example 67

1-(3-(N-Boc-aminomethyl)-4-biphenylmethyl)-5-(4-cyanobenzyl)-imidazole

Step A: Preparation of 4-hydroxymethyl-biphenyl-3-carbaldehyde

To a solution of 4-biphenylmethanol (0.368 g, 2 mmol) in ether (25 mL) and TMEDA (1.21 mL, 8 mmol), at 0° C. was added n-butyllithium (2.5N hexanes; 3.2 mL, 8 mmol). The solution was then heated at reflux for 1 h, cooled to −60° C. and CuCN (0.2 g, 2.2 mmol) added. After 30 minutes, the solution was cooled to −78° C. and N-formylpiperidine (1.11 mL, 10 mmol) was then added dropwise and stirring was continued for 1 h. The mixture was then warmed to −10° C., quenched with saturated $NH_4Cl$, extracted with ether washed with brine, dried and the solvent removed in vacuo. Chromatography of the residue (silica gel; hexane:EtOAc 4:1) afforded the title compound as a colorless oil.

Step B: Preparation of 4-hydroxymethyl-biphenyl-3-carbaldehyde O-methyl-oxime

A solution of the aldehyde from step A (0.13 g, 0.61 mmol), methoxylamine hydrochloride (61 mg, 0.735 mmol) and pyridine (2 mL) in EtOH (10 mL) was heated at reflux for 16 h. Further portions of methoxylamine hydrochloride (61 mg, 0.735 mmol) and pyridine (2 mL) were added and heating was continued for 24 h. The solution was cooled, diluted with EtOAc, extracted with water (2×) then brine, dried and concentrated to give the title compound as an oil. This was used as such in the next step.

Step C: Preparation of 3-aminomethyl-biphenyl-4-methanol

To a solution of the oxime from step B (0.51 g, 2.1 mmol) in THF (15 mL) at 0° C. was added $BH_3.THF$ (1M in hexane; 8 mL, 8 mmol) and the resulting solution was stirred at room temperature for 16 h then heated to reflux for 24 h. The solution was cooled to 0° C. and 1N NaOH (10 mL) was added slowly. After 1 h, the mixture was diluted with water, extracted with EtOAc (3×), washed with brine, dried and evaporated to give the title compound as an oil. This was used as such in the next step.

Step D: Preparation of 3-N-Boc-aminomethyl-biphenyl-4-methanol

To a solution of the amine from step C (0.39 g, 1.8 mmol) and $Et_3N$ (0.255 mL, 1.8 mmol) in DMF (10 mL) was added Boc-anhydride (0.4 g, 1.8 mmol) and the mixture was stirred for 16 h. The solution was diluted with water, extracted with EtOAc (3×) and the combined organic layers were then extracted with saturated $NaHCO_3$ then brine, dried and evaporated. Chromatography of the residue (silica gel; hexane:EtOAc 3:1) afforded the title compound as a solid.

Step F: Preparation of 3-(N-Boc-aminomethyl)-4-biphenylmethyl bromide

A solution of the alcohol from step D (0.157 g, 0.5 mmol), triphenylphosphine (0.191 g, 0.75 mmol,) and CBr$_4$ (0.249 g, 0.75 mmol) in THF (15 mL) was stirred at room temperature for 16 h. The solvent was removed in vacuo and EtOAc was added to the residue. Filtration removed the insoluble material and the EtOAc solution was washed with water then brine, dried and evaporated. Purification of the residue on silica gel, eluting with hexane:EtOAc 12:1, afforded the title compound.

Step G: Preparation 1-(3-(N-Boc-aminomethyl)-4-biphenylmethyl)-5-(4-cyanobenzyl)imidazole Following the procedure of Example 1, step B but using the bromide from step G as starting material, the title compound was obtained as a solid.

Fab mass spectrum (M+H)=479.12; Analysis calculated for C$_{30}$H$_{30}$N$_4$O$_2$•0.05CHCl$_3$: C, 74.41; H, 5.67; N, 11.38; Found: C, 74.48; H, 6.25; N, 11.56.

Example 68

1-(3-Aminomethyl-4-biphenylmethyl)-5-(4-cyanobenzyl)imidazole dihydrochloride salt 1-(3-(N-Boc-aminomethyl)-4-biphenylmethyl)-5-(4-cyanobenzyl)imidazole from Example 67 was dissolved in EtOAc 0° C. and treated with HCl gas. The solvent was removed to give the title compound.

Fab mass spectrum (M+H)=379.16.

Example 69

1-(4-Cyanobenzyl)-2-methyl-5-(2'-methylbiphenyl-4-yloxy)imidazole trifluoroacetate salt Step A: Methyl N-(cyanomethyl)ethanimidate Finely grounded aminoacetonitrile hydrochloride (21 g) was stirred in a solution of chloroform (200 mL) saturated with ammonia gas for 10–15 minutes. The slurry was filtered through a plug of Celite. The filtrate was concentrated, and the residue distilled (36–40° C., 0.1 mmHg) to provide aminoacetonitrile as clear, colorless oil. Aminoacetonitrile (14 g) was added at a rate of I mL/min to a boiling mixture of trimethyl orthoacetate (200 mL), concentrated sulfuric acid (5 drops), and anhydrous sodium sulfate (20 g), with removal of distillate. The resultant mixture was heated for additional 30 minutes, filtered through Celite, and concentrated. The residue was distilled (50–60° C., 0.1 mmHg) to provide methyl N-(cyanomethyl)ethanimidate as clear, colorless oil. The ethanimidate was stored under dry argon at −10° C.

$^1$H NMR (CDCl$_3$ 300 MHz) δ 4.11 (2H, s), 3.66 (3H, s), 1.97 (3H, s) ppm.

Step B: 5-(4-Bromophenyloxy)-2-methylimidazole

Using procedure described for the preparation of 5-(4-cyanophenyloxy)imidazole in Example 17, Step A, but substituting 4-bromophenol for 4-cyanophenol, methyl N-(cyanomethyl) ethanimidate for methyl N-(cyanomethyl) methanimidate, and after heating the resultant mixture at 100° C. for 4 hours, 5-(4-bromophenyloxy)-2-methylimidazole was prepared:

$^1$H NMR (DMSO-d$_6$ 300 MHz) δ 7.45 (2H, d, J=8.8 Hz), 6.93 (2H, d, J=8.8 Hz), 6.91 (1H, s) and 2.22 (3H, s) ppm.

Step C: 5-(4-Bromophenyloxy)-1-(4-cyanobenzyl)-2-methylimidazole

To a cold (−78° C.) solution of 5-(4-bromophenyloxy)-2-methylimidazole (2.06 g, 8.14 mmol) in THF (30 mL), a solution of MeLi in diethyl ether (1.4 M, 8.96 mmol) was added. The resultant mixture was stirred at −78° C. for 1 hour, and a solution of 4-cyanobenzyl bromide (1.68 g, 8.55 mmol) in THF (3 mL) was added. The mixture was allowed to warm up to room temperature, stirred overnight, and concentrated under vacuum. The residue was partitioned between water and a 9:1 mixture of methylene chloride and methanol. The organic extract was washed with brine, dried (anhydrous sodium sulfate), filtered, and concentrated under vacuum. The residue was subjected to column chromatography on silica gel eluting with a mixture of chloroform and acetone (8:2 v/v). Two alkylation products were isolated. $^1$H NMR NOE experiments indicated that the major product to be 5-(4-bromophenyloxy)-3-(4-cyanobenzyl)-2-methylimidazole, and the minor product to be desired 5-(4-bromophenyl-oxy)-1-(4-cyanobenzyl)-2-methylimidazole.

$^1$H NMR (minor isomer; CDCl$_3$ 300 MHz) δ 7.62 (2H, d, J=8.8 Hz), 7.39 (2H, d, J=9.0 Hz), 7.16 (2H, d, J=8.8 Hz), 6.89 (2H, d, J=9.0 Hz), 6.54 (1H, s), 4.98 (2H, s), and 2.30 (3H, s) ppm.

Step D: 1-(4-Cyanobenzyl)-2-methyl-5-(2'-methylbiphenyl-4-yloxy)-imidazole trifluoroacetate salt The title compound was prepared as a white solid using the protocol described in Example 19—Step D, substituting 5-(4-bromo-phenyloxy)-1-(4-cyanobenzyl)imidazole with 5-(4-bromophenyl-oxy)-1-(4-cyanobenzyl)-2-methylimidazole, phenyl boronic acid with o-tolylboronic acid, and stirring the reaction mixture at 100° C. for 18 hours.

Anal. Calcd for C$_{25}$H$_{21}$N$_3$O•1.10 TFA•0.95 H$_2$O: C, 62.59; H, 4.63; N, 8.05. Found: C, 62.61; H, 4.66; N, 7.75. $^1$H NMR (CDCl$_3$ 300 MHz) δ 6.68 (1H, s), 5.04 (2H, s), 2.31 (3H, s), and 2.23 (3H, s) ppm.

Example 70

5-(4-Cyanobenzyl)-1-(3-cyano-2'-trifluoromethylbiphenyl-4-ylmethyl)-imidazole hydrochloride salt Step A: 3-Cyano-4-methyl-2'-trifluoromethylbiphenyl The title compound was prepared as a white solid using the protocol described in Example 19—Step D, substituting 5-(4-bromophenyloxy)-1-(4-cyanobenzyl)imidazole with 2-methyl-5-iodobenzonitrile, phenyl boronic acid with o-trifluoromethylboronic acid, and stirring the reaction mixture at 100° C. for 18 hours.

$^1$H NMR (CDCl$_3$ 300 MHz) δ 7.8–7.2 (7H, m) and 2.61 (3H, s) ppm.

Step B: 4-Bromomethyl-3-cyano-2'-trifluoromethylbiphenyl

A mixture of 3-cyano-4-methyl-2'-trifluoromethylbiphenyl (420 mg, 1.61 mmol), N-bromosuccinimide (286 mg, 1.61 mmol), AIBN (10 mg), and carbon tetrachloride (20 mL) was refluxed for 1 hour. The resultant mixture was concentrated, and the residue subjected to column chromatography on silica gel eluting with a mixture of ethyl acetate in hexane (7.5 to 92.5 v/v). Collection and concentration of appropriate fractions provided the title compound.

$^1$H NMR (CDCl$_3$ 300 MHz) δ 7.8–7.2 (7H, m) and 4.69 (2H, s) ppm.

Step C: 5-(4-Cyanobenzyl)-1-(3-cyano-2'-trifluoromethylbiphenyl-4-ylmethyl)-imidazole hydrochloride salt The title compound was prepared as a white solid using the protocol described in Example 1—Step B, substituting 4-chloromethyl-biphenyl with 4-bromomethyl-3-cyano-2'-trifluoromethylbiphenyl.

Anal. Calcd for C$_{26}$H$_{17}$N$_4$ F$_3$•1.50 HCl•1.45 H$_2$O: C, 59.68; H, 4.12; N, 10.71. Found: C, 59.74; H, 4.12; N, 10.53.

Example 71

2-Amino-5-(biphenyl-4-ylmethyl)-1-(4-cyanobenzyl)imidazole

Step A: N-Methoxy-N-methyl 2-(N-tert-butyloxycarbonylamino)-2-(biphenyl-4-ylmethyl)acetamide To a cold (0° C.) solution of N-Boc 4-biphenylalanine (2.5 g, 7.33 mmol) and N-methylmorpholine (0.96 mL, 8.79 mmol) in ethyl acetate (20 mL), isobutyl chloroformate (1.04 mL, 8.06 mmol) was added. The resultant mixture was stirred at 0° C. for 30 min. N,N-Dimethyl-hydroxyamine hydrochlori(e (0.86 g, 8.79 mmol) and N-methylmorpholine (0.96 mL, 8.79 mmol) was added, and the resultant mixture was stirred at room temp. overnight. The product mixture was diluted with ethyl acetate (100 mL). The organic extract was washed with brine, dried over anhydrous magnesium sulfate, filtered, and concentrated. The residue was subjected to column chromatography on silica gel eluting with 40% ethyl acetate in hexane. Collection and concentration of appropriate fractions provided the title compound as white solid.

$^1$H NMR (CDCl$_3$ 300 MHz) δ 7.6–7.2 (9H, m), 5.2 (1H, br s), 5.0 (1H, br s), 3.69 (3H, s), 3.19 (3H, s), 3.0 (2H, m), and 1.39 (9H, s).

Step B: N-Methoxy-N-methyl 2-[(N-tert-butyloxycarbonyl)-(N-4-bromobenzyl)amino]-2-(biphenyl-4-ylmethyl)acetamide To a cold (−78° C.) solution of N-methoxy-N-methyl 2-(N-tert-butyloxycarbonylamino)-2-(biphenyl-4-ylmethyl)acetamide (2.25 g, 5.86 mmol) in THF (60 mL), a solution of sodium bis(trimethylsilyl)amide in THF (1 M, 6.44 mL, 6.44 mmol) was added. The resulting mixture was stirred at −78° C. for 1 hour. A solution of 4-bromobenzyl bromide (1.61 g) in THF (5 mL) was added, and the resultant mixture was allowed to warm up to room temp, and stirred overnight. The product mixture was diluted with diethyl ether. The organic extract was washed with brine, dried over magnesium sulfate, filtered, and concentrated under vacuum. The residue was subjected to column chromatography on silica gel eluting with 20% ethyl acetate in hexane. Collection and concentration of appropriate fractions provided the title compound.

Step C: 2-Amino-5-(biphenyl-4-ylmethyl)-1-(4-bromobenzyl)-imidazole

To a cold (−40° C.) slurry of LiAlH$_4$ in anhydrous diethyl ether (50 mL), a solution of N-Methoxy-N-methyl 2-[(N-tert-butyloxy-carbonyl)-(N-4-bromobenzyl)amino]-2-(biphenyl-4-ylmethyl)acetamide (2.11 g, 3.82 mmol) in THF (10 mL) was added. The resultant mixture was stirred at −40° C. for 10 min. and allowed to warm up to 0° C. The mixture was then cooled back to −40° C., and quenched with aqueous KHSO$_4$ solution with temperature of the mixture maintained below −30° C. The resultant mixture was diluted with diethyl ether and stirred at room temp for 30 min. The ethereal solution was isolated, washed with brine, dried over anhydrous magnesium sulfate, filtered, and concentrated under vacuum to provide a foamy product.

Without further purification, 0.6 g of the aldehyde obtained from the above procedure was dissolved in dichloromethane (10 mL) and treated with trifluoroacetic acid (2 mL) at room temperature for 15 min. The resulting mixture was concentrated under vacuum. The residue was dissolved in a mixture of absolute ethanol and dichloromethane (8 mL, 5:1 v/v; pH adjusted to about 4–5 with addition of diisopropylethylamine), treated with cyanamide (0.16 g, 3.69 mmol), and heated under reflux for 3 h. The resultant mixture was concentrated, and the residue subjected to column chromatography on silica gel eluting with a 1:1 mixture of 5% methanol in chloroform and chloroform saturated with ammonia gas. Collection and concentration of appropriate fractions provided the title aminoimidazole as white solid.

$^1$H NMR (CDCl$_3$ 300 MHz) δ 7.6–7.1(11H, m), 6.79 (2H, d, J=8.5 Hz), 6.59 (1H, s), 4.73 (2H, s), 3.81 (2H, s), and 3.72 (2H, br s) ppm. FAB MS 418/420 (MH$^+$).

Step D: 2-Amino-5-(biphenyl-4-ylmethyl)-1-(4-cyanobenzyl)imidazole

A mixture of 2-amino-5-(biphenyl-4-ylmethyl)-1-(4-bromo-benzyl)imidazole (114 mg, 0.27 mmol), anhydrous zinc cyanide (19 mg, 0.16 mmol), and anhydrous dimethylfomamide (2 mL) was purged with argon for 20 minutes. Tetrakis(triphenylphosphine)palladium(0) (32 mg, 0.028 mmol) was added, and the resultant solution was stirred under argon at 80° C. for 36 hours. The product mixture was concentrated under vacuum, and the residue subjected to column chromatography on silica gel eluting with a 1:1 mixture of 10% methanol in chloroform and chloroform saturated with ammonia gas. Collection and concentration of appropriate fractions provided the title aminoimidazole as white solid.

Anal. Calcd for C$_{24}$H$_{20}$N$_4$•0.10 CHCl$_3$: C, 76.91; H, 5.38; N, 14.89. Found: C, 77.04; H, 5.47; N, 14.78.

Example 72

2-Amino-1-(biphenyl-4-ylmethyl)-5-(4-cyanobenzyl)imidazole trifluoroacetate salt Step A: N-Methoxy-N-methyl 2-(N-tert-butyloxycarbonylamino)-2-(4-bromobenzyl)acetamide The title compound was prepared as a white solid using the protocol described in Example 71—Step A, substituting N-Boc 4-biphenyl-alanine with N-Boc 4-bromophenylalanine.

$^1$H NMR (CDCl$_3$ 300 MHz) δ 7.39 (2H, J 8.5 Hz, d), 7.04 (2H, J 8.5 Hz, d), 5.2 (1H, br s), 4.9 (1H, br s), 3.69 (3H, s), 3.17 (3H, s), 2.9 (2H, m), and 1.39 (9H, s).

Step B: N-Methoxy-N-methyl 2-[(N-tert-butyloxycarbonyl)-(N-biphenyl-4-ylmethyl)amino]-2-(4-bromobenzyl)acetamide The title compound was prepared as a white solid using the protocol described in Example 71—Step B, substituting N-methoxy-N-methyl 2-(N-tert-butyloxycarbonylamino)-2-(biphenyl-4-ylmethyl)-acetamide with N-Methoxy-N-methyl 2-(N-tert-butyloxycarbonylamino)-2-(4-bromobenzyl)acetamide, and 4-bromobenzyl bromide with biphenyl-4-ylmethyl iodide.

Step C: 2-Amino-1-(biphenyl-4-ylmethyl)-5-(4-bromobenzyl)-imidazole

The title compound was prepared as a white solid using the protocol described in Example 71—Step C, substituting N-Methoxy-N-methyl 2-[(N-tert-butyloxy-carbonyl)-(N-4-bromobenzyl)amino]-2-(biphenyl-4-ylmethyl)acetamide with N-Methoxy-N-methyl 2-[(N-tert-butyloxycarbonyl)-(N-biphenyl-4-ylmethyl)amino]-2-(4-bromobenzyl)-acetamide.

$^1$H NMR (CDCl$_3$ 300 MHz) δ 7.6–7.3 (8H, m), 7.04–6.97 (4 H, m), 6.53 (1H, s), 4.78 (2H, s), 3.83 (2H, br s), and 3.76 (2H, s) ppm. FAB MS 418/420 (MH$^+$).

Step D: 2-Amino-1-(biphenyl-4-ylmethyl)-5-(4-cyanobenzyl)-imidazole trifluoroacetate salt The title compound was prepared as a white solid using the protocol described in Example 71—Step D, substituting 2-Amino-5-(biphenyl-4-ylmethyl)-1-(4-bromobenzyl) imidazole with 2-amino-1-(biphenyl-4-ylmethyl)-5-(4-bromobenzyl)imidazole.

Anal. Calcd for C$_{24}$H$_{20}$N$_4$•1.25 TFA: C, 62.78; H, 4.22; N, 11.05. Found: C, 62.93; H, 4.04; N, 10.68.

Example 73

1-(3-Butylbiphenyl-4-ylmethyl)-5-(4-cyanobenzyl)-imidazole hydrochloride

Step A: (N-tert-butyl)-4-biphenylcarboxamide

To a 1 L round bottomed flask with a stirring bar and a drying tube was added 4-biphenylbenzoic acid (35.14 g, 177.26 mmol), $CH_2Cl_2$ (500 mL) and oxalyl chloride (17.18 mL, 196.96 mmol). To this well stirred mixture was added 10 drops of DMF. This mixture was stirred at ambient temperature for 5 h. The solvent and excess oxalyl chloride were removed in vacuo and the solid acid chloride was redissolved in fresh $CH_2Cl_2$ (500 mL). This solution was cooled to 0° C. and tert-butylamine (23.28 mL, 221.58 mmol), $Et_3N$ (30.88 mL, 221.58 mmol) and 4-DMAP (0.20 g) were added sequentially. The cooling bath was allowed to expire and the mixture was stirred at ambient temperature for 18 h. The reaction mixture was diluted with an equal volume of $CHCl_3$ and this solution was washed successively with 1N HCl, $NaHCO_3$ solution and brine. Drying ($MgSO_4$), filtration and removal of the solvent in vacuo gave an off white solid. This material was triturated with $Et_2O$ (100 mL) and collected on a frit and dried in vacuo to afford the title compound.

$^1$H NMR (CDCl$_3$) δ 1.49 (9H,s), 5.98 (1H, br s), 7.38 (1H, m), 7.45 (2H, t, j=6 Hz), 7.62 (4H, m), 7.80 (2H, d, j=7 Hz).

Step B: (N-tert-butyl)-3-(1-hydroxybutylyl)-4-biphenylcarboxamide

To three necked, 500 mL, oven dried round bottomed flask with a stirring bar, argon inlet, low temperature thermometer and a septum was added (N-tert-butyl)-4-biphenylcarboxamide (5.00 g, 19.66 mmol) and dry THF (200 mL). This solution was cooled to −78° C. and n-butyllithium (16.12 mL of a 2.5M solution in hexane, 40.30 mmol) was added with a syringe at dropwise so that the temperature did not exceed −65° C. The cooling bath was replaced with an ice-$H_2O$ bath and the reaction was allowed to warm to 0° C. and stir 45 min. The solution was recooled to −78° C. and butyraldehyde (1.80 mL, 20.00 mmol) was added with a syringe. This mixture was warmed to 5° C. during which time the mixture became homogenous. The mixture was poured into 10% aqueous citric acid and extracted with EtOAc. The organic fraction was washed with aqueous $NaHCO_3$ solution and brine. Drying ($MgSO_4$), filtration and removal of the solvent in vacuo gave a colorless foam. This material was chromatographed on silica gel using 15% EtOAc in hexane as eluant to afford the title compound.

$^1$H NMR (CDCl$_3$) δ 0.95 (3H, t, j=7.5 Hz), 1.36 (1H, m), 1.49 (9H, s), 1.50 (1H, m), 1.79 (1H, m), 1.95 (1H, m), 4.58 (1H, m), 4.75 (1H, q, j=7 Hz), 6.00 (1H, br s), 7.38 (1H, m), 7.47 (4H, m), 7.59 (3H, m).

Step C: (N-tert-butyl)-3-butyl-4-biphenylcarboxamide

To 500 mL Parr flask was added (N-tert-butyl)-3-(1-hydroxybutyl)-4-biphenylcarboxamide (3.50 g, 10.75 mmol), abs EtOH (125 mL) and 10% palladium on carbon (3.50 g). This mixture was hyrogenolyzed at 60 psig and ambient temperature for 48 h. The catalyst was removed by filtration on a celite pad and the solvent was removed in vacuo. This material was chromatographed on silica gel using 10% EtOAc in hexane as eluant to afford the title compound as a white crystalline solid.

$^1$H NMR (CDCl$_3$) δ 0.94 (3H, t, j=7.5 Hz), 1.39 (2H, m), 1.48 (9H, s), 1.63 (2H, m), 2.83 (2H, m), 5.60 (1H, br s), 7.38 (1H, m), 7.47 (4H, m), 7.59 (3H, m).

Step D: 2-Chloroethyl 3-butyl-4-phenylbenzoate

To a 200 mL round bottomed flask with a stirring bar and a reflux condenser was added (N-tert-butyl)-3-butyl-4-biphenylcarboxamide (3.17 g, 10.24 mmol), ethylene glycol (25 mL) and 12N HCl (25 mL). This mixture was heated at reflux 72 h. The cooled mixture was extracted with EtOAc and the EtOAc extracts were combined, washed with $H_2O$ (3×) and brine. Drying ($MgSO_4$), filtration and removal of the solvent in vacuo gave an oil. This material was chromatographed on silica gel using 30% EtOAc in hexane as eluantto afford the title compound as an oil.

$^1$H NMR (CDCl$_3$) δ 0.95 (3H, T, J=6.4 Hz), 1.41 (2H, m), 1.65 (2H, m), 3.04 (2H, dd, j=5.6, 1.0 Hz), 3.82 (2H, t, j=5.6 Hz), 4.58 (2H, t, j=5.6), 7.38 (1H, m), 7.47 (3H, m), 7.62 (2H, m), 8.02 (1H, d, j=8.9 Hz).

Step E: 2-Butyl-4-phenylbenzenemethanol

To a 100 mL round bottomed flask with a stirring bar and an argon inlet was added 2-chloroethyl 3-butyl-4-phenylbenzoate (570 mg, 1.80 mmol), THF (9 mL) and LiBH$_4$ (9 mL of a 2M solution in THF, 18 mmol). This mixture was heated at reflux for 18 h. The cooled reaction mixture was treated with 1N HCl and extracted with EtOAc. The combined EtOAc extracts were washed with $H_2O$ and brine. Drying ($MgSO_4$), filtration and removal of the solvent in vacuo gave an oil. This material was chiromatographed on silica gel using 20% EtOAc in hexane as eluant to afford the title compound as a crystalline solid.

$^1$H NMR (CDCl$_3$) δ 0.97 (3H, t, j=7.3), 1.41 (2H, m), 1.59 (2H, m), 2.76 (2H, dd, j=5.6, 1.0 Hz), 4.77 (2H, s), 7.35 (1H, m), 7.44 (5H, m), 7.58 (2H, m).

Step F: 2-Butyl-4-phenylbenzenemethyl bromide

To a 200 mL round bottomed flask with a stirring bar and an argon inlet was added NBS (675 mg, 3.8 mmol) in 25 ml $CH_2Cl_2$. This solution was cooled to 0° C. and was added methylsulfide (0.33 ml, 4.55 mmol). The resulting suspension was cooled to −20° C. and was added and solution of 2-butyl-4-phenylbenzenemethanol (608 mg, 2.53 mmol) in 15 ml $CH_2Cl_2$. The reaction mixture was stirred at 0° C. for 3 h. Poured the solution mixture in 200 ml ice. separated the layers, $CH_2Cl_2$ layer was washed with H2O and brine, dried ($MgSO_4$), filtration and removed solvent in vacuo to afford the title product as an oil.

$^1$H NMR (CDCl$_3$) δ 0.98 (t, 3H), 1.45 (m, 2H), 1.69 (m, 2H), 2.79 (m, 2H), 4.6 (s, 2H), 7.36 (m, 1H), 7.43 (m, 4H), 7.58 (d, J=7.32, 2H).

Step G: 1-(3-Butylbiphenyl-4-ylmethyl)-5-(4-cyanobenzyl)-imidazole hydrochloride To a 50 mL round bottomed flask with a stirring bar and an argon inlet was added 2-Butyl-4-phenylbenzenemethyl bromide (750 mg, 1.70 mmol), and 1-trityl-4-(4-cyanobenzyl) imidazole (638 mg, 1.5 mmol) in $CH_3CN$ (12 mL). The mixture was refluxed for 24 hours. The solvent was evaporated in vacuo. The residue was dissolved in methanol (10 mL), healed at reflux for 4 hour, removal of solvent in vacuo. The residue was partitioned between EtOAc and sat. aq. $NaHCO_3$ solution. The organic layer was dried, ($MgSO_4$) and the solvent evaporated in vacuo. The residue was chromatographed (Silica gel, 3% 2-propanol in CHCl3). The amine was converted to the HCl salt by treatment with 4.0M HCl in 1,4 dioxane. Triturated with EtOAc to afford a white solid.

$^1$H NMR (DMSO-d6, 400 MHz) δ 0.90(t, 3H), 1.28(m, 2H), 1.45(m, 2H), 2.42(m, 2H), 4.09(s, 2H), 5.14(s, 2H), 6.94(d, J=8.06 Hz, 1H), 7.26(m, 1H), 7.40–7.49(m, 7H), 7.56(d, J=6.96 Hz, 2H), 7.68(d, J=7.87 Hz, 2H), 8.38(br, s 1H).

Example 74

1-(3-Propylbiphenyl-4-ylmethyl)-5-(4-cyanobenzyl)-imidazole hydrochloride

Title compound was prepared using the procedure described in Example 73 substituting propionaldehyde for butyraldehyde in step B.

$^1$H NMR (DMSO-d6, 400 MHz) δ 0.91 (t, 3H), 1.46–1.51 (m, 2H), 2.5(m, 2H), 4.16(s, 2H), 5.44(s, 3H), 6.69(d, J=7.6 Hz, 1H), 7.31–7.39(m, 4H), 7.44–7.48(m, 3H), 7.59–7.63 (m, 3H), 7.69(d, J=8.05 Hz, 2H), 9.05(br, s 1H).

Example 75

1-(4-Cyanobenzyl)-5-[(3-fluoro-4-biphenyl)methyl] imidazole trifluoroacetate salt Step A: 1-(4-Cyanobenzyl)-5-[1-chloro-(3-fluoro-4-biphenyl)methyl]imidazole The alcohol from Example 28 (380 mg. 1 mmol) was dissolved in thionyl chloride (500 μl) and the solution was stirred at room temperature for 4 hours and then evaporated solution in vacuo to afford title compound.

Step B: 1-(4-Cyanobenzyl)-5-[(3-fluoro-4-biphenyl)methyl] imidazole trifluoroacetate salt The chloride from step A was hydrogenolyzed in absolute ethanol (10 mL) over 10% Pd/C (50 mg) in a Parr apparatus at 40 psi (initial) for 6 days. The catalyst was filtered off, washed well with EtOH and the solvent was evaporated. The residue was chromatographed (silica gel, 2–5% MeOH—CHCl3) and further purified by preparative HPLC. (gradient elution, 95:5 to 5:95% $H_2O$—$CH_3CN$ containing 0.1% TFA) to afford the title compound as a very hygroscopic white solid.

FAB MS 368.13 (MH$^+$); H$^1$ NMR (CD$_3$OD, 400 MHz) δ 4.10 (2H,s) 5.54 (2H,s), 6.88 (H,dd, J=11.6 and 1.6 Hz), 6.97 (H,dd, J=11.6 and 1.6 Hz), 7.23 (2H,d, J=8.8 Hz), 7.30 (H,t, J=8 Hz), 7.30–7.49 (5H,m), 7.52 (H, brs), 7.64 (2H,dd, J=6.4 and 1.6 Hz), 9.07 (H, brs)ppm.

Example 76

1-(4-Biphenylmethyl)-4-(4-cyanobenzyl-2-methylimidazole trifluoroacetate salt Step A: 1-Trityl-4-(4-cyanobenzyl)-2-methylimidazole The title compound was prepared using the protocol described in Example 16, Step C using 1-trityl-4-iodo-2-methylimidazole.

FAB MS 440.27 (MH$^+$); H$^1$ NMR (CDCl$_3$, 400 MHz) δ 1.61 (3H,s), 3.87 (2H,s), 6.45 (H,s), 7.09–7.15 (5H,m), 7.3–7.36 (12H,m), 7.54 (2H,d, J=8 Hz) ppm.

Step B: 1-(4-Biphenylmethyl)-4-(4-cyanobenzyl-2-methylimidazole trifluoroacetate salt The title compound was prepared using the protocol described in Example 2 using the product from Step A above but purified as in Example 3, Step B to give the product as a very hygroscopic white solid.

FAB MS 364.09 (MH$^+$); H$^1$ NMR (CD$_3$OD, 500 MHz) δ 2.62 (3H,s), 4.12 (2H,s), 5.36 (2H,s), 7.33 (H,s), 7.35–7.55 (13H,m) ppm.

Example 77

1-(4-Cyanobenzyl)-5-[1-(4-biphenyl)-1-hydroxy]ethyl-2-methylimidazole

Step A: 1-Trityl-4-[1-(4-biphenyl)-1-hydroxy]ethyl-2-methylimidazole

A 1.0M solution of EtMgBr in THF (4 mL, 4 mmol) was added to a solution of 1-trityl-4-iodo-2-metylimidazole (1.8 g, 4 mmol) in dry $CH_2Cl_2$ (8 mL) at room temperature. After 1 hour a solution of 4-acetylbiphenyl (780 mg, 4 mmol) in dry $CH_2Cl_2$ (4 mL) was added and stirring at room temperature was continued for 16 hours. The reaction mixture was quenched with sat. NH$_4$Cl and then the product was extracted into CHCl$_3$, dried ancl the solvent was evaporated. The residue was chromatographed (silica gel 0.5–10% MeOH—CHCl$_3$) and further purified by crystallization from CHCl$_3$-hexane to afford title compound, mp 231–232° C.

FAB MS 521.25 (MH$^+$); H$^1$ NMR (CDCl$_3$, 400 MHz) δ 1.60 (3H,s), 1.76 (3H,s), 6.65 (H,s), 7.13–7.18 (6H,m), 7.30–7.36 (10H, m), 7.42 (2H, t, J=7.2 Hz), 7.51 (4H,s), 7.57 (2H,dd, J=8.4 and 1.2 Hz) ppm.

Step B 1-(4-Cyanobenzyl)-5-[1-(4-biphenyl)-1-hydroxy] ethyl-2-methylimidazole

The title compound was prepared using the protocol described in Example 5, Step C using the product from Step A above and the corresponding amount of 4-cyanobenzyl alcohol. The residue was chromatographed (silica gel, 1.2–5.0% MeOH—CHCl$_3$) to yield the title compound.

FAB MS 394.16 (MH$^+$); H$^1$ NMR (CDCl$_3$, 500 MHz) δ 1.95 (3H,s), 2.18 (3H,2), 4.98 (H,d, J=17.6 Hz) 5.22 (H,d, J=17.6 Hz), 6.72 (2H, d, J=8.4 Hz), 7.16 (H,s), 7.28–7.37 (5H,m), 7.39 (2H,d, J=8.4 Hz), 7.42–7.47 (4H,m) ppm.

Example 78

1-(4-Cyanobenzyl)-5-(4-biphenylmethyl)-2-methylimidazole trifluoroacetate salt Step A: 1-Trityl-4-(4-biphenylmethyl)-2-methylimidazole The title compound was prepared using the protocol described in Example 1, Step A except using the corresponding amounts of 4-chloromethylbiphenyl and 1-trityl-4-iodo-2-methylimidazole.

FAB MS 491.31 (MH$^+$); H$^1$ NMR (CDCL3, 400 MHz) δ 1.63 (3H,s), 3.88 (2H,s), 6.47 (H,s), 7.12–7.16 (6H, m), 7.29–7.34 (12H,m), 7.41 (2H,t, J=7.6 Hz), 7.49 (2H,d, J=7.6 Hz) 7.56 (2H, dd, J=8.8 and 0.8 Hz) ppm.

Step B: 1–4-Cyanobenzyl)-5-(4-biphenylmethyl)-2-methylimidazole trifluoroacetate salt The title compound was prepared using the protocol described in Example 5, Step C using the product from Step A above and the corresponding amount of 4-cyanobenzyl alcohol but purified as in Example 3, Step B.

Anal. Calc'd for $C_{25}H_{21}N_3$•0.70 $H_2O$•0.40 TFA. C, 62.32; H, 4.48; N, 7.84. Found: C, 62.36; H, 4.42; N, 7.87; FAB MS 364.09 (MH$^+$); H$^1$ NMR (CD$_3$OD, 500 MHz) δ 2.58 (3H,s), 4.05 (2H,s), 5.49 (2H,s), 7.06 (2H, d, J=8.8 Hz), 7.18 (2H, d J=8.8 Hz), 7.33 (H,m), 7.39 (H,s), 7.42 (2H,m), 7.43 (2H,m), 7.51 (2H,m), 7.60 (2H,d, J=8.8 Hz) ppm.

Example 79

1-(4-Cyanobenzyl)-5-[1-(4-biphenyl)]ethyl-2-methyl imidazole

The alcohol from Example 77 (181 mg, 460 mmol) dissolved in $CH_2Cl_2$ (8 mL) and this solution was. added to a mixture of trimethylsilyl chloride (770 mL, 6 mmol) and NaI (900 mg, 6 mmol). The dark mixture was stirred at room temperature for 20 hours. The reaction mixture was distributed between $H_2O$ (100 mL) and CHCl$_3$ (50 mL). The organic layer was washed with saturated Na$_2$S$_2$O$_3$ and water. The solvent was evaporated and the residue was chromatographed (silica gel, 2.5–5% CH$_3$OH—CHCl$_3$) to afford the title compound.

Anal. Calc'd for $C_{26}H_{23}N_3$•0.15 CHCl$_3$; C, 79.43; H, 5.90; N, 10.63. Found: H, 5.74; N, 10.06. FAB MS 378.13 (MH$^+$); H$^1$ NMR (CDCl$_3$, 400 MHz) δ 1.59 (3H, d, J=7.2 Hz), 2.27 (3H,s), 3.74 (H,q, J=7.2 Hz). 4.76 (H,d, J=18 Hz), 4.93 (H,d, J=18 HZ, 6.83 (2H,d, J=8.4 Hz), 7.05–7.09 (3H, m), 7.32–7.36 (H,m) 7.38–7.46 (4H,m) 7.48–7.53 (4H,m) ppm.

Example 80

1-(4-Cyanobenzyl-5-[1-(4-biphenyl)]vinylidene-2-methylimidazole

The alcohol from Example 77 (59 mg, 150 μmol) was stirred in TFA (1 mL) at 55° C. for 20 hours. The clear solution was then cooled and distributed between EtOAc and sat. NaHCO$_3$. The organic layer was separated, dried and the solvent was evaporated. The residue was chromatographed (silica gel. 2.5% CH$_3$OH—CHCl$_3$) to afford the title compound.

Anal. Calc'd for C$_{26}$H$_{21}$N$_3$•0.05 CHCl$_3$•0.25 CH$_3$OH; C, 81.10; H, 5.71; N. 10.79; Found: C, 81.43; H, 6.08; N, 10.59. FAB MS 376.43 (MH$^+$); H$^1$ NMR (CDCl$_3$, 400 MHz) δ 2.34 (3H,s), 4.83 (2H,s), 5.32 (H,d, J=1.2 Hz), 5.56 (H,d,=1.2 Hz), 6.90 (2H, d, J=8.4 Hz), 7.10 (H,s), 7.26–7.29 (2H,m) 7.34–7.39 (H,m), 7.43–7.59 (8H,m) ppm.

Example 81

1-(4-Cyanobenzyl)-5-[2-(4-biphenyl)]vinylene-2-methylimidazole trifluoroacetate salt Step A: 1-Trityl-4-[(2-(4-biphenyl)]vinylene-2-methyl imidazole The title compound was prepared using the protocol described in Example 30 using 1-trityl-4-iodo-2-methylimidazole. The dark solution was cooled and chromatographed (silica gel, 0.5% MeOH—CHCl$_3$) and rechromatographed (silica gel, 20% EtOAc-hexane) to give product as a 3:1 mixture of the desired 1,2 vinylene and 1,1 vinylidene as evidenced by NMR.

FAB MS 503.39 (MH$^+$).

Step B: 1-(4-Cyanobenzyl)-5-[2-(4-biphenyl)]vinylene-2-methylmidazole trifluoroacetate salt The title compound was prepared using the protocol described in Example 5, Step C using the corresponding amounts of the product from Step A above and 4-cyanobenzyl alcohol.

Anal. Calc'd for C$_{26}$H$_{21}$N$_3$•1.25 TFA•0.60 H$_2$O: C, 64.73; H, 4.47; N, 7.95; Found: C, 64.71; H, 4.47; N. 7.82; FAB MS 376.08 (MH$^+$); H$^1$ NMR (CD$_3$OD, 500 Hz) δ 2.67 (3H,s), 5.70 (2H,s), 6.98 (H,d, J=16.7 Hz), 7.29 (H,d, J=16.7 Hz), 7.34 (H,m), 7.39–7.46 (4H,m) 7.57 (2H,d, J=7.5 Hz), 7.61–7.64 (4H,m) 7.79 (2H, d, J=9 Hz), 7.86 (H,s) ppm.

Example 82

In vitro Inhibition of Ras Farnesyl Transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvester, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Example 1–31 were tested for inhibitory activity against human FPTase by the assay described above and were found to have IC$_{50}$ of ≦50 μM.

Example 83

In vivo Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al.,*J. Virol.*43:294–304, (1982)). Following a 2 hour antibody incubation at 4° C., 200 ml of a 25% suspension of protein A-Sepharose coated With rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 84

In vivo Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula A:

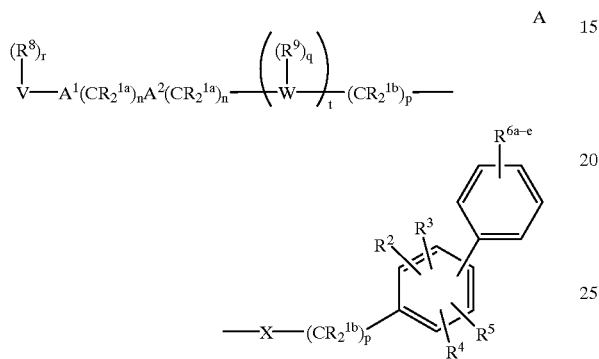

wherein:
$R^{1a}$ and $R^{1b}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^2$, $R^3$, $R^4$ and $R^5$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently, selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{11}S(O)_mNR^{10}$—, $(R^{10})_2NS(O)_m$—, $R^{13}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^3$, $R^4$, $R^5$, $R^{6a}$, $R^{6b}$, $R^{6c}$, $R^{6d}$ or $R^{6e}$ is unsubstituted or substituted heterocycle, attachment of $R^2$, $R^3$, $R^4$, $R^5$, $R^{6a}$, $R^{6b}$, $R^{6c}$, $R^{6d}$ or $R^{6e}$ to the phenyl ring is through a ring carbon of the hererocycle;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e)

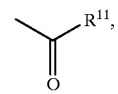

f) —SO$_2$R$^{11}$
  g) N(R$^{10}$)$_2$ or
  h) $C_{1-4}$ perfluoroalkyl;

$R^8$ is independently selected from:
  a) hydrogen,
  b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $N_3$, —$N(R^{10})_2$, or $R^{10}OC(O)NH$—;

provided that when $R^8$ is heterocycle, attachment of $R^8$ to V is through a ring carbon of $R^8$;

$R^9$ is independently selected from:
  a) hydrogen,
  b) $C_2$–$C_6$ alkenyl, $C_2$–$C_6$ alkynyl, $C_1$–$C_6$ perfluoroalkyl, halogen, $R^{11}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{13}$ is independently selected from hydrogen, $C_1$–$C_6$ alkyl, 2,2,2-trifluoroethyl, —$CH_2N(R^{10})_2$, benzyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$— or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a ring carbon of V;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —S(O)$_2$N(R$^{10}$)—, —N(R$^{10}$)S(O)$_2$— or —S(=O)$_m$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

2. The compound according to claim 1 of the formula A:

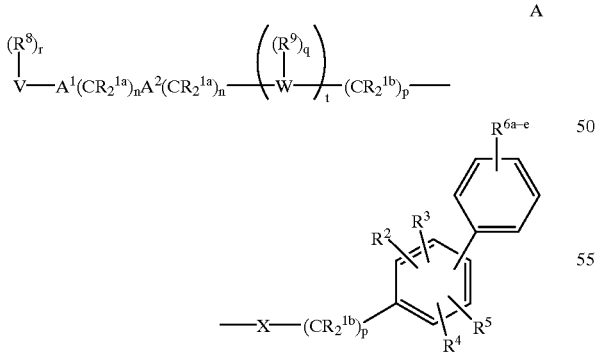

A wherein:

$R^{1a}$ is independently selected from: hydrogen, $C_3$–$C_{10}$ cycloalkyl, $R^{10}$O—, —N(R$^{10}$)$_2$, F or $C_1$–$C_6$ alkyl;

$R^{1b}$ is independently selected from:
a) hydrogen,
b) aryl, heterocycle, $C_3$–$C_{10}$ cycloalkyl, $R^{10}$O—, —N(R$^{10}$)$_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}$O— and —N(R$^{10}$)$_2$;

$R^2$, $R^3$, $R^4$ and $R^5$ are independently selected from:
a) hydrogen,
b) unsubstituted or substituted aryl, urisubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, NO$_2$, $R^{10}$C(O)—, N$_3$, —N(R$^{10}$)$_2$, or $R^{11}$OC(O)NR$^{10}$—,
c) unsubstituted $C_1$–$C_6$ alkyl;
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, $R^{10}$C(O)—, N$_3$, —N(R$^{10}$)$_2$, and $R^{11}$OC(O)—NR$^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, (R$^{10}$)$_2$NC(O)—, $R^{10}{}_2$N—C(NR$^{10}$)—, CN, NO$_2$, $R^{10}$C(O)—, N$_3$, —N(R$^{10}$)$_2$, or $R^{11}$OC(O)NR$^{10}$—,
c) unsubstituted $C_1$–$C_6$ alkyl;
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{11}$S(O)$_m$NR$^{10}$—, (R$^{10}$)$_2$NS(O)$_m$—, $R^{13}$C(O)NR$^{10}$—, (R$^{10}$)$_2$NC(O)—, $R^{10}{}_2$N—C(NR$^{10}$)—, CN, $R^{10}$C(O)—, N$_3$, —N(R$^{10}$)$_2$, and $R^{11}$OC(O)—NR$^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^3$, $R^4$, $R^5$, $R^{6a}$, $R^{6b}$, $R^{6c}$, $R^{6d}$ or $R^{6e}$ is unsubstituted or substituted heterocycle, attachment of $R^2$, $R^3$, $R^4$, $R^5$, $R^{6a}$, $R^{6b}$, $R^{6c}$, $R^{6d}$ or $R^{6e}$ to the phenyl ring is through a ring carbon of the heterocycle;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,
e) 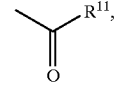

f) —SO$_2$R$^{11}$
g) N(R$^{10}$)$_2$ or h) $C_{1-4}$ perfluoroalkyl;

$R^8$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$, alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a ring carbon of $R^8$;

$R^9$ is independently selected from:
  a) hydrogen,
  b) $C_2$–$C_6$ alkenyl, $C_2$–$C_6$ alkynyl, $C_1$–$C_6$ perfluoroalkyl, F, Cl, $R^{11}O$—, $R^{11}S(O)_m$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10C(O)}NR^{10}$—, $(R^{10})_2NC(O)$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl a nd 2,2,2-trifluoroethyl;

$R^{13}$ is independently selected from hydrogen, $C_1$–$C_6$ alkyl, 2,2,2-trifluoroethyl, —$CH_2N(R^{10})_2$, benzyl and aryl;

$A^1$ and $A^2$ are independently selected from: a bond, —CH=CH—, —C≡C—, —C(O)—, —C(O)NR^{10}$—, O, —$N(R^{10})$—, or $S(O)_m$;

V is selected from:
  a) hydrogen,
  b) heterocycle selected from pyrrolidinyl, imidazolyl, imidazolinyl, pyridinyl, thiazolyl, oxazolyl, indolyl, quinolinyl, isoquinolinyl, triazolyl and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a ring carbon of V;

W is a heterocycle selected from pyrrolidinyl, imidazolyl, imidazolinyl, pyridinyl, thiazolyl, oxazolyl, indolyl, quinolinyl, triazolyl or isoquinolinyl;

X is a bond, O, —C(=O)—, —CH=CH—, —C(O)NR^7$—, —$NR^7C(O)$—, —$S(O)_2N(R^{10})$—, —$N(R^{10})S(O)_2$— or —$S(=O)_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;

or a pharmaceutically acceptable salt thereof.

3. The compound according to claim 1 of the formula B:

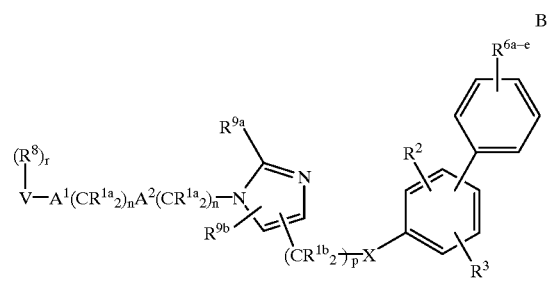

wherein:

$R^{1a}$ is independently selected from: hydrogen, $C_3$–$C_{10}$ cycloalkyl, $R^{10}O$—, —$N(R^{10})_2$, F or $C_1$–$C_6$ alkyl;

$R^{1b}$ is independently selected from:
  a) hydrogen,
  b) aryl, heterocycle, $C_3$–$C_{10}$ cycloalkyl, $R^{10}O$—, —$N(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^2$ and $R^3$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}S(O)_mNR^{10}$—, $(R^{10})_2NS(O)_m$—, $R^{13}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^3$, $R^{6a}$, $R^{6b}$, $R^{6c}$, $R^{6d}$ or $R^{6e}$ is unsubstituted or substituted heterocycle, attachment of $R^2$, $R^3$, $R^{6a}$, $R^{6b}$, $R^{6c}$, $R^{6d}$ or $R^{6e}$ to the phenyl ring is through a ring carbon of the heterocycle;

$R^8$ is independently selected from:
 a) hydrogen,
 b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C((O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

provided that when $R^8$ is heterocycle, attachment of $R^8$ to V is through a ring carbon of $R^8$;

$R^{9a}$ and $R^{9b}$ are independently hydrogen, C$_1$–C$_6$ alkyl, trifluoromethyl and halogen;

$R^{10}$ is independently selected from hydrogen, C$_1$–C$_6$ alkyl, 2,2,2-trifluoroethyl, benzyl and aryl;

$R^{11}$ is independently selected from C$_1$–C$_6$ alkyl and aryl;

$R^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted hetearyl, C$_1$–C$_6$ perfluoroalkyl, 2-aminoethyl and 2,2,2-trifluoroethyl;

$R^{13}$ is independently selected from hydrogen, C$_1$–C$_6$ alkyl, 2,2,2-trifluoroethyl, —CH$_2$N(R$^{10}$)$_2$, benzyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, or S(O)$_m$;

V is selected from:
 a) hydrogen,
 b) heterocycle selected from pyrrolidinyl, imidazolyl, imidazolinyl, pyridinyl, thiazolyl, oxazolyl, indolyl, quinolinyl, isoquinolinyl, triazolyl and thienyl,
 c) aryl,
 d) C$_1$–C$_{20}$ alkyl wherein from 0 to 4 carbon atoms are replaced with a heteroatom selected from O, S, and N, and
 e) C$_2$–C$_{20}$ alkenyl, and provided that V is not hydrogen if $A^1$ is S(O)$_m$ and V is not hydrogen if $A^1$ is a bond, n is 0 and $A^2$ is S(O)$_m$;

provided that when V is heterocycle, attachment of V to $R^8$ and to $A^1$ is through a ring carbon of V;

X is a bond, —CH=CH—, —C(O)NR$^{10}$—, —NR$^{10}$C(O)—, O or —C(=O)—;

m is 0, 1 or 2;

n is independently 0, 1, 2, 3 or 4;

p is 0, 1, 2, 3 or 4; and r is 0 to 5, provided that r is 0 when V is hydrogen;

or a pharmaceutically acceptable salt thereof.

4. The compound according to claim 1 of the formula C:

wherein:

$R^{1a}$ is independently selected from: hydrogen, C$_3$–C$_{10}$ cycloalkyl, R$^{10}$O—, —N(R$^{10}$)$_2$, F or C$_1$–C$_6$ alkyl;

$R^{1b}$ is independently selected from:
 a) hydrogen,
 b) aryl, heterocycle, C$_3$–C$_{10}$ cycloalkyl, R$^{10}$O—, —N(R$^{10}$)$_2$, F or C$_2$–C$_6$ alkenyl,
 c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^{10}$O— and —N(R$^{10}$)$_2$;

$R^2$ and $R^3$ are independently selected from:
 a) hydrogen,
 b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, CN(R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$O—C(O)NR$^{10}$—,
 c) unsubstituted C$_1$–C$_6$ alkyl,
 d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

$R^{6a}$, $R^{6b}$, $R^{6c}$, $R^{6d}$ and $R^{6e}$ are independently selected from:
 a) hydrogen,
 b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, CN(R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
 c) unsubstituted C$_1$–C$_6$ alkyl,
 d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{11}$S(O)$_m$NR$^{10}$—, (R$^{10}$)$_2$NS(O)$_m$—, R$^{13}$C(O)NR$^{10}$—, (R$^{10}$)$_2$NC(O)—, R$^{10}$$_2$N —C(NR$^{10}$)—, CN, R$^{10}$OC(O)—, N$_3$, —N(R$^{10}$)$_2$, and R$^{11}$OC(O)—NR$^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^2$, $R^3$, $R^{6a}$, $R^{6b}$, $R^{6c}$, $R^{6d}$ or $R^{6e}$ is unsubstituted or substituted heterocycle, attachment of $R^2$, $R^3$, $R^{6a}$, $R^{6b}$, $R^{6c}$, $R^{6d}$ or $R^{6e}$ to the phenyl ring is through a ring carbon of the heterocycle;

$R^8$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$, $R^{10}C(O)$—, —$N(R^{10})_2$, or $R^{11}OC(O)NR^{10}$—;

provided that when $R^8$ is heterocycle, attachment of $R^8$ to V is through a ring carbon of $R^8$;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{13}$ is independently selected from hydrogen, $C_1$–$C_6$ alkyl, 2,2,2-trifluoroethyl, —$CH_2N(R^{10})_2$, benzyl and aryl;

$A^1$ and $A^2$ are independently selected from: a bond, —CH=CH—, —C≡C—, —C(O)—, —C(O)$NR^{10}$—, O, —$N(R^{10})$—, or $S(O)_m$;

V is selected from:
  a) hydrogen,
  b) heterocycle selected from pyrrolidinyl, imidazolyl, imidazolinyl, pyridinyl, thiazolyl, oxazolyl, indolyl, quinolinyl, isoquinolinyl, triazolyl and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a ring carbon of V;

X is a bond, —CH=CH—, —C(O)$NR^{10}$—, —$NR^{10}C(O)$—, O or —C(=O)—;

m is 0, 1 or 2;

n is independently 0, 1, 2, 3 or 4;

p is 0, 1, 2, 3 or 4, provided that p is not 0 if X is a bond, —$NR^{10}C(O)$—, —$NR^{10}$— or O; and r is 0 to 5, provided that r is 0 when V is hydrogen;

or a pharmaceutically acceptable salt thereof.

5. The compound according to claim 3 of the formula D:

wherein:

$R^{1a}$ is independently selected from: hydrogen, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^{10}O$—, —$N(R^{10})_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^2$ is selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^3$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^2$, $R^{6a}$, $R^{6b}$, $R^{6c}$, $R^{6d}$ or $R^{6e}$ is unsubstituted or substituted heterocycle, attachment of $R^2$, $R^{6a}$, $R^{6b}$, $R^{6c}$, $R^{6d}$ or $R^{6e}$ to the phenyl ring is through a ring carbon of the heterocycle;

$R^8$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—; or provided that when $R^8$ is heterocycle, attachment of $R^8$ to V is through a ring carbon of $R^8$;

$R^{9a}$ and $R^{9b}$ are independently hydrogen, halogen, $CF_3$ or methyl;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$A^1$ is selected from: a bond, —C(O)—, O, —$N(R^{10})$—, or $S(O)_m$;

X is a bond, —CH=CH—, —$C(O)NR^{10}$—, —$NR^{10}C(O)$—, O or —C(=O)—;

n is 0 or 1; provided that n is not 0 if $A^1$ is a bond, O, —$N(R^{10})$—, or $S(O)_m$;

m is 0, 1 or 2; and p is 0, 1, 2, 3 or 4;

or the pharmaceutically acceptable salts thereof.

6. The compound according to claim 4 of the formula E:

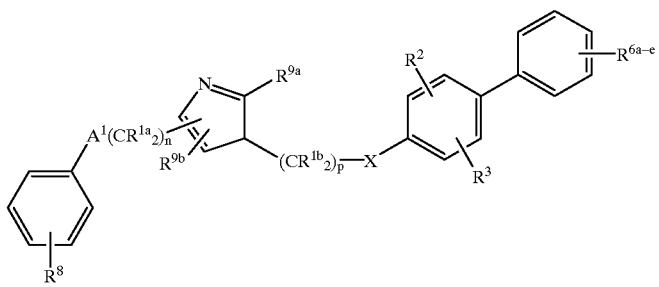

E wherein:

$R^{1a}$ is independently selected from: hydrogen, $R^{10}O$—, —$N(R^{10})_2$, F, $C_3$–$C_{10}$ cycloalkyl or $C_1$–$C_6$ alkyl;

$R^{1b}$ is independently selected from:
 a) hydrogen,
 b) aryl, heterocycle, $C_3$–$C_{10}$ cycloalkyl, $R^{10}O$—, —$N(R^{10})_2$, F or $C_2$–$C_6$ alkenyl,
 c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^2$ is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ aryl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

$R^3$ is selected from H, halogen, $C_1$–$C_6$ alky and $CF_3$;

$R^{6a}$, $R^{6b}$, $R^{6c}$, $R^{6d}$ and $R^{6e}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^2$, $R^{6a}$, $R^{6b}$, $R^{6c}$, $R^{6d}$ or $R^{6e}$ is unsubstituted or substituted heterocycle, attachment of $R^2$, $R^{6a}$, $R^{6b}$, $R^{6c}$, $R^{6d}$ or $R^{6e}$ to the phenyl ring is through a ring carbon of the heterocycle;

$R^8$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a ring carbon of $R^8$;

$R^{9a}$ and $R^{9b}$ are independently hydrogen, halogen, $CF_3$ or methyl;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, O or —C(=O)—;

n is 0 or 1;

m is 0, 1 or 2; and p is 0, 1, 2, 3 or 4, provided that p is not 0 if X is a bond or O;

or the pharmaceutically acceptable salts thereof.

7. The compound according to claim 5 of the fonnula F:

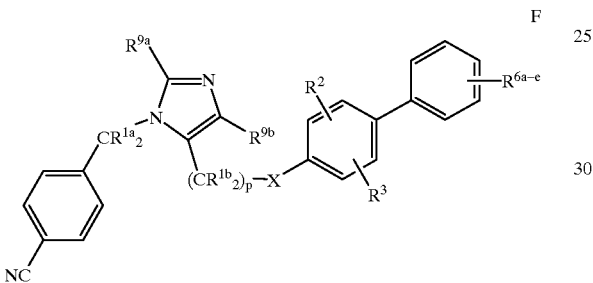

F wherein:

$R^{1a}$ is independently selected from: hydrogen, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^{10}$O—, —N($R^{10}$)$_2$ or F,
  c) $C_1$–$C_6$ alkyl unsubstituted or substituted by aryl, heterocycle, $C_3$–$C_{10}$ cycloalkyl, $R^{10}$O—, or —N($R^{10}$)$_2$;

$R^2$ is selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}$$_2$N—C(NR$^{10}$)—, CN, NO$_2$, $R^{10}$C(O)—, N$_3$, —N($R^{10}$)$_2$, or $R^{11}$OC(O)NR$^{10}$—,
  c) unsubstituted $C_1$–$C_6$ alkyl,
  d) substituted $C_1$–$C_6$ alkyl wherein the substituent on the substituted $C_1$–$C_6$ alkyl is selected fiom unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}$$_2$N—C(NR$^{10}$)—, CN, $R^{10}$C(O)—, N$_3$, —N($R^{10}$)$_2$, and $R^{11}$OC(O)—NR$^{10}$—;

$R^3$ is selected from H, halogen, $CH_3$ and $CF_3$;

$R^{6a}$, $R^{6b}$, $R^{6c}$, $R^{6d}$ and $R^{6e}$ are independently selected from:

a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}$$_2$N—C(NR$^{10}$)—, CN, NO$_2$, $R^{10}$C(O)—, N$_3$, —N($R^{10}$)$_2$, or $R^{11}$OC(O)NR$^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}$$_2$N—C(NR$^{10}$)—, CN, $R^{10}$C(O)—, N$_3$, —N($R^{10}$)$_2$, and $R^{11}$OC(O)—NR$^{10}$—; or provided that when $R^2$, $R^{6a}$, $R^{6b}$, $R^{6c}$, $R^{6d}$ or $R^{6e}$ is unsubstituted or substituted heterocycle, attachment of $R^2$, $R^{6a}$, $R^{6b}$, $R^{6c}$, $R^{6d}$ or $R^{6e}$ to the phenyl ring is through a ring carbon of the heterocycle;

$R^{9a}$ and $R^{9b}$ are independently hydrogen, halogen, $CF_3$ or methyl;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, O or —C(=O)—;

m is 0, 1 or 2; and p is 0, 1, 2, 3 or 4;

or the pharmaceutically acceptable salts thereof.

8. The compound according to claim 6 of the formula G:

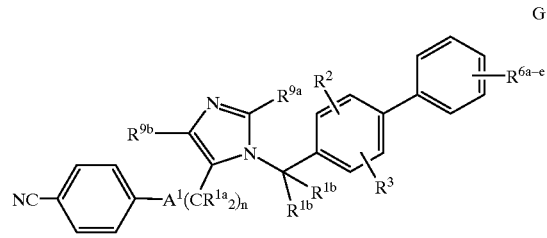

G wherein:

$R^{1a}$ is independently selected from: hydrogen, $R^{10}$O—, —N($R^{10}$)$_2$, F, $C_3$–$C_{10}$ cycloalkyl or $C_1$–$C_6$ alkyl;

$R^{1b}$ is independently selected from:
  a) hydrogen,
  b) aryl, heterocycle or $C_3$–$C_{10}$ cycloalkyl,
  c) $C_1$–$C_6$ alkyl unsubstituted or substituted by aryl, heterocycle, $C_3$–$C_{10}$ cycloalkyl, $C_2$–$C_6$ alkenyl, $R^{10}$O—, or —N($R^{10}$)$_2$;

$R^2$ is selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}$$_2$N—C(NR$^{10}$)—, CN, NO$_2$, $R^{10}$C(O)—, N$_3$, —N($R^{10}$)$_2$, or $R^{11}$OC(O)NR$^{10}$—, c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^3$ is selected from H, halogen, $CH_3$ and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or
any two of $R^{6a}$, $R^{6b}$, $R^{6c}$, $R^{6d}$ and $R^{6e}$ on adjacent carbon atoms are combined to from a diradical selected from —CH=CH—CH=CH—, —CH=CH—$CH_2$—, —$(CH_2)_4$— and —$(CH_2)_3$—;
provided that when $R^2$, $R^{6a}$, $R^{6b}$, $R^{6c}$, $R^{6d}$ or $R^{6e}$ is unsubstituted or substituted heterocycle, attachment of $R^2$, $R^{6a}$, $R^{6b}$, $R^{6c}$, $R^{6d}$ or $R^{6e}$ to the phenyl ring is through a ring carbon of the heterocycle;

$R^{9a}$ and $R^{9b}$ are independently hydrogen, halogen, $CF_3$ or methyl;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ is selected from: a bond, —C(O)—, O, —$N(R^{10})$—, or $S(O)_m$;

m is 0, 1 or 2; and
n is 0 or 1;
or the pharmaceutically acceptable salts thereof.

9. A compound which inhibits farnesyl-protein transferase which is:

1-(4-Cyanobenzyl)-5-(4'-phenylbenzamido)ethyl-imidazole 1-(2'-Trifluoromethyl-4-biphenylmethyl)-5-(4-cyanobenzyl)imidazole 1-(4-Biphenylethyl)-5-(4-cyanobenzyl)imidazole 1-(2'-Bromo-4-biphenylmethyl)-5-(4-cyanobenzyl) imidazole 1-(2'-Methyl-4-biphenylmethyl)-5-(4-cyanobenzyl) imidazole 1-(2'-Trifluoromethoxy-4-biphenylmethyl)-5-(1-cyanobenzyl) imidazole 1-(4-(3',5'-dichloro)-biphenylmethyl)-5-(4-cyanolbenzyl) imidazole 1-(2'-Methoxy-4-biphenylmethyl)-5-(4-cyanobenzyl) imidazole 1-(2'-Chloro-4-biphenylmethyl)-5-(4-cyanobenzyl) imidazole 1-(2-Chloro-4-biphenylmethyl)-5-(4-cyanobenzyl) imidazole 1-(3-Chloro-4-biphenylmethyl)-5-(4-cyanobenzyl) imidazole 1-(4-(3',5'-Bis-trifluoromethyl)-biphenylmethyl)-5-(4-cyanobenzyl) imidazole 1-(2'-Trifluoromethyl-4-biphenylmethyl)-5-(4-cyanobenzyl)-4-methylimidazole 1-(4-Biphenylmethyl)-5-(4-cyanophenyloxy)-imidazole 5-(4-Cyanophenyloxy)-1-(2'-methyl-4-biphenylmethyl)-imidazole 5-(4-Biphenyloxy)-1-(4-cyanobenzyl)-imidazole 5-(2'-Methyl-4-biphenoxy)-1-(4-cyanobenzyl)-imidazole 5-(4-(3',5'-dichloro)biphenylmethyl)-1-(4-cyanobenzyl) imidazole 1-(4-biphenylmethyl)-5-(1-(R,S)-acetoxy-1-(4-cyanophenyl)methylimidazole 1-(4-Biphenylmethyl)-5-(1-(R,S)-hydroxy-1-(4-cyanophenyl) methylimidazole 1-(4-Biphenylmethyl)-5-(1-(R,S)-amino-1-(4-cyanophenyl) methylimidazole 1-(4-biphenylmethyl)-5-(1-(R,S)-methoxy-1-(4-cyanophenyl)-methylimidazole 1-(4-Cyanobenzyl)-5-(1-hydroxy-1-(3-fluoro-4-biphenyl)-methyl)-imidazole 1-(4-Cyanobenzyl)-5-(1-hydroxy-1-(3-biphenyl)methyl-imidazole 5-(2-[1,1'-Biphenyl]vinylene)-1-(4-cyanobenzyl) imidazole 1-(4-Biphenylmethyl)-5-(4-bromophenyloxy)-inidazole 1-(3'-Methyl-4-biphenylmethyl)-5-(4-cyanobenzyl) imidazole 1-(4'-Methyl-4-biphenylmethyl)-5-(4-cyanobenzyl) imidazole 1-(3'-Trifluoromethyl-4-biphenylmethyl)-5-(4-cyanobenzyl) imidazole 1-(4'-Trifluoromethyl-4-biphenylmethyl)-5-(4-cyanobenzyl) imidazole 1-(3'-Chloro-4-biphenylmethyl)-5-(4-cyanobenzyl) imidazole 1-(4'-Chloro-4-biphenylmethyl)-5-(4-cyanobenzyl) imidazole 1-(2'3'-Dichloro-4-biphenylmethyl)-5-(4-cyanobenzyl) imidazole 1-(2'4'-Dichloro-4-biphenylmethyl)-5-(4-cyanolenzyl) imidazole 1-(2'5'-Dichloro-4-biphenylmethyl)-5-(4-cyanobenzyl) imidazole 1-(3'-Trifluoromethoxy-4-biphenylmethyl)-5-(4-cyanobenzyl) imidazole 1-(2'-Fluoro-4-biphenylmethyl)-5-(4-cyanobenzyl) imidazole 1-(4-(2'-Trifluoromethylphenyl)-2-Chlorophenylmethyl)-5-(4-cyanobenzyl)imidazole 1-{1-(4-(2'-trifluoromethylphenyl)phenyl)ethyl}-5-(4-cyanobenzyl) imidazole
1-(2'-Trifluoromethyl-4-biphenylpropyl)-5-(4-cyanobenzyl) imidazole
1-(2'-N-t-Butoxycarbonylamino-4-biphenylmethyl)-5-(4-cyanobenzyl)imidazole
1-(2'-Aminomethyl-4-biphenylmethyl)-5-(4-cyanobenzyl)imidazole
1-(2'-Acetylaminomethyl-4-biphenylmethyl)-5-(4-cyanobenzyl) imidazole
1-(2'-Methylsulfonylaminomethyl-4-biphenylmethyl)-5-(4-cyanobenzyl)imidazole
1-(2'-Ethylaminomethyl-4-biphenylmethyl)-5-(4-cyanobenzyl) imidazole
1-(2'-Phenylaminomethyl-4-biphenylmethyl)-5-(4-cyanobenzyl) imidazole
1-(2'-Glycinylaminomethyl-4-biphenylmethyl)-5-(4-cyanobenzyl) imidazole
1-(2'-Methyl-4-biphenylmethyl)-2-chloro-5-(4-cyanobenzyl) imidazole
1-(2'-Methyl-4-biphenylmethyl)-4-chloro 5-(4-cyanobenzyl) imidazole
1-(3'-Chloro-2-methyl-4-biphenylmethyl)-4-(4-cyanobenzyl)imidazole
1-(3'-Chloro-2-methyl-4-biphenylmethyl)-5-(4-cyanobenzyl)imidazole
1-(3'-Trifluoromethyl-2-methyl-4-biphenylmethyl)-4-(4-cyanobenzyl)imidazole
1-(3'-Trifluoromethyl-2-methyl-4-biphenylmethyl)-5-(4-cyanobenzyl)imidazole
1-(3'-Methoxy-2-methyl-4-biphenylmethyl)-5-(4-cyanobenzyl)imidazole
1-(2'-Chloro-4'-fluoro-4-biphenylmethyl)-5-(4-cyanobenzyl)imidazole
1-(2'-Ethyl-4-biphenylmethyl)-5-(4-cyanobenzyl) imidazole
1-(2'-(2-Propyl)-4-biphenylmethyl)-5-(4-cyanobenzyl) imidazole
1-(2'-(2-Methyl-2-propyl)-4-biphenylmethyl)-5-(4-cyanobenzyl)imidazole
1-(2'-Ethyl-4-biphenylmethyl)-5-(4-(1H-tetrazol-5-yl))benzyl)imidazole
1-[1-(4-Cyanobenzyl)imidazol-5-ylmethoxy]-4-(2'-methylphenyl)-2-(3-N-phthalimido-1-propyl)benzene
1-(3',5'-Ditrifluoromethyl-2-methyl-4-biphenylmethyl)-5-(4-cyanobenzyl)imidazole
1-(3',5'-Chloro-2-methyl-4-biphenylmethyl)-5-(4-cyanobenzyl)imidazole
1-(3',5'-Dimethyl-2-methyl-4-biphenylmethyl)-5-(4-cyanobenzyl)imidazole
1-(3-(N-Boc-aminomethyl)-4-biphenylmethyl)-5-(4-cyanobenzyl)-imidazole
1-(3-Aminomethyl)-4-biphenylmethyl)-5-(4-cyanobenzyl)imidazole
1-(4-Cyanobenzyl)-2-methyl-5-(2'-methylbiphenyl-4-yloxy)imidazole
5-(4-Cyanobenzyl)-1-(3-cyano-2'-trifluoromethylbiphenyl-4-ylmethyl)-imidazole
2-Amino-5-(biphenyl-4-ylmethyl)-1-(4-cyanobenzyl) imidazole
2-Amino-1-(biphenyl-4-ylmethyl)-5-(4-cyanobenzyl) imidazole
1-(3-Butylbiphenyl-4-ylmethyl)-5-(4-cyanobenzyl)-imidazole
1-(3-Propylbiphenyl-4-ylmethyl)-5-(4-cyanobenzyl)-imidazole
1-(4-Biphenylmethyl)-4-(4-cyanobenzyl-2-methylimidazole
1-(4-Cyanobenzyl)-5-[(3-fluoro-4-biphenyl)methyl] imidazole
1-(4-Cyanobenzyl)-5-[1-(4-biphenyl)-1-hydroxy]ethyl-2-methylimidazole
1-(4-Cyanobenzyl)-5-(4-biphenylmethyl)-2-methylimidazole
1-(4-Cyanobenzyl)-5-[1-(4-biphenyl)]ethyl-2-methyl imidazole
1-(4-Cyanobenzyl-5-[1-(4-biphenyl)]vinylidene-2-methylimidazole or 1-(4-Cyanobenzyl)-5-[2-(4-biphenyl)]vinylene-2-methylimidazole or a pharmaceutically acceptable salt or optical isomer thereof.

10. The compound according to claim 9 which is:

1-(2'-Methoxy-4-biphenylmethyl)-5-(4-cyanobenzyl) imidazole

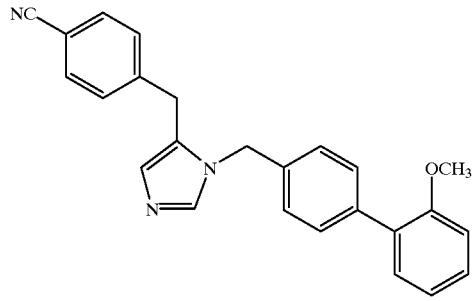

or a pharmaceutically acceptable salt or optical isomer thereof.

11. The compound according to (claim 9 which is:

1-(2'-Methyl-4-biphenylmethyl)-5-(4-cyanobenzyl) imidazole

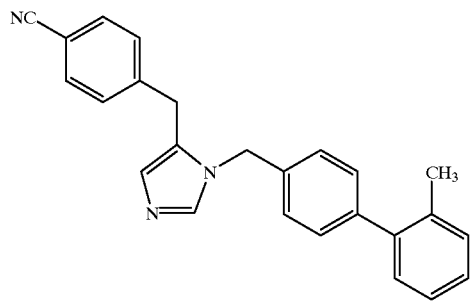

or a pharmaceutically acceptable salt or optical isomer thereof.

12. The compound according to claim 9 which is:

1-(4-(3',5'-dichloro)-biphenylmethyl)-5-(4-cyanobenzyl) imidazole

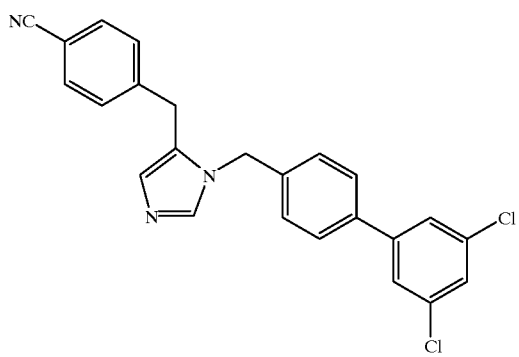

or a pharmaceutically acceptable salt or optical isomer thereof.

13. The compound according to claim 9 which is:

1-(4'-Chloro-4-biphenylmethyl)-5-(4-cyanobenzyl) imidazole

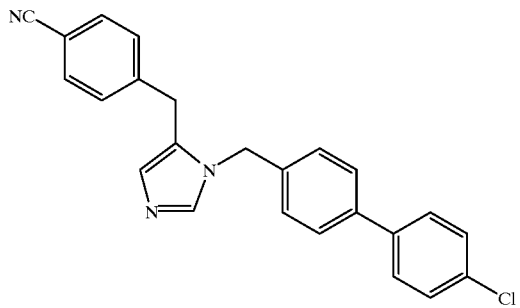

or a pharmaceutically acceptable salt or optical isomer thereof.

14. The compound according to claim 9 which is:

5-(2'-Methyl-4-biphenoxy)-1-(4-cyanobenzyl)-imidazole

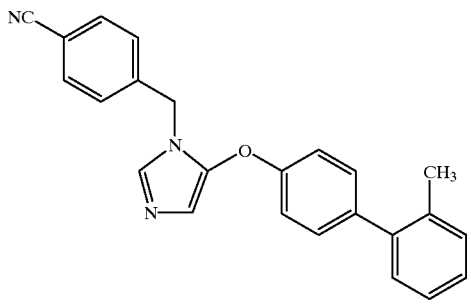

or a pharmaceutically acceptable salt or optical isomer thereof.

15. The compound according to claim 9 which is:

1-(4-Cyanobenzyl)-5-(1-hydroxy-1-(3-fluoro-4-biphenyl)-methyl)-imidazole

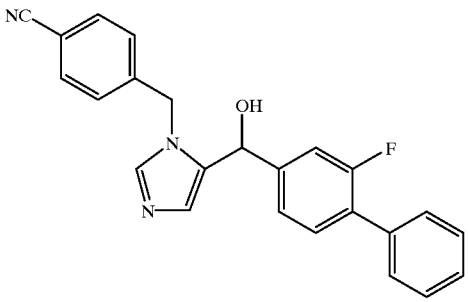

or a pharmaceutically acceptable salt or optical isomer thereof.

16. The compound according to claim 9 which is:

1-(2',5'-Dichloro-4-biphenylmethyl)-5-(4-cyanobenzyl) imidazole

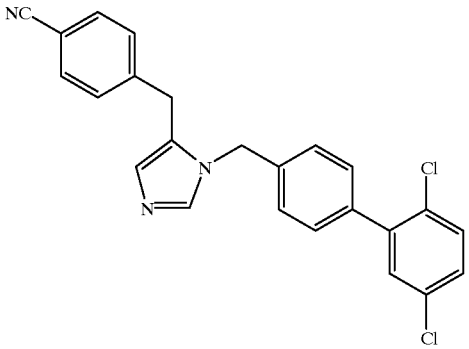

or a pharmaceutically acceptable salt or optical isomer thereof.

17. The compound according to claim 9 which is: 1-(3'-Methoxy-2-methyl-4-biphenylmethyl)-5-(4-cyanobenzyl) imidazole

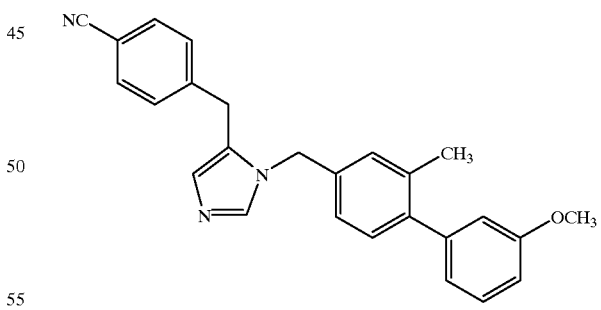

or a pharmaceutically acceptable salt or optical isomer thereof.

18. A pharmaceutical composition comprising a pharmaceutical carrier, and dispersed therein, a therapeutically effective amount of a compound of claim 1.

19. A pharmaceutical composition comprising a pharmaceutical carrier, and dispersed therein, a therapeutically effective amount of a compound of claim 3.

20. A pharmaceutical composition comprising a pharmaceutical carrier, and dispersed therein, a therapeutically effective amount of a compound of claim 4.

21. A pharmaceutical composition comprising a pharmaceutical carrier, and dispersed therein, a therapeutically effective amount of a compound of claim 9.

22. A method for inhibiting farnesyl-protein transferase which comprises administering to a mammal in reed thereof a therapeutically effective amount of a composition of claim 18.

23. A method for inhibiting farnesyl-protein transferase which comprises administering to a mammal in need thereof a therapeutically effective amount of a composition of claim 19.

24. A method for inhibiting farnesyl-protein transferase which comprises administering to a mammal in need thereof a therapeutically effective amount of a composition of claim 20.

25. A method for inhibiting farnesyl-protein transferase which comprises administering to a mammal in need thereof a therapeutically effective amount of a composition of claim 21.

26. A method for treating cancer which comprises administering to a mammal in need thereof a therapeutically effective amount of a composition of claim 18.

27. A method for treating cancer which comprises administering to a mammal in need thereof a therapeutically effective amount of a composition of claim 19.

28. A method for treating cancer which comprises administering to a mammal in need thereof a therapeutically effective amount of a composition of claim 20.

29. A method for treating cancer which comprises administering to a mammal in need thereof a therapeutically effective amount of a composition of claim 21.

30. A method for treating neurofibromin benign proliferative disorder which comprises administering to a mammal in need thereof a therapeutically effective amount of a composition of claim 18.

31. A method for treating blindness related to retinal vascularization which comprises administering to a mammal in need thereof a therapeutically effective amount of a composition of claim 18.

32. A method for treating infections from hepatitis delta and related viruses which comprises administering to a mammal in need thereof a therapeutically effective amount of a composition of claim 18.

33. A method for preventing restenosis which comprises administering to a mammal in need thereof a therapeutically effective amount of a composition of claim 18.

34. A method for treating polycystic kidney disease which comprises administering to a mammal in need thereof a therapeutically effective amount of a composition of claim 18.

35. A pharmaceutical composition made by combining the compound of claim 1 and a pharmaceutically acceptable carrier.

36. A process for making a pharmaceutical composition comprising combining a compound of claim 1 and a pharmaceutically acceptable carrier.

* * * * *